United States Patent
Keene et al.

[11] Patent Number: 5,866,680
[45] Date of Patent: Feb. 2, 1999

[54] RIBONUCLEOPROTEINS AND RNA-BINDING PROTEINS USEFUL FOR THE SPECIFIC RECOGNITION AND BINDING TO RNA, AND FOR CONTROL OF CELLULAR GENETIC PROCESSING AND EXPRESSION

[75] Inventors: Jack D. Keene, 13 Clearwater Dr.; Charles C. Query, 4104 Five Oaks Dr. #12, both of Durham, N.C. 27707; Rex O. Bentley, Durham, N.C.

[73] Assignees: Jack D. Keene; Charles C. Query; Rex Bentley, all of Durham, N.C.

[21] Appl. No.: 474,753

[22] Filed: Jun. 7, 1995

Related U.S. Application Data

[62] Division of Ser. No. 173,941, Dec. 27, 1993, Pat. No. 5,561,222, which is a continuation of Ser. No. 536,943, Jun. 12, 1990, abandoned, which is a continuation-in-part of Ser. No. 436,779, Nov. 15, 1989, abandoned.

[51] Int. Cl.[6] ........................ A61K 38/00; C07K 14/435; C07K 19/00; C07H 21/02
[52] U.S. Cl. ........................ 530/324; 530/350; 536/24.3; 536/24.32
[58] Field of Search ........................... 436/86; 514/25.32, 514/44; 530/350; 536/22.1, 23.1, 24.1; 435/6, 172.1

[56] References Cited

PUBLICATIONS

Mol. Cell. Biol. (1986), vol. 6, pp. 2932–2943.
Cell (1986), vol. 55, pp. 1025–1035.
Nature (1989), vol. 340, pp. 521–524.
Cell (1988), vol. 55, pp. 1037–1046.
J. Mol. Biol. (1988), vol. 200, p. 627–638.
Genes & Dev. (1989), vol. 3, pp. 431–437.
J. Biol. Chem. (1987), vol. 262, pp. 10922–10925.
Proc. Natl. Acad. Sci. (1988), vol. 85, pp. 2538–2542.
Trends in Biochem. Sci. (1988), vol. 13, pp. 86–91.
Cell (1989), vol. 56, pp. 1011–1018.
Embo J. (1988), vol. 7, pp. 4311–4321.
Nuc. Acids. Res. (1987), vol. 57, pp. 4771–4787.
Proc. Natl. Acad. Sci. (USA) (1987), vol. 84, pp. 2421–2425.
Mol. Cell. Biol. (1987), vol. 7, pp. 2947–2955.
J. Biol. Chem. (1988), vol. 263, pp. 3307–3313.

(List continued on next page.)

Primary Examiner—David Guzo
Assistant Examiner—William Sandals
Attorney, Agent, or Firm—Oblon, Spivak, McClelland, Maier & Neustadt, P.C.

[57] ABSTRACT

Ribonucleoproteins and RNA-binding proteins related to the amino acid sequence corresponding at least to residues 92 to 202 and up to about residues 1 to about 240 of sequence (III), or of a modification of such sequences (III) having at least 35% homology with sequence (III) are disclosed. Sequence (III) is:

```
        10                  20
M T Q F L P P N L L A L F A P R D P I P Y L P P L E K L P
30               40               50
H E K H H N Q P Y C G I A P Y I R E F E D P R D A P P P T
60               70               80
R A E T R E E R M E R K R R E K I E R R Q Q E V E T E L K
90              100              110
M W D P H N D P N A Q G D A F K T L F V A R V N Y D T T E
120              130              140
S K L R R E F E V Y G P I K R I H M V Y S K R S G K P R G
150              160              170
Y A F I E Y E H E R D M H S A Y K H A D G K K I D G R R V
180              190              200
L V D V E R G R T V K G W R P R R L G G G L G G T R R G G
210              220
A D V N I R H S G R D D T S R Y D E R P G P G P S P L P
230              240
H R D R D R D R E R E
```

14 Claims, 26 Drawing Sheets

PUBLICATIONS

*Nuc. Acids Res.* (1985), vol. 13, pp. 6577–6591.
*EMBO J.* (1986), vol. 5, pp. 3209–3217.
*Cell* (1989), vol. 57, pp. 89–101.
*Nature* (1988), vol. 336, pp. 522–524.
*Science* (1988), vol. 240, pp. 889–895.
*Cell* (1989), vol. 55, pp. 537–540.
*Science* (1988), vol. 242, pp.1570–1572.
*Mol. Cell. Biol.* (1989), vol. 9, pp. 4872–4881.
*Science* (1988), vol. 242, pp. 1570–1572.
*Nuc. Acids Res.* (1987), vol. 15, pp. 10373–10390.
*Cell* (1987), vol. 51, pp. 211–220.
*Mol. Cell. Biol.* (1989), vol. 9, pp. 4179–4186.
*EMBO J.* (1987), vol. 6, pp. 3841–3848.
*Mol. Cell. Biol.* (1989), vol. 9, pp. 2975–2982.
*EMBO J.* (1989), vol. 8, pp. 4163–4170.
*Nature* (1990), vol. 345, pp. 502–506.
*J. Mol. Biol.* (1989), vol. 207, pp. 491–503.
*Biochem.* (1980), vol. 19, pp. 4674–4682.
*J. Biol. Chem.* (1986), vol. 261, pp. 3536–3543.
*J. Biol. Chem.* (1987), vol. 262, pp. 17126–17137.
*J. Biol. Chem.* (1988), vol. 263, pp. 1063–1071.
*Proc. Natl. Acad. Sci.* (*USA*) (1989), vol. 86; pp. 9788–9792.
*Mol. Cell. Biol.* (1987), vol. 7, pp. 1731–1739.
*Mol. Cell. Biol.* (1988), vol. 8, pp. 2237–2241.
*Cell* (1988), vol. 52, pp. 221–228.
*Proc. Natl. Acad. Sci.* (*USA*) (1986), vol. 83, pp. 2007–2011.
*Proc. Natl. Acad. Sci.* (*USA*) (1987), vol. 84, pp. 1819–1823.
*EMBO J.* (1988), vol. 7, pp. 3519–3529.
*Mol. Cell. Biol.* (1990), vol. 10, pp. 316–323.
*FEBS Letters* (1989), vol. 257, pp. 373–376.
*Cell* (1989), vol. 58, pp. 231–232.
*Nature* (1990), vol. 344, pp. 461–463.
*Mol. Cell. Biol.* (1985), vol. 5, pp. 1993–1996.
*Cell* (1986), vol. 45, pp. 827–835.
*Mol. Cell. Biol.* (1987), vol. 7, pp. 3268–3276.
*Cell* (1989), vol. 58, pp. 857–867.
*Proc. Natl. Acad. Sci.* (*USA*) (1988), vol. 85, pp. 9479–9483.
*J. Biol. Chem.* (1988), vol. 263, pp. 18043–18051.
*J. Biochem.* (1989), vol. 179, pp. 541–548.
*Genes & Dev.* (1989), vol. 3, pp. 324–333.
*J. Biol. Chem.* (1988), vol. 263, pp. 12824–12827.
*Nuc. Acids Res.* (1985), vol. 13, pp. 5805–5816.
Theessen et al EMBO J 5(12):320, 1986.
Spritz et al. NAR 15(24) 10373, 1987.
Hope et al Cell 43: 177, 1985.

| Protein | Pos | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|---|---|---|---|---|---|---|---|---|---|---|---|---|---|---|---|---|---|
| | | x x x | | | x | | | | | + + | | | | x + | | | | x + | | | | + x | | x | | | | | | | | + |
| HUMAN U1snRNP-70K | 104 | T | L | F | V | A | R | V | - | N | Y | D | T | T | E | S | K | - | - | - | L | R | R | E | F | E | V | Y | G | P | I | K | R | I | H | M |
| -XENOPUS U1snRNP-70K | 104 | T | L | F | V | A | R | V | - | N | Y | D | T | T | E | S | K | - | - | - | L | R | R | E | F | E | V | Y | Y | G | P | I | K | R | I | H | I |
| -FLY U1snRNP-70K | 104 | T | L | F | I | A | R | I | - | N | Y | D | T | S | E | S | K | - | - | - | L | R | R | E | F | E | F | Y | G | P | I | K | K | I | V | L |
| HUMAN U1snRNP-A#1 | 11 | T | I | Y | I | N | N | L | N | E | K | I | K | K | D | E | L | K | K | S | L | Y | A | I | F | S | Q | F | G | Q | I | L | D | I | L | V |
| HUMAN U1snRNP-A#2 | 210 | I | L | F | L | T | N | L | - | P | E | E | T | N | E | L | M | - | - | - | L | S | M | L | F | N | Q | F | P | G | F | K | E | V | R | L |
| HUMAN U2snRNP-B"#1 | 8 | T | I | Y | I | N | N | M | N | D | K | I | K | K | E | E | L | K | R | S | L | Y | A | L | F | S | Q | F | G | H | V | V | D | I | V | A |
| HUMAN U2snRNP-B"#2 | 152 | I | L | F | L | N | N | L | - | P | E | E | T | N | E | M | M | - | - | - | L | S | M | L | F | N | Q | F | P | G | F | K | E | V | R | L |
| HUMAN RoRNP-60K | 92 | M | L | F | A | K | A | I | - | C | S | Q | C | S | D | I | S | T | - | - | K | Q | A | A | F | K | A | V | S | E | V | C | R | I | P | - |
| HUMAN UP2 | 173 | K | I | F | V | G | G | L | - | S | P | D | T | P | E | E | K | - | - | - | I | R | E | Y | F | G | G | F | G | E | V | E | S | I | E | L |
| HUMAN hnRNP C1/C2 | 17 | R | V | F | I | G | N | L | - | N | T | L | V | V | K | K | S | D | - | - | V | E | A | I | F | S | K | Y | G | K | I | V | G | C | S | V |
| -XENOPUS hnRNP C1/C2 | 18 | R | V | F | I | G | N | L | - | N | T | L | V | V | K | K | T | D | - | - | V | E | A | I | F | S | K | Y | G | K | I | V | G | C | S | V |
| HUMAN La | 112 | S | V | Y | I | K | G | F | P | T | D | A | T | L | D | D | - | - | - | - | I | K | E | W | L | E | D | K | G | Q | V | L | N | I | Q | M |
| -BOVINE La | 112 | S | V | Y | I | K | G | F | P | T | D | A | A | L | D | D | - | - | - | - | I | K | E | W | L | E | D | K | G | Q | V | L | N | I | Q | M |
| -XENOPUS La | 112 | S | V | Y | I | K | G | F | P | T | S | A | I | L | D | D | - | - | - | - | V | K | E | W | L | K | D | K | G | P | I | E | N | T | Q | M |
| E.COLI Rho N1 | 20 | N | M | G | L | E | N | L | A | R | M | R | K | Q | D | I | - | - | - | - | I | F | A | I | L | K | Q | H | A | K | S | G | E | D | I | F |
| T4 gp32 | 90 | C | Q | Y | I | S | K | N | D | L | Y | N | T | D | N | K | E | Y | S | L | V | K | R | K | T | S | Y | W | A | N | I | L | V | V | K | D |
| HUMAN PABP#1 | 12 | S | L | Y | V | G | D | L | - | H | P | D | V | T | E | A | M | - | - | - | L | Y | E | K | F | S | P | A | G | P | I | L | S | I | R | V |
| HUMAN PABP#2 | 100 | N | I | F | I | K | N | L | - | D | K | S | I | D | N | K | A | - | - | - | L | Y | D | T | F | S | A | F | G | N | I | L | S | C | K | V |
| HUMAN PABP#3 | 192 | N | V | Y | I | K | N | F | - | G | E | D | M | D | D | E | R | - | - | - | L | K | D | L | F | G | P | A | L | S | V | K | - | - | - | V |
| HUMAN PABP#4 | 292 | N | L | Y | V | K | N | L | - | D | D | G | I | D | D | E | R | - | - | - | L | R | K | E | F | S | P | F | G | T | I | I | T | S | A | K | V |
| -YEAST PABP#1 | 39 | S | L | Y | V | G | D | L | - | E | P | S | V | S | E | A | H | - | - | - | L | Y | D | I | F | S | P | I | G | S | V | S | S | I | R | V |
| -YEAST PABP#2 | 127 | N | I | F | I | K | N | L | - | H | P | D | I | D | N | K | A | - | - | - | L | Y | D | T | F | S | V | F | G | D | I | L | S | S | K | I |
| -YEAST PABP#3 | 220 | N | L | Y | V | K | N | I | - | N | S | E | T | T | D | E | Q | - | - | - | F | Q | E | L | F | A | K | F | G | P | I | V | S | A | S | L |
| -YEAST PABP#4 | 323 | N | L | F | V | K | N | L | - | - | D | D | S | V | D | D | E | K | - | - | L | E | E | E | F | A | P | Y | G | T | I | I | T | S | A | K | V |
| YEAST SSB1#1 PARTIAL | 38 | T | I | F | I | G | N | V | - | A | H | E | C | T | E | D | D | L | K | Q | L | F | V | E | E | E | G | D | E | V | S | V | E | I | P | I |
| YEAST SSB1#2 | 202 | A | E | F | F | G | T | D | - | A | D | S | I | S | L | P | M | - | - | - | R | K | M | R | D | Q | H | T | G | R | I | F | - | - | - | - |
| FLY SEX-LETHAL#1 | 127 | N | L | I | V | N | Y | L | - | P | Q | D | M | T | D | R | D | - | - | - | V | Y | A | L | F | R | A | I | G | P | I | N | T | C | R | I |
| FLY SEX-LETHAL#2 | 214 | N | L | Y | V | T | N | L | - | P | R | T | I | T | D | D | Q | - | - | - | L | D | T | I | F | G | K | Y | G | S | I | V | Q | K | N | I |
| FLY TRANSFORMER-2 | 15 | G | V | F | G | L | N | T | N | T | S | Q | H | K | V | R | E | - | - | - | L | F | N | K | Y | G | P | I | E | R | I | Q | M | V | I | - |
| FLY HDP(P9)#1 | 32 | K | L | F | I | G | G | L | - | D | Y | R | T | T | D | E | N | - | - | - | L | K | A | H | F | E | K | W | G | N | I | V | D | V | V | V |
| FLY HDP(P9)#2 | 121 | K | L | F | V | G | A | L | - | K | D | D | - | H | D | E | Q | S | - | - | I | R | D | Y | F | Q | H | F | G | N | I | V | D | I | N | I |
| FLY ELAV#1 | 167 | S | L | F | S | S | V | G | E | I | E | S | V | K | - | - | - | L | - | - | I | R | D | K | S | Q | V | Y | I | D | P | L | N | P | Q | A |
| FLY ELAV#2 | 249 | N | L | Y | V | S | G | L | - | P | K | T | M | T | Q | Q | W | - | - | - | L | E | A | I | F | A | P | F | G | I | I | I | T | S | - | R | I |
| FLY ELAV#3 | 403 | P | I | F | I | Y | N | L | - | - | A | P | E | T | E | E | A | A | - | - | L | W | Q | L | F | G | P | F | G | A | V | Q | S | V | K | I |
| FLY BICOID | 387 | D | D | M | D | D | G | T | - | S | K | K | T | T | L | Q | I | L | E | P | L | KGLDK | S | C | D | D | G | S | S | D | DMSTG | I | I |
| HUMAN hnRNP-A1#1 | 15 | K | L | F | I | G | G | L | - | S | F | E | T | T | D | E | S | - | - | - | L | R | S | H | F | E | Q | W | G | T | L | T | D | C | V | V |
| HUMAN hnRNP-A1#2 | 106 | K | I | F | V | G | G | I | - | K | E | D | - | T | E | E | H | H | - | - | L | R | D | Y | F | E | Q | Y | G | K | I | E | V | I | E | I |
| -MOUSE HDP#1 | 15 | K | L | F | I | G | G | L | - | S | F | E | T | T | D | E | S | - | - | - | L | R | S | H | F | E | Q | W | G | T | L | T | D | C | V | V |
| -MOUSE HDP#2 | 106 | K | I | F | V | G | G | I | - | K | E | D | - | T | E | E | H | H | - | - | L | R | D | Y | F | E | Q | Y | G | K | I | E | V | I | E | I |
| -BOVINE UP1#1 | 15 | K | L | F | I | G | G | L | - | S | F | E | T | T | D | E | S | - | - | - | L | R | S | H | F | E | Q | W | G | T | L | T | D | C | V | V |
| -BOVINE UP1#2 | 106 | K | I | F | V | G | G | I | - | K | E | D | - | T | E | E | H | H | - | - | L | R | D | Y | F | E | Q | Y | G | K | I | E | V | I | E | I |
| HAMSTER NUCLEOLIN#1 | 312 | N | I | F | I | G | N | L | N | P | N | K | S | V | A | E | L | K | V | A | I | S | E | P | F | A | K | N | - | D | L | A | V | V | D | V |
| HAMSTER NUCLEOLIN#2 | 394 | T | L | L | A | K | N | L | - | S | F | N | I | T | E | D | E | - | - | - | L | K | E | V | F | E | D | A | L | E | I | R | L | V | S | - |
| HAMSTER NUCLEOLIN#3 | 486 | T | L | V | L | S | N | L | - | S | Y | S | A | T | E | E | T | - | - | - | L | Q | E | V | F | E | K | A | T | F | I | K | V | P | Q | - |
| HAMSTER NUCLEOLIN#4 | 579 | T | L | F | V | K | G | L | - | S | E | D | T | T | E | E | T | - | - | - | L | K | E | S | F | E | - | - | G | S | V | R | A | R | I | V |
| -MOUSE NUCLEOLIN#1 | 311 | N | L | F | I | G | N | L | N | P | N | K | S | V | N | E | L | K | F | A | I | S | E | L | F | A | K | N | - | D | L | A | V | V | D | V |
| -MOUSE NUCLEOLIN#2 | 396 | T | L | L | A | K | N | L | - | S | F | N | I | T | E | D | E | - | - | - | L | K | E | V | F | E | D | A | M | E | I | R | L | V | S | - |
| -MOUSE NUCLEOLIN#3 | 489 | T | L | V | L | S | N | L | - | S | Y | S | A | T | K | E | T | - | - | - | L | E | E | V | F | E | K | A | T | F | I | K | V | P | Q | - |
| -MOUSE NUCLEOLIN#4 | 571 | T | L | F | V | K | G | L | - | S | E | D | T | T | E | E | T | - | - | - | L | K | E | S | F | E | - | - | G | S | V | R | A | R | I | V |
| -XENOPUS NUCLEOLIN#1 | 109 | S | I | F | I | G | N | L | N | S | T | K | E | F | D | E | L | K | D | A | L | R | E | F | F | S | K | K | - | N | L | T | I | Q | D | I |
| -XENOPUS NUCLEOLIN#2 | 201 | T | L | F | V | K | N | I | - | P | Y | S | T | T | V | K | E | - | - | - | L | Q | E | I | F | E | N | A | K | D | I | R | I | P | T | G |
| -XENOPUS NUCLEOLIN#3 | 291 | V | L | V | V | N | N | L | - | S | Y | S | A | T | E | D | S | - | - | - | L | K | E | V | F | E | K | A | T | S | I | R | I | P | Q | V |
| -XENOPUS NUCLEOLIN#4 | 379 | T | L | F | V | R | G | L | - | S | E | D | T | T | E | E | T | - | - | - | L | K | E | A | F | D | - | - | G | S | V | N | A | R | I | V |

CONSENSUS: p a a a x N a - x p p x T a a x - - - a p a h F p a a G x a x x a x a
           o l r l    l     o o   c c           l o c o   o b r     l     l   l

Conserved Subdomains: I, II

FIG. 6A

```
                          + +    * * * * * * + *                      +
                V Y S K R S G K P R G Y A F I E Y E H E R D M H S A Y
                V YNKGSEG S G K P R G Y A F I E Y E H E R D M H A S Y
                I H D Q E S G K P K G Y A F I E Y E H E R D M H A A Y
                S - - - R S L K M R G Q A F V I F K E V S S A T N A L
                V P - - - - G - R H D I A F V E F D N E V Q A G A A R
                L - - - K T M K M R G Q A F V I F K E L G S S T N A L
                V P - - - - G - R H D I A F V E F E N D G Q A G A A R
                - - - - - - - - T H L F T F I Q F K K D L K - E S M K
                P M D N K T N K R R G F C F I T F N Q E E P
                - - - - - - - - H K G F A F V Q Y V N E R N A R A A V
                - - - - - - - - H K G F A F V Q F S N E R T A R T A V
                R R T L - H K A F K G S I F V V F D - - - S I E S A K
                R R T L - H K A F K G S I F A V F D - - - S I E S A K
                R R T L - Q R E F K G S I F I I F N - - - T D D D A K
                G D G V L E I L Q D G F G F L R S A D S S Y L - - A G
                P A A P E N E G - K V F K Y R F G K K I W D K I N A M
                C R D M I T R R S L G Y A Y V N F Q Q P A D A E R A L
                V C D E N - G S - K G Y G F V H F E T Q E A A E R A I
                M T D E S - G K S K G F G F V S F E R H E D A Q K A V
                M M E G - - G R S K G F G F V C F S S P E E A T K A V
                C R D A I T K T S L G Y A Y V N F N D H E A G R K A I
                A T D E N - G K S K G F G F V H F E E E G A A K E A I
                E K D A D - G K L K G F G F V N Y E K H E D A V K A V
                M R T E N - G K S K G F G F V C F S T P E E A T K A I
                K E H T D - G H - - - - - - - - - - - - - - - - - -
                - - - T S D S A N R G M A F V T F S G E N V D I E A K
                M R D Y K T G Y S F G Y A F V D F T S E M D S Q R A I
                L R D K L T G R P R G V A F V R Y N K R E E A Q E A I
                - - D A Q T Q R S R G F C F I Y F E K L S D A R A A K
                M K D P R T K R S R G F G F I T Y S H S S M I D E A Q
                V I D K E T G K K R G F A F V E F D D Y D P V D K V V
                P S K - - - G Q A L G Y G F V N Y V R P Q D A E Q A V
                Q N A G N D T Q T K G V G F I R F D K R E E A T R A I
                V K D P T T N Q C K G Y G F V S M T N Y D E A A M A I
                R A L A G T G - N R G A A F A K F G KPSPPQG P Q P P L
                M R D P N T K R S R G F G F V T Y A T V E E V D A A M
                M T D R G S G K K R G F A F V T F D D H D S V D K I V
                M R D P N T K R S R G F G F V T Y A T V E E V D A A M
                M T D R G S G K K R G F A F V T F D D H D S V D K I V
                M R D P N T K R S R G F G F V T Y A T V E E V D A A M
                M T D R G S G K K R G F A F V T F D D H D S V D K I V
                - - - - R T G T N R K F G Y V D F E S A E D L E K A L
                - - - - Q D G K S K G I A Y I E F K S E A D A E K N L
                - - - N Q Q G K S K G Y A F I E F A S F E D A K E A L
                - T D R E T G S S K G F G F V D F N S E E D A K A A K
                - - - - R T G T N R K F G Y V D F E S A E D L E K A L
                - - - - Q D G K S K G I A Y I E F K S E A D A E K N L
                - - - N P H G K P K G Y A F I E F A S F E D A K E A L
                - T D R E T G S S K G F G F V D F N S E E D A K A A K
                - - - - R I G N S K K F G Y V D F S S E E E V E K A L
                - - - - K D G S N K G I A Y V E F S N E D E A N K A L
                - - - N Q Q G R A K G F A F I F F S S A E D A K D A M
                - T D R D T G A S K G F G F V D F S T A E D A K A A K
                          + +    * * * * * * +                      +

M x D x  a  T G  b p b  a A  a p  a p a a a n p c   h
                       b       a o a  r G  l o  c o c c c p o h A o
                         40                50
```

FIG. 6B
⎱_____⎰
III

```
                  +       x x              + x             +          +
        - K H A D G K K I D G R R - V L V D V E R G R T    183
        - K H A D G K K I D S K R - V L V D V E R A R T    186
        - K H A D G K K I D S K R - V L V D V E R A R T    186
        - R S M Q G F P F Y D K P - M R I Q Y A K T D S     91
        - D A L Q G F K I T Q N N A M K I S F A K K        283
        - R Q L Q G F P F Y G K P - M R I Q Y A K T D S     88
        - D A L Q G F K I T P S H A M K I T Y A K K        225
        - C G M W G R A L R K A I - A D - W Y N E K G G    162
                                                          225
        - A G E D G R M I A G Q V - L D I N L A A E P K     89
        - A G E D G R M I A G Q V - L D I N L A A E P K     90
        - K F V E T P G Q K Y K E - T D L L I L F K D D    187
        - K F V E T P G Q K Y K D - T D L L I L F K E D    187
        - K F L E N R N L K Y K D - N D M T V L S R E E    187
        P D D I Y V S P S Q I R R - F N L R T G D T I S     98
        I A V D V E M G E T P V D - V T C P W E G A N F    173
        - D T M N F D V I K G K P - V R I M W S Q R D P     91
        - E K M N G M L L N D R K - V F V G R F K S R K    177
        - D E M N G K E L N G K Q - I Y Y V G R A Q K K V  267
        - T E M N G R I V A T K P - L Y V A L A Q R K E    369
        - E Q L N Y T P I K G R L - C R I M W S Q R D P    118
        - D A L N G M L L N G Q E - I Y V A P H L S R K    205
        - E A L N D S E L N G E K - L Y V G R A Q K K N    298
        - T E K N Q Q I V A G K P - L Y V A I A Q R K D    401
        - - - - - - - - - - - - - - - - - - - - - - -      78
        A E E F K G K - V F G D R E L T V D V A V I R P    275
        - K V L N G I T V R N K R - L K V S Y A R P G G    206
        - S A L N N V I P E G G S - Q P L S V R L A E E    292
        - D S C S G I E V D G R R - I R V D F S I T Q R     82
        - K S R P - H K I D G R V - V E P K R A V P R Q    108
        - L Q K Q - H Q L N G K M - V D V K K A L P K Q    197
        - N V L N G L R L Q N K T - I K V S F A R P S S    242
        - I A L N G T T P S S CTD P I V V K F S N T P G    331
        - R A L N G Y T M - G N R V L Q V S F K T N K A    482
        - - G M G G V A L - G E S - N Q Y Q C T M D T I    473
        - N A R - P H K V D G R V - V E P K R A V S R E     93
        - I Q K - Y H T V N G H N - C E V R K A L S K Q    184
        - N A R - P H K V D G R V - V E P K R A V S R E     93
        - I Q K - Y H T V N G H N - C E V R K A L S K Q    184
        - N A R - P H K V D G R V - V E P K R A V S R E     93
        - I Q K - Y H T V N G H N - C E V R K A L S K Q    184
        - - E L T G L K V F G N E - I K L E K P K P K G    385
        - E E K Q G A E I D G R S - V S L Y Y T G E K G    468
        - N S C N K M E I E G R T - I R L E L Q G P R G    561
        - E A M E D G E I D G N K - V T L D W A K P K G    648
        - - E L T G L K V F G N E - I K L E K D P K G R    387
        - E E K Q G A E I D G R S - V S L Y Y T G E K G    470
        - N S C N K M E I E G R T - I R L E L Q G S N S    464
        - E A M E D G E I D G N K - V T L D W A K P K G    646
        - K L T F K K I L G T E V - K I E K A M A F D K    186
        - E E K Q G A E I E G R S - I F V D F T G E K G    275
        - D S C N N T E I E G R S - I R L E F S Q G G G    367
        - E A M E D G E I D G N K - V T L D F A K P K G    455
                  +       x x              + x             +          +
        - a a h a         a a    b       n p a p         c
                   G x x      G    x -            x A x x    x
          c c a a         l b     a        p o l o            h
          60              70              80
                              IV
```

*FIG. 6C*

| Site | Do Bind to U1 RNA | Do Not Bind to U1 RNA |
|---|---|---|
| $F_{106}$ | Y<br>L, I, V | H, T |
| $Y_{146}$ | F | L, V<br>S, C |
| $F_{148}$ |  | Y<br>L, I, V<br>S, C |
| $Y_{151}$ | F | I, V |

RIBONUCLEOPROTEINS AND RNA-BINDING PROTEINS USEFUL FOR THE SPECIFIC RECOGNITION AND BINDING TO RNA, AND FOR CONTROL OF CELLULAR GENETIC PROCESSING AND EXPRESSION

This is a Division of application Ser. No. 08/173,941, filed on DEC. 27, 1993, now U.S. Pat. No. 5,561,222, which is a continuation application of Ser. No. 07/536,943, filed JUN. 12, 1990, abandoned, which is a continuation-in-part of application Ser. No. 07/436,779, filed on NOV. 15, 1989, abandoned.

The subject matter disclosed in this document is the product of work supported by the National Institutes of Health (Grant No. P01 CA 30246).

BACKGROUND OF THE INVENTION

1. Field of the Invention

This invention relates to ribonucleoproteins and to proteins which contain amino acid sequences that recognize specific RNA sequences.

2. Discussion of the Background

General features of primary sequence that characterize RNA- and DNA-binding proteins only recently have begun to become apparent. The helixturn-helix (Pabo et al, *Annu. Rev. Biochem.*, (1984) 53: 293–321) and zinc-binding finger (Evans et al, *Cell* 1988) 52: 1–3) arrangements have both been observed as structural features of sequence-specific DNA-binding proteins. However, the helix-turn-helix arrangement found in prokaryotes has not revealed a primary amino acid sequence motif with a recognizable pattern (Matthews, *Nature* (1988) 335: 294–295).

In eukaryotes, the homeobox domain seems to represent a widespread primary sequence motif for specific DNA-binding (Levine et al, *Cell* (1988) 55: 537–540; Robertson, *Nature* (1988) 336: 522–524, and references therein), and the members of the steroid hormone receptor superfamily of DNA-binding proteins utilize a common motif which forms zinc-binding fingers (Evans, *Science* (1988) 240: 889–895).

RNA-binding proteins have been less well studied than DNA-binding proteins. General features of RNA-binding proteins were not evident until the recognition of an amino acid octamer present in four proteins associated with mammalian nuclear RNAs (Adam et al, *Mol. Cell Biol.* (1986) 6: 2932–2943). Despite the finding of the octamer in additional RNA-associated proteins (Swanson et al, *Mol. Cell Biol.* (1987) 7: 1731–1739; Dreyfuss et al, *Trends Biochem. Sci.* (1988) 13: 86–91), there has been no evidence to date that these sequences are involved in binding to specific RNA sequences.

The specific recognition of RNA by proteins involves a variety of amino acid sequences that differ widely among the known RNA-binding proteins (reviewed in Schimmel, *Ann. Rev. Biochem.* (1987) 56:125–128; Ollis et al, *Chem. Rev.* (1987) 87:981–985; see also Wilson et al, *Proc. Nat. Acad. Sci.* (*USA*) (1986) 83:7251–7255; Strub et al, *Mol. Cell. Biol.* (1990) 10:777–784). One family of proteins involved in RNA processing has been identified that share a primary sequence motif of approximately 80 amino acids which the inventors have termed an RNA recognition motif (RRM) (for reviews see Mattaj, *Cell* (1989) 57:1–3; Bandziulis et al, *Genes Dev.* (1989) 3:431–437; Keene et al, "Nuclear RNA binding proteins. In Progress in Nucleic Acid Research and Molecular Biology," K. Moldave and W. Cohn, eds. Academic Press, Inc., Orlando, Fla., 1990). This motif contains the strongly conserved RNP octamer consensus sequence (Adams et al, *Mol. Cell Biol.* (1986) 6:2932–2943) and is present as single or multiple copies in a given protein. Specific RNA-binding domains have been defined for the U1 snRNP-70K and A proteins and the domain corresponds closely to the RRM in each protein (Ouery et al, *Cell* (1989) 57:89–101; Scherly et al, *Embo J.* (1989) 8:4163–4170). The role of specific sequence elements within the RRM in determining the RNA recognition properties of this family of proteins has not been determined, however.

The U1 and U2 snRNPs are components of the spliceosome which removes introns from pre-mRNAs (reviewed in Sharp, *Science* (1987) 235:766–771; Steitz et al, "Functions of the abundant U-snRNPs. In Structure and Function of Major and Minor Small Nuclear Ribonucleoprotein Particles," M. L. Birnstiel, ed. (Pringer-Verlag: Berlin), pp. 115–154 (1988)). The U1 snRNP recognizes pre-mRNAS in part through base pairing of U1 RNA with the 5' splice site (Zhuang et al, *Cell* (1986) 46:827–835), while the U2 snRNP recognizes the intron branch point in part through base pairing with the conserved branch point in part through base pairing with the conserved branch point sequence (Parker et al., *Cell* (1987) 49:229–239; Wu et al, *Genes Dev.* (1989) 3:1553–1561; Zhuang et al, *Genes Dev.* (1989) 3:1545–1552). In addition to the U snRNP-common Sm proteins, the U1 snRNP contains 3 unique proteins (70K, A, and C), while the U2 snRNP contains only 2 unique proteins (B" and A'). The U1 snRNP-A (A) and U2 snRNP-A' (A') proteins are unrelated in sequence but are so named because they migrate at similar positions in SDS-polyacrylamide gels (Pettersson et al., *J. Biol. Chem.* (1984) 259:5907–5914; Bringmann et al., *EMBO J.* (1986) 5:3509–3516). For clarity the designation $A^{prime}$ for A' protein will be used in this text.

The A (Sillekens et al., *EMBO J.* (1987) 6:3841–3848) and U2 snRNP-B" (B") (Habets et al., *Proc. Nat. Acad. Sci.* (*USA*), (1987) 84:2421–2425) proteins each contain two RRMs. The sequences within the corresponding motifs of these proteins are highly conserved (Sillekens et al., *EMBO J.* (1987) 6:3841–3484). Their amino-terminal RRMs are 75% identical and their carboxy-terminal RRMs are 86% identical. Despite the high degree of primary amino acid sequence similarity, these two proteins associate with different RNAs in vivo (reviewed in Zieve, "Cell Biology of the snRNP Particles. Critical Reviews in Biochemistry and Molecular Biology" 25:1–46 (1990)).

The recognition of RNA by proteins has appeared to the inventors to be a key reaction in the regulation of expression of the genetic material of all cells. In this context, however, prior to the present invention it was not known how those proteins could recognize a specific sequence of RNA. If such domains of theses proteins were found they would have many important applications, e.g., in the fields of the regulation of gene expression, RNA-protein interactions, autoimmune and neoplastic diseases, and developmental biology.

SUMMARY OF THE INVENTION

Accordingly, one object of this invention is to provide novel RNA-binding proteins and ribonucleoproteins.

It is another object of this invention to provide novel ribonucleo-proteins which can provide in vivo modulation of the expression of specific gene products in prokaryotic or eukaryotic cells as well as in vitro targeted reactions.

It is another object of this invention to provide modified ribonucleo-proteins which can be used in vivo to correct defects in genetic functions relating to RNA processing, expression and/or binding in prokaryotic or eukaryotic cells.

It is another object of this invention to provide novel ribonucleoproteins that can provide intracellular targeting or specific detection of the RNA component of the ribonucleoprotein.

Another object of this invention is to provide RNA-transactivating proteins which can be used for the regulation of pre-messenger RNA in eukaryotic cells.

The present invention which satisfies all of the above objects of the invention, and others as can be seen from the description of the invention given hereinbelow, provides proteins which relate to the one hundred twenty-five residue-long amino acid sequence of amino acids 92 to 216 of 70K U1 snRNP protein (see FIG. 2 for the complete sequence). These proteins have been discovered by the inventors to be capable of selectively binding to a unique thirty one to thirty three nucleotide-long sequence of U1 RNA (see FIG. 1 which sets out this U1 RNA sequence as stem (I) in the sequence given). The discovery of these and other binding elements provides novel ribonucleoproteins obtained by linking selected proteins to the 70K protein binding domain and selected RNA sequences to the U1 RNA binding domain. The present invention also provides peptides and proteins which relate to the thirteen residue-long amino acid sequence of amino acids 128 to 140 of 70K U1 snRNP protein, and to peptides and proteins which relate to the eight residue-long amino acid sequence of amino acids 133 to 140 of 70K U1 snRNP protein.

BRIEF DESCRIPTION OF THE FIGURES

A more complete appreciation of the invention and many of the attendant advantages thereof will be readily obtained as the same becomes better understood by reference to the following detailed description when considered in connection with the accompanying figures.

FIG. 2 provides the complete sequence of human 70K U1 snRNP protein, its U1 RNA binding domain (positions 92 to 202/shaded box) and its RNA recognition motif (position 104 to 183/darker shading within the box).

FIG. 6 shows regions of sequence similarity among several RNA-associated proteins and the U1 RNA binding domain of the 70K protein.

FIG. 7 provides a summary of the effect of mutations in the 70K protein aromatic positions relative to U1 RNA binding activity for the protein.

FIGS. 11A, 11B and 11C show that a change of 5 amino acids in the U1 snRNP-A protein allows it to bind to U2 RNA. (A) Summary of the site-directed mutants that progressively convert the U1 snRNP-A-protein into the U2 snRNP-B" protein. The first and last sequences in the table shows the amino-terminal RRM of the U1 snRNP-A and U2 snRNP-B" proteins as taken from Query et al (1989). The boxes in these two sequences enclose amino acids which are not identical. Between A and B" are shown the sequences of the amino terminal RRMs of each of the A/B" conversion mutants. Each mutant contains the wild-type A sequence except at the boxed positions, where the sequence has been converted to that of B". The numbered blocks at the bottom of the table indicate groups of amino acids converted as a block to the B" sequence. Block 1 corresponds to variable region-1 of the RRM. Block 6 is now shown; it changed amino acids 1–6 of A (MAVPET) to amino acids 1–3 of B" (MDI). The shaded regions indicate positions that are generally conserved in a large number of RRM-containing proteins, and a consensus is shown at the bottom. The columns on the left of the table summarize the results of RNA binding assays. The ability of a mutant to bind to full-length U1 or U2 RNAs is indicated by a (+) or (−) in the appropriate column. Blank positions indicate mutants not directly tested for U1 or U2 RNA binding; these were tested only for their ability to co-precipitate U2 RNA in the presence of $A^{prime}$ (see FIG. 13A). (B) Mobility shift assays of B", A, and the pentamer mutant A/B".1A. $^{35}$S-labeled in vitro translated polypeptides representing B" amino acids 1–109 (lanes 1–5), A amino acids 1–119 (lanes 6–10), or A/B".1A amino acids 1–119 (lanes 11–15) were incubated with 1.5 μg of the indicated in vitro transcribed RNAs and assayed for specific complex formation on a nondenaturing polyacrylamide gel: Lanes 1, 6 and 11, no additional RNA (tRNA only); lanes 2, 7, and 12, full-length U1 RNA; lanes 3, 8, and 13, full-length U2 RNA; lanes 4, 9, and 14, U5 RNA; lanes 5, 10, and 15, β-globin RNA. (C) Mobility shift assays of selected A/B" conversion mutants were performed as in (B). The $^{35}$S-labeled in vitro translated polypeptides represented amino acids 1–142 of the constructs indicated above each panel. The RNAs added to each lane are indicated above each lane and are identical to those in (B). Lanes 1–12 show all mutants which formed a complex with U2 RNA; lanes 13–27 show representative examples of those which did not detectably bind U2 under these assay conditions. The results of all the mutants tested are summarized in panel (A).

DETAILED DESCRIPTION OF THE PREFERRED EMBODIMENTS

Figure 1:
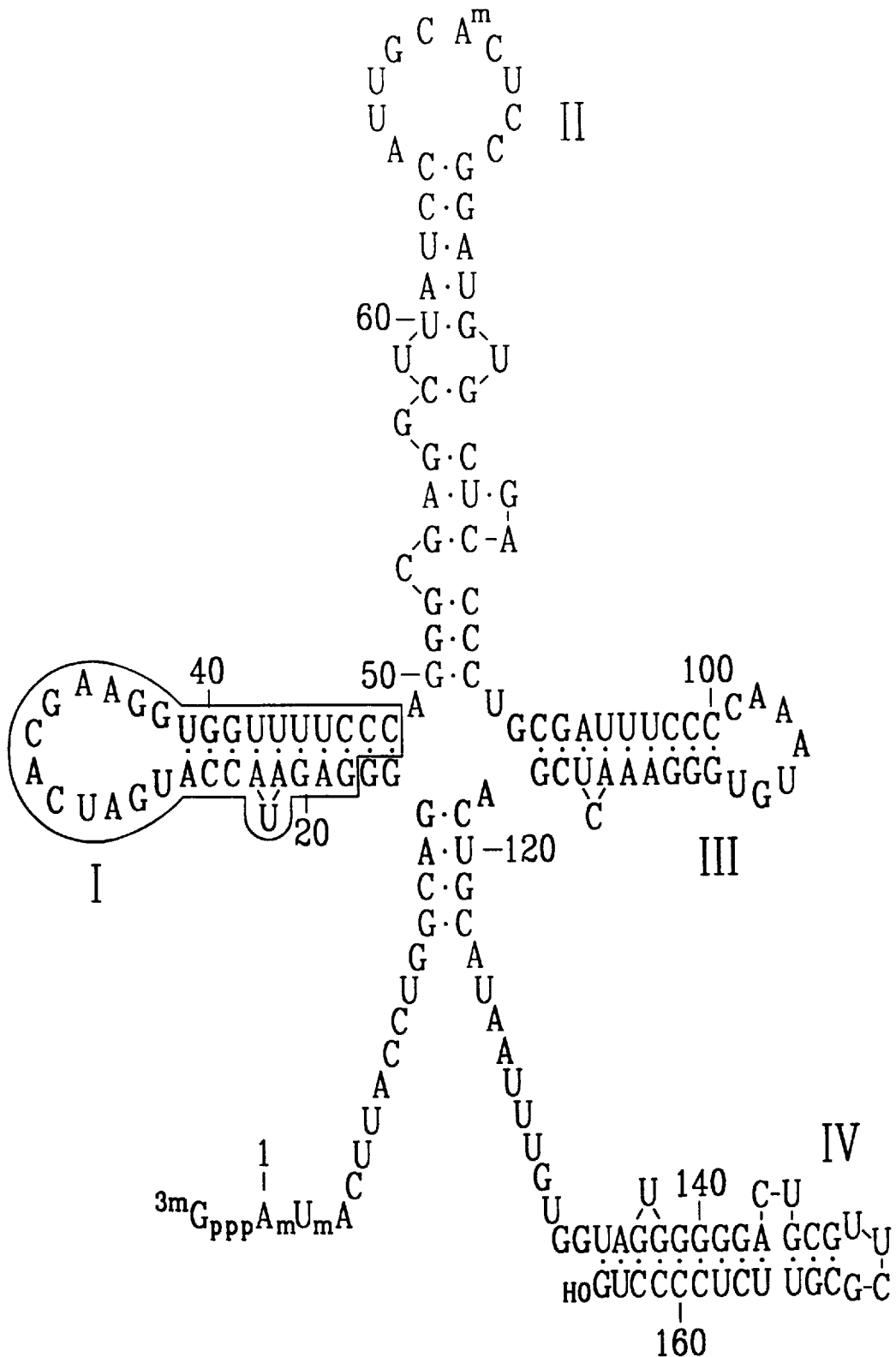
FIG. 1 sets out the nucleotide sequence and secondary structure of human U1 RNA (Branlant et al, *Nucleic Acids Res.* (1981) 9: 841–858; Mount and Steitz, *Nucleic Acids Res.*, (1981) 9: 6351–6368), showing the 70K protein binding site as stem-loop (I).

In this text, the following standard nomenclature is used.

TABLE 1

| Amino acid symbols. | | |
|---|---|---|
| Amino acid | Three-letter symbol | One-letter symbol |
| Alanine | Ala | A |
| Arginine | Arg | R |
| Asparagine | Asn | N |
| Aspartic acid | Asp | D |
| Asn + Asp | Asx | B |
| Cysteine | Cys | C |
| Glutamine | Gln | Q |
| Glutamic acid | Glu | E |
| Gln + Glu | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

In studying the RNA-binding properties of the U1 RNA-associated 70K protein to elucidate regions of RNA-protein interaction the inventors have identified a central amino acid sequence involved in the specificity of gene expression at the level of pre-messenger RNA splicing in cells. While several structural motifs of proteins important in sequence-specific DNA-binding have been identified (e.g., helix-turn-helix and zinc-binding fingers) and two primary sequence motifs recently have been implicated directly in DNA-binding (homeoboxes and sequences within the steroid receptor family which form zinc-binding fingers), the structure or primary sequences of RNA-binding domains were not known prior to this invention.

RNA is structurally distinct from DNA. Thus, there is no reason to believe that the protein binding properties of these two materials would have any similarities. RNA is complexly folded with topological conformations as well as linear base sequences (primary sequence). RNA resembles proteins in this aspect more than it resembles DNA.

Many RNA and protein species have known higher-order structural properties, but common features involved in their interactions were poorley understood prior to the present invention. Prior to this invention it was also not known whether elements controlling RNA binding were linked continuously on a protein or whether, instead, discontinuous elements involving long range interactions and folding of the protein were necessary.

For example, it was possible that elements for general recognition of RNA resided in one portion of a molecule and the elements controlling recognition of specific RNA sequences resided elsewhere, perhaps at a long distance away from the general recognition elements in the protein. The present discovery of a continuous segment of 70K protein (70K RNA binding domain) that contains both the specific recognition and binding properties for stem-loop (I) of U1 RNA (U1 RNA binding site) had not been known to be a characteristic of proteins for the recognition of RNA.

We have studied RNA binding proteins of this group (FIG. 6) for many years and in 1983 isolated the first eukaryotic recombinant cDNA member of this family of proteins that encodes the human La RNA binding protein (Chambers et al, Proc. Natl. Acad. Sci. (USA) (1985) 82: 2115–2119; Chambers et al, J. Biol. Chem. (1988) 263: 18043–18051). The observation by Dreyfuss and coworkers (Adam et al, Mol. Cell. Biol. (1986) 6: 2932–2943; Swanson et al, Mol. Cell. Biol. (1987) 1: 1731–1739) of an "RNP consensus" octamer in several eukaryotic proteins associated with RNA was an early indication that an amino acid sequence common among some RNA-binding proteins might exist.

Other publications by the Dreyfuss group (Dreyfuss et al, TIBS (1988) 13: 86–91) and from many other laboratories (Amrein et al, Cell (1988) 55, 1025–1035; Bell et al, Cell (1988) 55, 1037–1046; Bugler et al, J. Biol. Chem. (1987) 262: 10922–10925; Chambers et al (1988), ibid; Deutscher et al, Proc. Natl. Acad. Sci. (USA) (1988) 85: 9479–9483; Goralski et al, Cell (1989) 56, 1101–1108; Keene, J. D., J. Autoimmunity (1989) 2: 329–337; Merrill et al, J. Biol. Chem. (1988) 263, 3307–3313; Sachs et al, Mol. Cell. Biol. (1986) 7, 3268–3276) noted the presence of related sequences surrounding the octamer and some of them speculated that these regions might participate in RNA binding. It was not known however whether these sequences might endow specific as opposed to nonspecific recognition of RNA of if discontinuous regions involving long-range interactions within these proteins might be required for RNA binding.

Some authors speculated that the octamer and its surrounding residues constituted an RNA binding domain and Dreyfuss and coauthors (ibid) chose an arbitrary size of 100 amino acids. Their theory was based upon the occurrence of similar sequences in a set of proteins that were all thought to be associated with RNA. Evidence for direct binding of such regions to specific RNA sequences was not available and no domains of proteins with sequence-specific RNA binding activity were defined experimentally.

Included in this theory was the suggestion that the 70K U1 snRNP protein contained an RNA binding domain of 93 amino acids from positions 94 to 186. Other investigators (Theissen et al, EMBO J. (1986) 5: 3209–3217) had speculated that a different region of the 70K U1 snRNP protein encompassing amino acid residues 241 to 437 as well as the same region speculated by Dreyfuss were either one or both involved in RNA binding. These speculations were based upon the relationship of the highly basic (positively charged) region at amino acids 241 to 437 of 70K protein to regions of other proteins (e.g., protamines and histones) known to bind nucleic acid. No experimental evidence was available to support these suggestions.

Although the 70K protein is one of ten proteins known to be associated with the U1 snRNP complex (Pettersson et al, J. Biol. Chem. (1984) 59: 5907–5914), there was no evidence of specific RNA-protein contact between the 70K protein and any RNA species until the present discovery of a specific binding of the 70K protein to U1 RNA.

Furthermore, of the other members of this group of proteins (shown in FIG. 6) studied in our laboratory, as well as, in many other laboratories, none was shown to directly bind to a specific RNA sequence until the inventors discovered the sequence-specific interaction between 70K U1 snRNP protein and U1 RNA.

The region of the protein involved in this specific binding involves a different amino acid sequence of 70K protein than that speculated by Theissen et al or by Dreyfuss et al. In fact, one of the sequences proposed by Theissen as being responsible for RNA binding actually interferes with the detection of specific binding activity (as demonstrated in FIG. 3).

In addition, the present discovery of the precise RNA binding domain (FIG. 2) includes additional important amino acid sequences not previously recognized by the theory of Dreyfuss et al, by the published work of other workers mentioned above or by the inventors themselves in their earlier studies of La (Chambers et al, ibid) and the 60 kD Ro (Deutscher et al, ibid) protein members of the group.

We had performed direct RNA binding studies with the La (Chambers et al, ibid) and 60 kD Ro (Deutscher et al, ibid) RNA binding proteins, but had not identified a specific or discrete RNA binding domain of either protein. Through progressive deletion analysis of the 70K U1 snRNP protein (illustrated in FIG. 4), we found that U1 RNA is specifically recognized and stably bound by a particular region of the 70K protein as well as by larger sequences that contain this region (FIG. 2).

Based upon the functional test of specific RNA-binding activity, we defined a distinct and independent domain of the 70K protein. Furthermore, 23 discovered that the protein binding domain directly recognizes with high specificity a unique 31 to 33 nucleotide stem-loop structure on U1 RNA (stem-loop 1; see FIG. 1). The discovery of this specific binding reaction provided novel ribonucleoproteins by the attachment of other peptides to the 70K protein binding domain and other RNAs to the U1 RNA binding domain.

Thus, through progressive deletion analysis of the 70K U1 snRNP protein (illustrated in FIG. 4), we have found that U1 RNA is specifically recognized and stably bound by a particular region of the 70K protein as well as by larger sequences containing this region (shown in FIG. 2). Based upon the functional test of specific RNA-binding activity, we define this 125 amino acid-long region as a distinct and independent domain of the 70K protein.

Furthermore, we have discovered that the protein binding domain of 125 amino acids recognizes with high specificity a unique 31 to 33 nucleotide stem-loop structure on U1 RNA (stem-loop (I)—see FIG. 1).

Description of the Protein:

The complete sequence of human 70K U1 snRNP protein, amino acid residue nos. 1 to 437, is provided in FIG. 2. The present invention is based in part on the inventors' discovery that, apparently due to a high incidence of arginine residues therein, the region of human 70K U1 snRNP protein ranging from approximately amino acid 241 to 437 is responsible for binding of human 70K U1 snRNP protein to various materials other than U1 RNA.

Figure 3A:
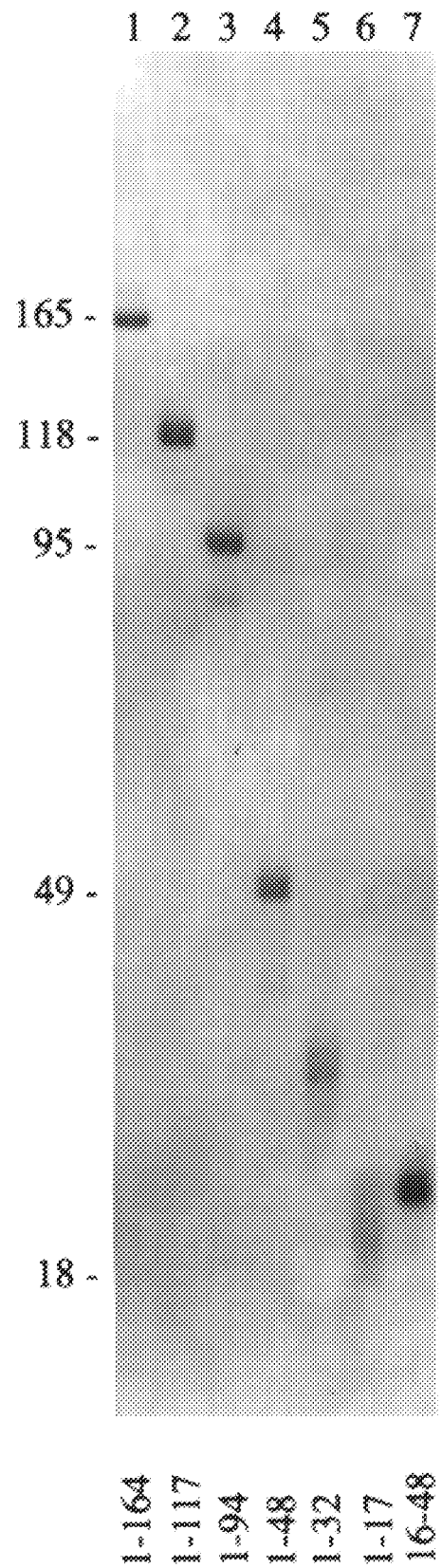
FIGS. 3a to 3g show 70K-lac Z fusion protein binding to various RNAS. The non-specific binding of the native protein to RNA species other than U1 RNA is associated with amino acid sequence 241 to 437 (in particular the sections underlined in FIG. 2).
Figure 3B:
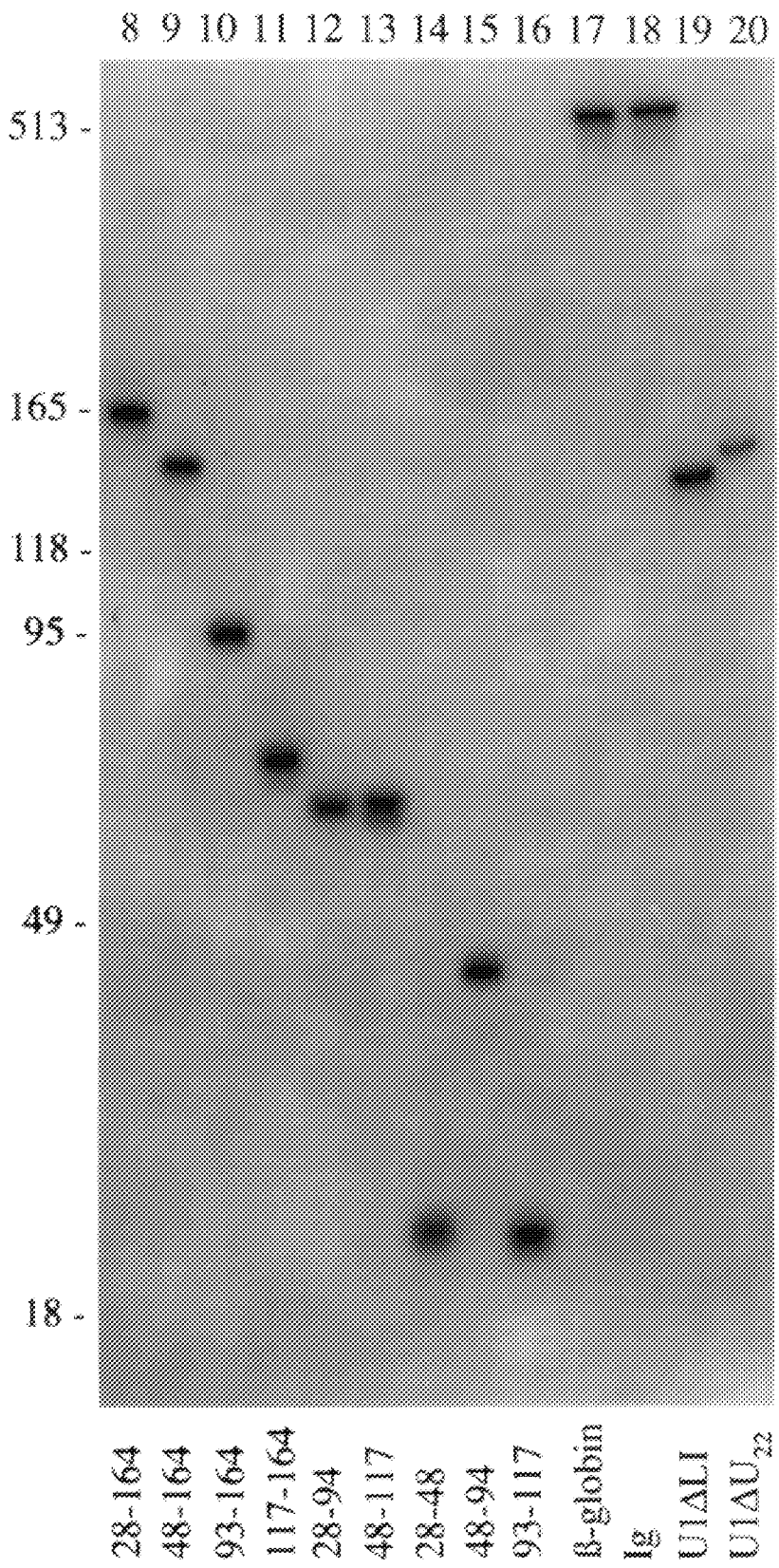
Figure 3C:
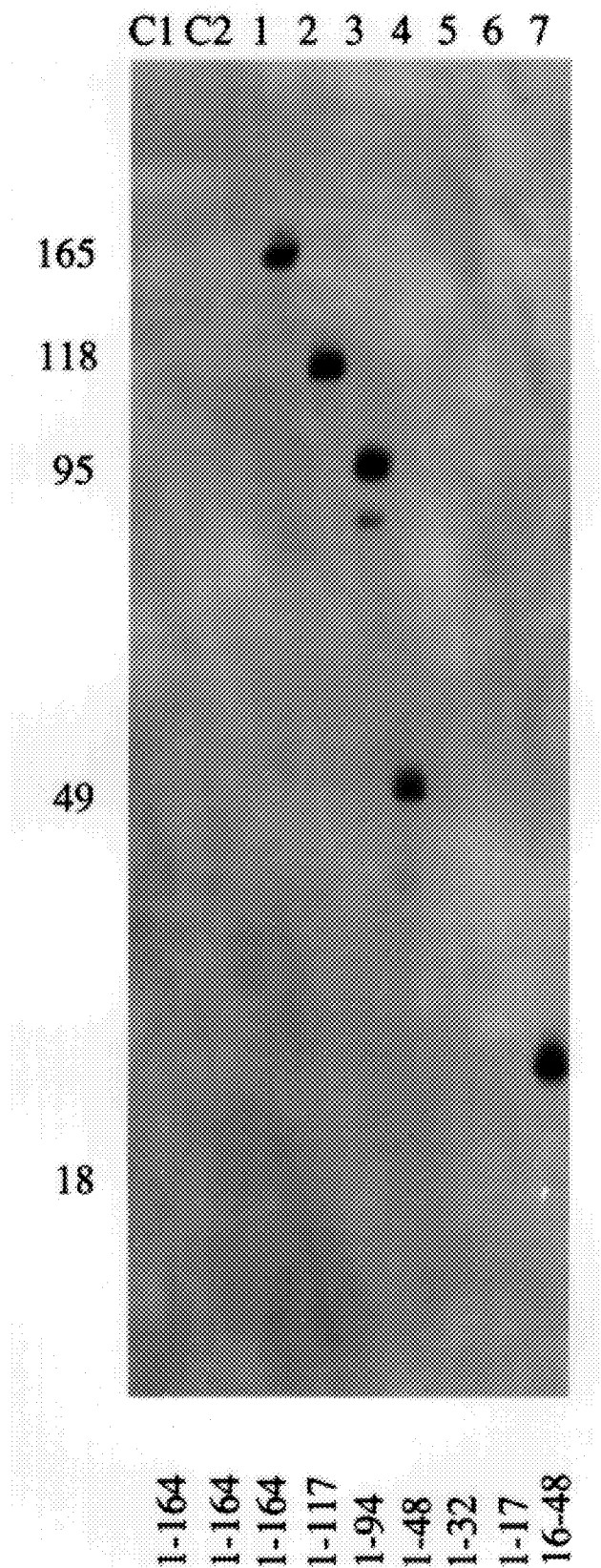
Figure 3D:
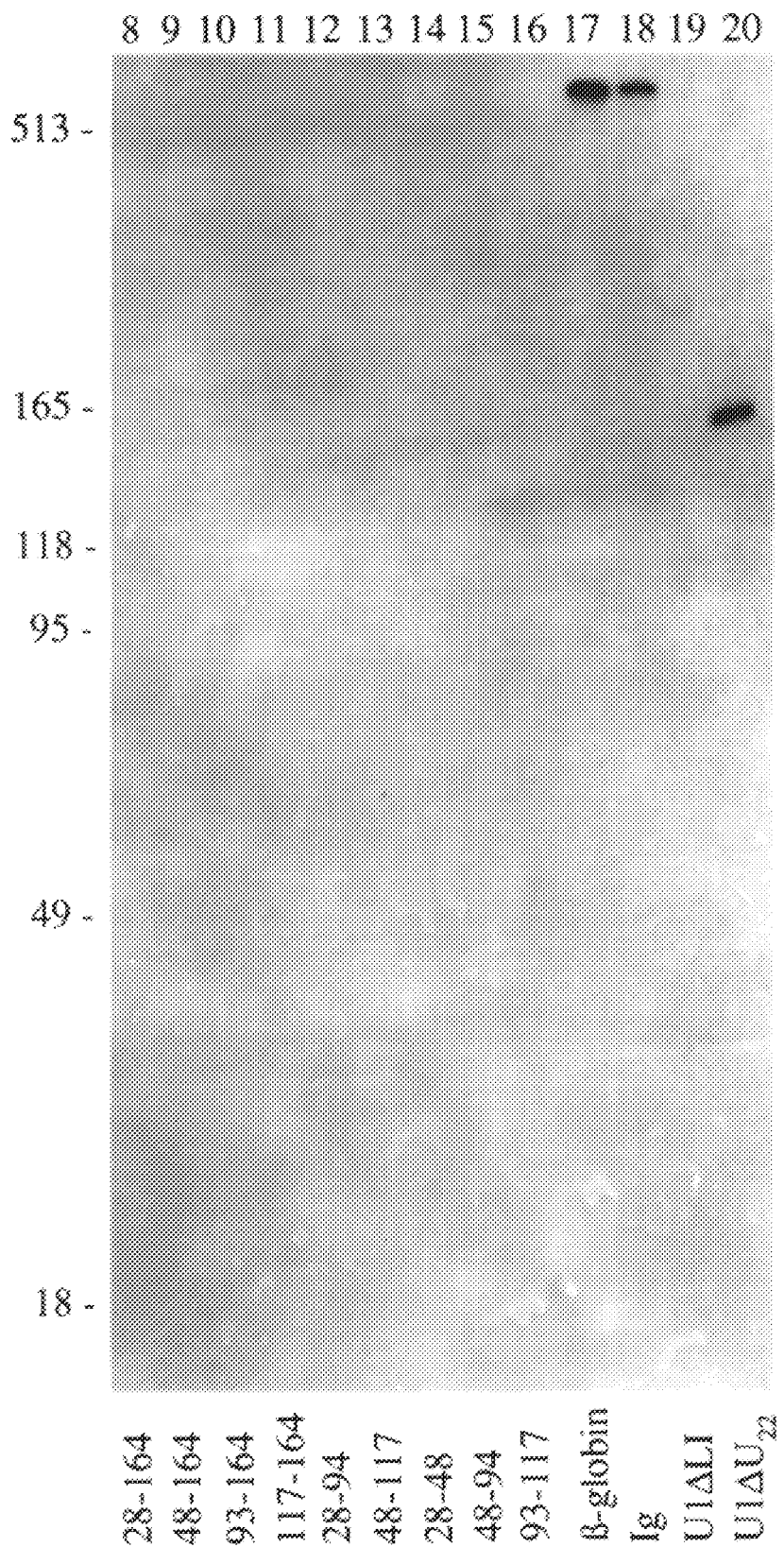
Figure 3E:
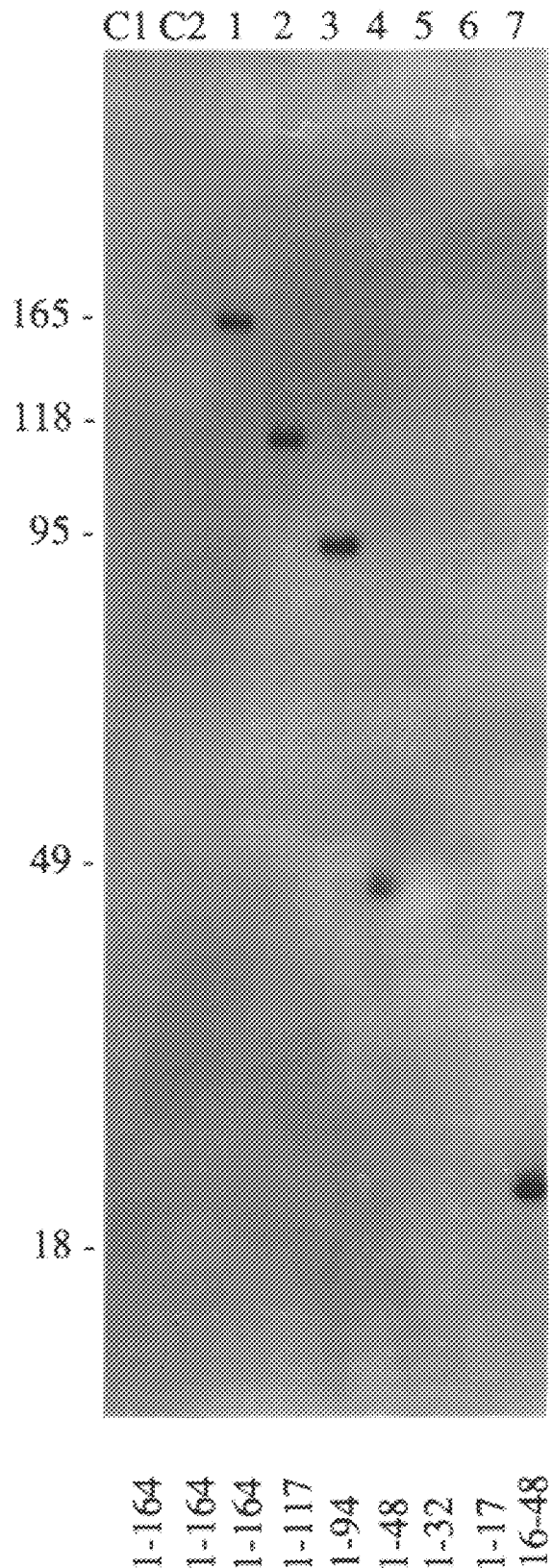
Figure 3F:
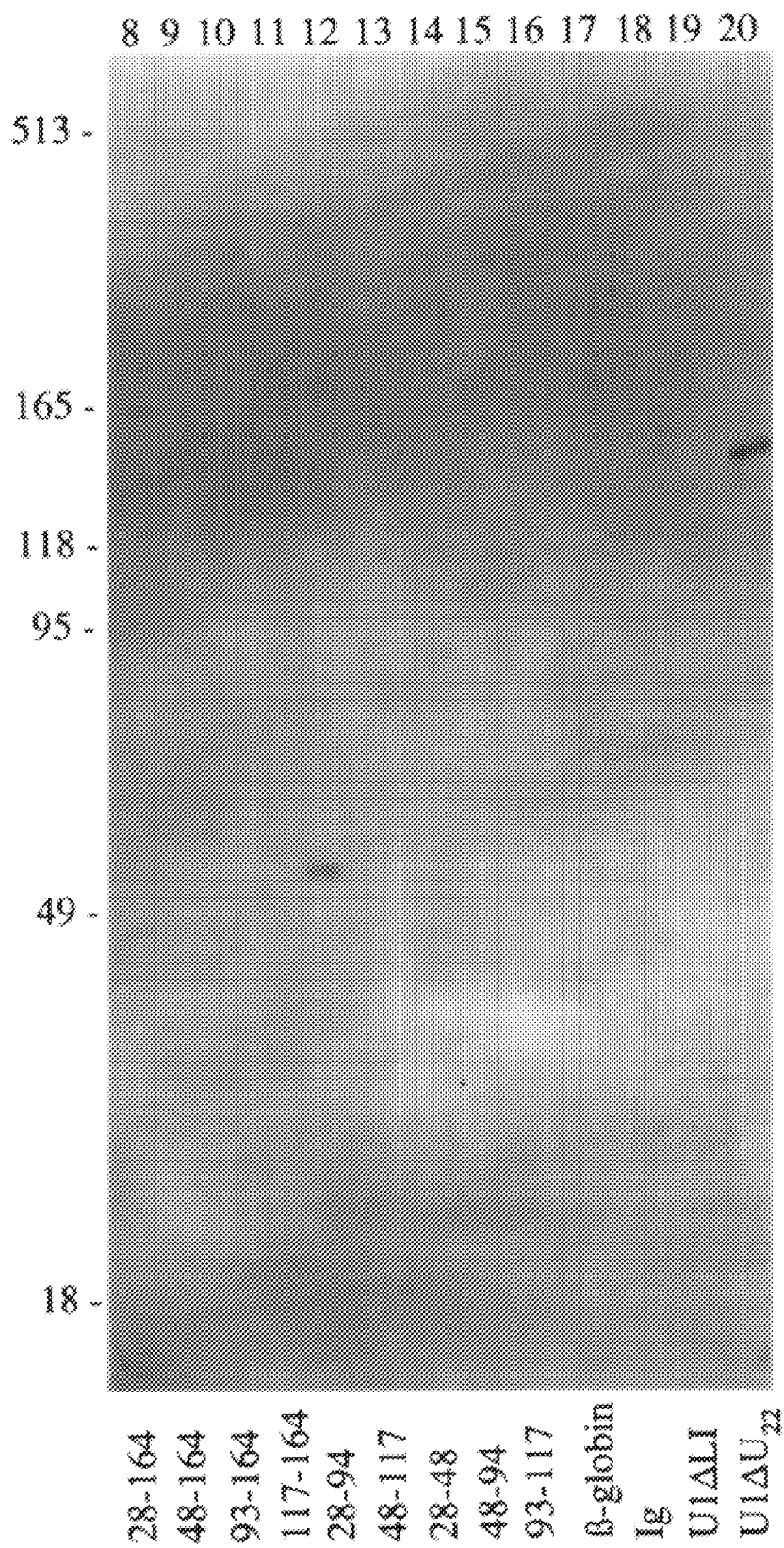
Figure 3G:
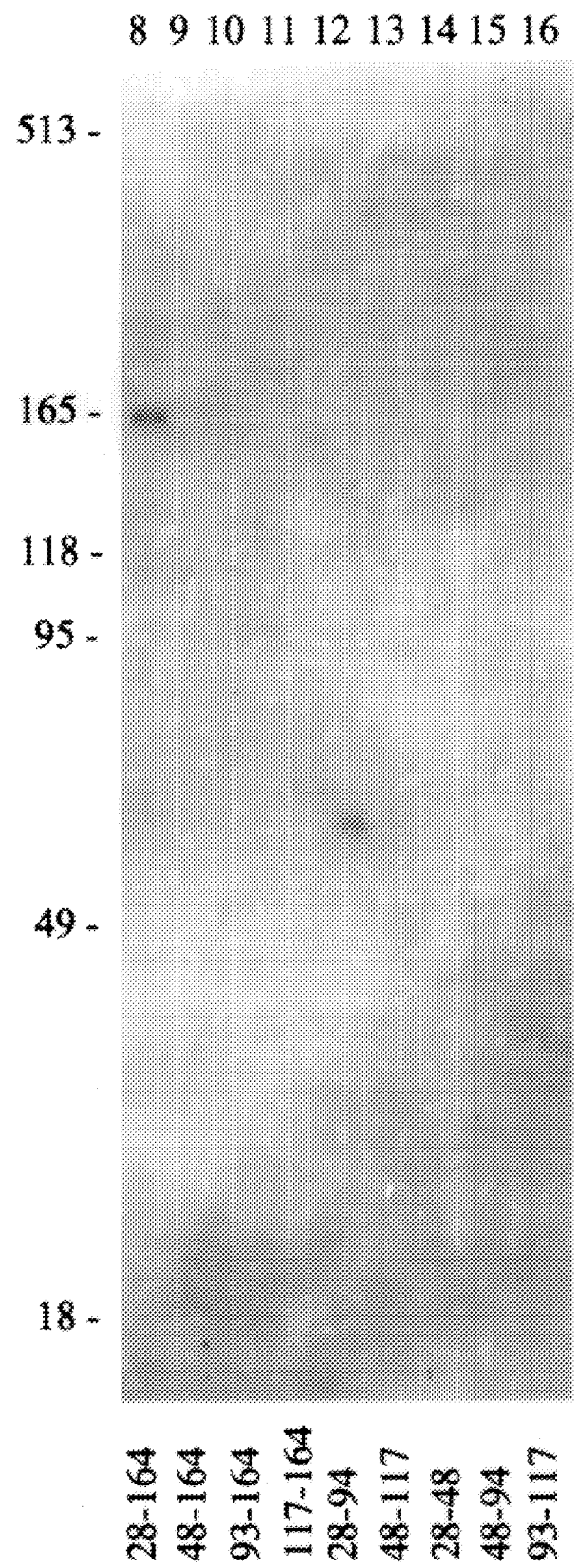

The presence of the amino acid sequence from position 241 to 437, and particularly the sequence underlined in FIG. 2, actually obscures the specificity of the protein towards specific binding of the 70K protein to the binding site of U1 RNA (shown approximately as stem-loop I in FIG. 1; roughly corresponding to nucleotides 18 to 48 in the sequence given). This is shown in FIG. 3d lanes 17 and 18 where two in vitro RNA transcripts representing unprocessed messenger RNAs can bind to the 70K fusion protein containing sequences 241 to 437. Removal of the region 217 to 437 (FIG. 3f lanes 17 and 18) results in binding to only U1 RNA transcripts. The present invention is thus concerned with proteins corresponding to amino acid residues 1 to 240 of 70K U1 snRNP protein.

Figure 4:
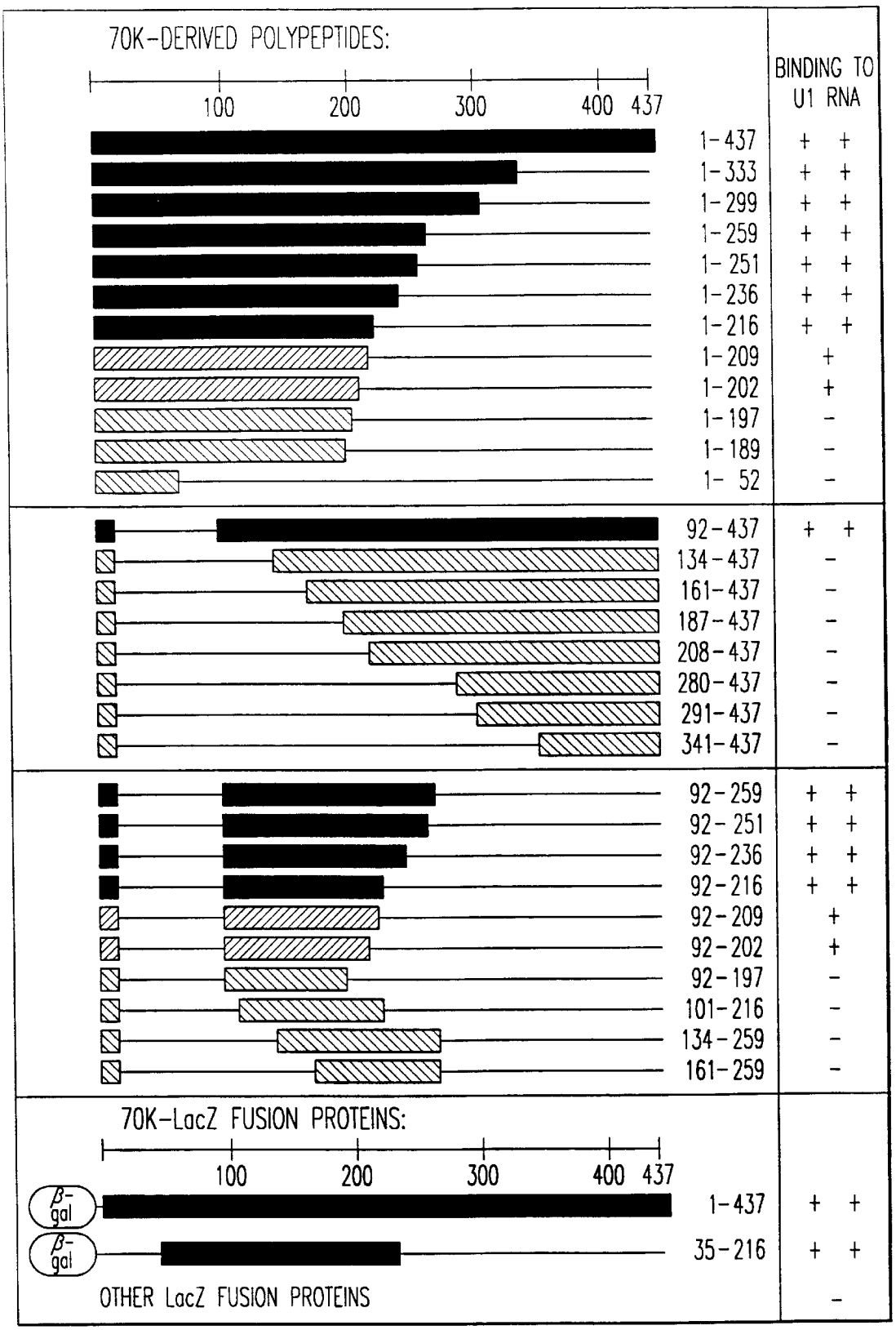
FIG. 4 provides a summary of various 70K protein-derived deletion constructs, providing their respective ability to bind to U1 RNA at its 70K protein binding site.

FIG. 4 sets out the relative abilities of various 70K U1 snRNP protein-derived deletion constructs to bind specifically to site (I) of U1 RNA. In this figure the narrow solid lines indicate deleted regions. The numbers indicating the amino acid sequence of the various constructs of 70K U1 snRNP are indicated in the right hand column.

The black boxes represent protein constructs that were found to bind to U1 RNA. These are given a U1 RNA binding rating of (++) or (+) in the right hand column. A rating of (++) indicates a deletion construct having an ability to bind to U1 RNA comparable to that of human 70K U1 snRNP protein. The designation of (+) designates a deletion construct that was found to bind U1 RNA specifically, but with reduced efficiency. Lightly shaded boxes represent protein constructs that did not detectably bind to U1 RNA. These are given a U1 RNA binding rating of (−) in the right hand column.

Figures 5A, 5B, 5C, 5D, 5E, 5F:
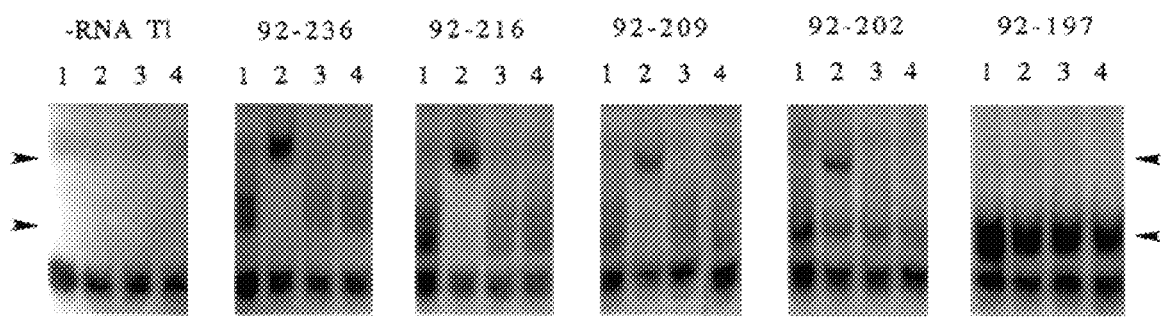
FIG. 5 is a mobility shift assay of the 70K RNA binding domain of the 70K U1 snRNP protein when complexed with the specific site of binding on U1 RNA.

These ratings can be obtained experimentally as follows. For example, in FIG. 5, lanes 2 demonstrate differing binding affinities of 70K constructs to U1 RNA. Constructs in panels B and C bind with full affinity (++), as evidenced by all the 70K protein being complexed with U1 RNA (upper arrow). Constructs in panels D and E bind with reduced affinity (+), as evidenced by only 30 to 70% of the 70K protein present being complexed with U1 RNA and the remainder migrating separately (upper and lower arrows, respectively). Although the latter constructs have a reduced affinity for binding to U1 RNA, they retain their specificity for U1 RNA, as evidenced by the lack of complex formation with other RNAs (panels D and E, lanes 1, 3, and 4). The 70K construct in panel F does not bind to U1 RNA (−), as evidenced by all the 70K protein migrating at the position of the lower arrow.

FIG. 4 shows that the smallest domain capable of detectable specific binding to U1 RNA corresponds to a peptide made up of residues 92 to 202 of the 70K protein. FIG. 4 also shows that the section of human 70K U1 snRNP protein corresponding from approximately residue 241 to residue 437 does not contribute to the native protein's ability to specifically bind U1 RNA. This sequence instead contributes to non-specific binding by the protein. This observation does not support the suggestion by Theissen et al, supra, that this portion of human 70K U1 snRNP protein may be involved in specific binding to U1 RNA.

Thus in one embodiment, this invention provides a U1 RNA binding protein having an amino acid sequence corresponding to that of residues 92 to 202 (sequence (I)), preferably 92 to 216 (sequence (II)), of the 70K U1 snRNA binding protein. These sequences of the 70K U1 RNA binding protein are set out below.

Sequence (I):

```
            100            110
H N D P N A Q G D A F K T L F V A R V N Y D T T E S K L
120           130           140
R R E F E V Y G P I K R I H M V Y S K R S G K P R G Y A
   150           160           170
F I E Y E H E R D M H S A Y K H A D G K K I D G R R V L
     180           190           200
V D V E R G R T V K G W R P R R L G G G L G G T R R G
```

Sequence (II):

```
            100            110
H N D P N A Q G D A F K T L F V A R V N Y D T T E S K L
120           130           140
R R E F E V Y G P I K R I H M V Y S K R S G K P R G Y A
   150           160           170
F I E Y E H E R D M H S A Y K H A D G K K I D G R R V L
     180           190           200
V D V E R G R T V K G W R P R R L G G G L G G T R R G G
         210
A D V N I R H S G R D D T
```

In another embodiment, in light of the inventors' discovery that the section of 70K U1 snRNP protein corresponding approximately to amino acids 241 to 437 contributes to non-specific binding, the present invention provides a protein comprising, as a core component, a component corresponding to residues 92 to 202 of human 70K U1 snRNP protein (sequence (I)) to which is attached, independently at either corresponding end, a further sequence of amino acids corresponding to, respectively, at least part of residues 1 to 91 and residues 203 to 240 of human 70K U1 snRNP protein. This variable sequence thus corresponds to at least sequence (I) and up to sequence (III).

Sequence (III) is set out below.

Sequence (III):

```
            10            20
M T Q F L P P N L L A L F A P R D P I P Y L P P L E K L P
30           40           50
H E K H H N Q P Y C G I A P Y I R E F E D P R D A P P P T
   60           70           80
R A E T R E E R M E R K R R E K I E R R Q Q E V E T E L K
     90           100           110
M W D P H N D P N A Q G D A F K T L F V A R V N Y D T T E
       120           130           140
S K L R R E F E V Y G P I K R I H M V Y S K R S G K P R G
         150           160           170
Y A F I E Y E H E R D M H S A Y K H A D G K K I D G R R V
           180           190           200
L V D V E R G R T V K G W R P R R L G G G L G G T R R G G
             210           220           230
A D V N I R H S G R D D T S R Y D E R P G P G P S P L P H
               240
R D R D R D R E R E
```

Amino acids 1 to 91 and 203 to 240 represent groups in sequence (III) which may be varied by sequentially removing as many residues as desired from each end, beginning, respectively, from residues nos. 1 and 240. Thus, this embodiment provides a protein having an amino acid sequence corresponding at least to residues 92 to 202 and up to about residues 1 to about 240 of sequence (III).

FIG. 6 sets out regions of sequence homology (similarity) among several RNA-associated proteins and the U1 RNA binding domain of the 70K protein. The regions are arranged to create the best alignment of conserved residues within subdomains of the 80 amino acid region. The starting residue number and the ending residue number for each of the specific proteins whose partial sequences are provided in FIG. 6 are given at each end of the sequences shown.

In another embodiment, the present invention thus provides proteins having at least 35% homology with sequences (I), (II) and (III) and which are capable of binding RNA. The amino acid sequences of illustrative proteins provided in this embodiment correspond to a core component provided in FIG. 6, having at each end at least 10 amino acids, and preferably 20 amino acids, corresponding to the amino acids found in the corresponding native protein.

This embodiment thus provides proteins which have an amino acid sequence region that comprise the consensus sequence in FIG. 6 at positions 2–4, 7, 14, 15, 17, 18, 21, 22, 24, 25, 27, 32, 39, 40, 42–49, 58, 63, 67, 69, 72, 74, 77 and 80 in the consensus sequence. The proteins have variable-length insertions and/or deletions of amino acid residues between positions 8 to 9, 15 to 17, 28 to 41, 51 to 57, 59 to 60, 67 to 68, and 71 to 72, inclusive.

In the sequences given in FIG. 6, position 1 of the consensus sequence is defined as the left-hand most amino acid in the sequences given, no matter the protein. Position 81 of the consensus sequence is the right-hand most amino acid in the sequences given in FIG. 6.

The proteins in this embodiment comprise proteins having at least 48 amino acid residues and an amino acid sequence comprised within the sequence of formula (IV).

Formula (IV):

$$(aa)_1\text{-}(aa)_2\text{-}(aa)_3\text{-}(aa)_4\text{-}(aa)_5\text{-}(aa)_6\text{-}(aa)_7\text{-}(aa)_8\text{-}$$
$$(aa)_9\text{-}(aa)_{10}\text{-}(aa)_{11}\text{-}(aa)_{12}\text{-}(aa)_{13}\text{-}(aa)_{14}\text{-}(aa)_{15}\text{-}$$
$$(aa)_{16}\text{-}(aa)_{17}\text{-}(aa)_{18}\text{-}(aa)_{19}\text{-}(aa)_{20}\text{-}(aa)_{21}\text{-}(aa)_{22}\text{-}$$
$$(aa)_{23}\text{-}(aa)_{24}\text{-}(aa)_{25}\text{-}(aa)_{26}\text{-}(aa)_{27}\text{-}(aa)_{28}\text{-}(aa)_{29}\text{-}$$
$$(aa)_{30}\text{-}(aa)_{31}\text{-}(aa)_{32}\text{-}(aa)_{33}\text{-}(aa)_{34}\text{-}(aa)_{35}\text{-}(aa)_{36}\text{-}$$
$$(aa)_{37}\text{-}(aa)_{38}\text{-}(aa)_{39}\text{-}(aa)_{40}\text{-}(aa)_{41}\text{-}(aa)_{42}\text{-}(aa)_{43}\text{-}$$
$$(aa)_{44}\text{-}(aa)_{45}\text{-}(aa)_{46}\text{-}(aa)_{47}\text{-}(aa)_{48}\text{-}(aa)_{49}\text{-}(aa)_{50}\text{-}$$
$$(aa)_{51}\text{-}(aa)_{52}\text{-}(aa)_{53}\text{-}(aa)_{54}\text{-}(aa)_{55}\text{-}(aa)_{56}\text{-}(aa)_{57}\text{-}$$
$$(aa)_{58}\text{-}(aa)_{59}\text{-}(aa)_{60}\text{-}(aa)_{61}\text{-}(aa)_{62}\text{-}(aa)_{63}\text{-}(aa)_{64}\text{-}$$
$$(aa)_{65}\text{-}(aa)_{66}\text{-}(aa)_{67}\text{-}(aa)_{68}\text{-}(aa)_{69}\text{-}(aa)_{70}\text{-}(aa)_{71}\text{-}$$
$$(aa)_{72}\text{-}(aa)_{73}\text{-}(aa)_{74}\text{-}(aa)_{75}\text{-}(aa)_{76}\text{-}(aa)_{77}\text{-}(aa)_{78}\text{-}$$
$$(aa)_{79}\text{-}(aa)_{80}\text{-}(aa)_{81}$$

In formula (IV):

- $(aa)_2$ is L, I, V, M, Q, E, or D, preferably L, I, or V.
- $(aa)_3$ is F, Y, G, M, L, I, or V, preferably F, Y, L, I or V.
- $(aa)_4$ is V, I, L, A, F, G, S, or D, preferably V, I or L.
- $(aa)_7$ is V, I, L, M, F, N, D, T, or G, preferably V, I or L.
- $(aa)_{14}$ is E, D, K, N, L, V, a deletion in the sequence, Q, or A, preferably E, D, K or N.
- $(aa)_{15}$ is S, E, L, M, I, K, D, A, P, R, a deletion in the sequence, or Q, preferably S, E, K or D.
- $(aa)_{17}$ is L, K, I, V, F, or R, preferably L, I or V.
- $(aa)_{18}$ is R, Y, S, Q, E, F, K, D, N or W, preferably D, E, K, R, Q, N or Y.
- $(aa)_{21}$ is F, L, T, E, D, Y, S, W or H, preferably F, Y, W or H.
- $(aa)_{22}$ is E, S, N, K, G, A, Q, R, C, Y or D, preferably D, E, K, R, Q, N or Y.
- $(aa)_{24}$ is Y, F, V, K, H, A, I, D, T, W, N, or a deletion in the sequence, preferably Y, F, H or W.
- $(aa)_{25}$ is G. P, S, A, L, E, I, a deletion in the sequence, T, M, or K, preferably G.
- $(aa)_{27}$ is I, F, V, S, P, or L, preferably L, I or V.
- $(aa)_{32}$ is M, I, L, V, A, a deletion in the sequence, F, D, or G, preferably L, I or V.
- $(aa)_{39}$ is G, L, M, a deletion in the sequence, N, K, R, I, E, S, Q, or T, preferably G.
- $(aa)_{40}$ is K, R, H, or a deletion in the sequence, A, E, L, G, R, S, T, H, Y, or Q, preferably R, H or a deletion in the sequence.
- $(aa)_{42}$ is R, K, H, D, L, a deletion in the sequence, or F, preferably R, K or H.
- $(aa)_{43}$ is G, D, L, V, a deletion in the sequence, or K, preferably G.
- $(aa)_{44}$ is Y, Q, I, F, S, a deletion in the sequence, V, or A, preferably Y or F.
- $(aa)_{45}$ is A, T, C, I, G, K, a deletion in the sequence, or C, preferably A or G.
- $(aa)_{46}$ is F, Y or a deletion in the sequence, preferably F or Y.
- $(aa)_{47}$ is I, V, A, L, R, or a deletion in the sequence, preferably L, I or V.
- $(aa)_{48}$ is E, I, Q, T, V, R, N, H, S, C, a deletion in the sequence, D, Y or K, preferably D, E, K, R, Q, N or Y.
- $(aa)_{49}$ is Y, F, S, G, a deletion in the sequence, or M, preferably Y or F.
- $(aa)_{58}$ is A, S, M, a deletion in the sequence, V, P, I, or N, preferably A.
- $(aa)_{63}$ is D, Q, W, E, Y, V, N, a deletion in the sequence, K, S, P, G, or T, preferably D, Q, W, E, a deletion in the sequence or K.
- $(aa)_{67}$ is I, F, L, a deletion in the sequence, Q, S, E, V, P, or M, preferably L, I or V.
- $(aa)_{69}$ is G, S, D, Q, P, K, a deletion in the sequence, Y, I, T, or N, preferably G.
- $(aa)_{73}$ is V, M, A, T, N, F, I, C, L, a deletion in the sequence, Q, or K, preferably V, M, A, F, I, C, or
- $(aa)_{75}$ is V, I, a deletion in the sequence, M, L, C, P, Y or E, preferably L, I or V.
- $(aa)_{78}$ is E, A, N, a deletion in the sequence, L, G, S, F, H, R, K, T, P, Q, O, or M, preferably A.
- $(aa)_{80}$ is R, D, G, a deletion in the sequence P, QE, I, N, K, or T, preferably D, E, K, R, Q, N or a deletion in the sequence.
- $(aa)_1$, $(aa)_5$, $(aa)_6$, $(aa)_{8-13}$, $(aa)_{16}$, $(aa)_{23}$, $(aa)_{26}$, $(aa)_{28}$, $(aa)_{33}$, $(aa)_{38}$, $(aa)_{41}$, $(aa)_{50}$, $(aa)_{55-57}$, $(aa)_{59}$, $(aa)_{60-621}$, $(aa)_{64-66}$, $(aa)_{68}$, $(aa)_{70}$, $(aa)_{71}$, $(aa)_{73}$, $(aa)_{75}$, $(aa)_{76}$, $(aa)_{78}$, $(aa)_{79}$ and $(aa)_{81}$ are each independently, one member selected from the group consisting of the amino acids and deletions in said sequence.
- $(aa)_{16}$ and $(aa)_{17}$ are linked to each other via either (i) a covalent bond or (ii) up to three amino acids selected from the group consisting of the amino acids.
- $(aa)_{59}$ and $(aa)_{60}$ are linked to each other via either (i) covalent bond or (ii) one amino acid selected from the group consisting of the amino acids.
- $(aa)_{19}$ and $(aa)_{20}$ represent at least two and up to four members selected from the group consisting of the amino acids and deletions in the sequence.
- $(aa)_{29\text{-}31}$ represent at least three and up to five members selected from the group consisting of the amino acids and deletions in the sequence.
- $(aa)_{34-37}$ represent at least five and up to seven members selected from the groups consisting of the amino acids and deletions in the sequence.
- $(aa)_{51-54}$ represent at least four and up to seven members selected from the group consisting of the amino acids and deletions in the sequence.

The proteins provided by this embodiment also include modifications of the proteins comprising the core components set out in FIG. 6 having at least 35% homology with the consensus sequence provided in the figure.

In another embodiment, the present invention provides proteins corresponding to the binding domains of the snRNP 70K protein, the La protein, the 60K Ro protein and the U1 snRNP A protein. The binding domains of the La protein, the 60K Ro protein and the U1 snRNP A protein correspond to a core which is the partial sequences given in FIG. 6 for each of these proteins to which can be added up to 10 amino acids, and preferably up to 20 amino acids, to both ends of the protein. These 10 amino acids, and preferably 20 amino acids, correspond to the amino acids found at those position in the native protein.

For the La protein the core section of the protein corresponds to about residue nos. 112 and 187. Preferably the core is residues 104 to 202 of the protein. For the 60K Ro protein the binding domain is comprised of that core section of the protein between residue nos. 92 and 162. For U1 snRNP A#1 the core is residue nos. 11 and 91. Preferably the binding domain is residues 11 to 104 of the protein. And for U1 snRNP A#2 the core is residue nos. 210 to 283. Preferably the domain is residues 200 to 283.

In another embodiment the present invention provides peptides and proteins comprising at least either the amino acid sequence $(aa)_{26}$ to $(aa)_{38}$ or $(aa)_{31}$ to $(aa)_{38}$, inclusive, of formula (IV), and, for each, up to the whole sequence of formula (IV). In a related embodiment, for these two peptides and proteins, preferably the sequences $(aa)_{26}$ to $(aa)_{38}$ and $(aa)_{31}$ to $(aa)_{38}$ are as follows:

$(aa)_{26}$-$(aa)_{27}$-$(aa)_{28}$-$(aa)_{29}$-$(aa)_{30}$-$(aa)_{31}$-$(aa)_{32}$-$(aa)_{33}$-$(aa)_{34}$-$(aa)_{35}$-$(aa)_{36}$-$(aa)_{37}$-$(aa)_{38}$ wherein:
- $(aa)_{26}$ is P, S, D, N, K, T, E;
- $(aa)_{27}$ is I, F, V, S, P, or L;
- $(aa)_{28}$ is K, V, L, R, E;
- $(aa)_{29}$ is S, V, D, E, N, A, I, R;
- $(aa)_{30}$ is I, V, P, C, R, A;
- $(aa)_{31}$ is R, K, V, Q, I, S, D, H;
- $(aa)_{32}$ is M, I, L, V, A, a deletion in said sequence, F, D, or G;
- $(aa)_{33}$ is M, V, R, P, L, C;
- $(aa)_{34}$ is a deletion or R, T, K, M, P, A;
- $(aa)_{35}$ is a deletion or D, A;
- $(aa)_{36}$ is a deletion or R, P, N, E, L, A, K, G;
- $(aa)_{37}$ is N, G, R, Q, D, K, E, L; and
- $(aa)_{38}$ is T, S, D, Q, H, wherein, to each end of $(aa)_{26}$ to $(aa)_{38}$ (or to $(aa)_{31}$ to $(aa)_{38}$) is optionally attached part or the whole corresponding amino acid sequences of 70K U1 snRNP protein or amino acid sequences having 35% homology therewith.

Another embodiment relates to the inventors' discovery that the A and B" proteins (see also FIG. 6) in the variable region (see FIG. 11A) control the specificity of RNA recognition by the U2 snRNP-B" and U1 snRNP-A proteins. Thus a five amino acid sequence in the RNA recognition motif of the U2 snRNP-B" protein was found to confer. U2 RNA recognition when substituted into the corresponding position in the U1 snRNP-A protein. In addition, B" was found to require the U2 snRNP-A' protein as an accessory factor for high affinity binding to U2 RNA. The pentamer sequence in B" that controls U2 RNA recognition was not sufficient to allow the A' enhancement of U2 RNA binding by B". Other regions of the RNA binding domain are therefore important for this interaction. These findings show that intermolecular protein-protein interactions can alter the specificity and affinity of RNA recognition, providing a regulatory role for accessory proteins in the formation of RNP complexes involved in RNA processing.

The A (Sillekens et al., *Nucleic Acids Res.* (1987) 17:1893–1906) and U2 snRNP-B" ("B") (Habets et al., *Proc. Nat. Acad. Sci.* (*USA*) (1987) 84:2421–2425) proteins each contain two RRMs. The sequences within the corresponding motifs of these proteins are highly conserved (Sillekens et al. (1987)). Their amino-terminal RRMs are 75% identical and their carboxy-terminal RRMs are 86% identical. Despite the high degree of primary amino acid sequence similarity, these two proteins associate with different RNAs in vivo (reviewed in Zieve, 1990). The inventors realized that A and B" might be useful models to study the determinants of RNA recognition with the RRM. They have constructed a series of recombinant cDNA molecules encoding permutations between the RRMs of A and B" and found that substituting a five amino acid sequence from B" into A confers the ability to recognize U2 RNA. They discovered that B" requires $A^{prime}$ for specific high affinity binding of B" to U2 RNA in vitro, and that the five amino acid change uncouples the recognition of U2 RNA from the ability to respond to $A^{prime}$. The molecular interactions that control U2 RNA-recognition by B" demonstrate that the function of an RRM as an RNA binding domain can be regulated by specific sequences within the RRM, as well as through intermolecular interactions with other proteins.

Determinants of specific RNA recognition within the the RNA recognition motif

Figure 11A:
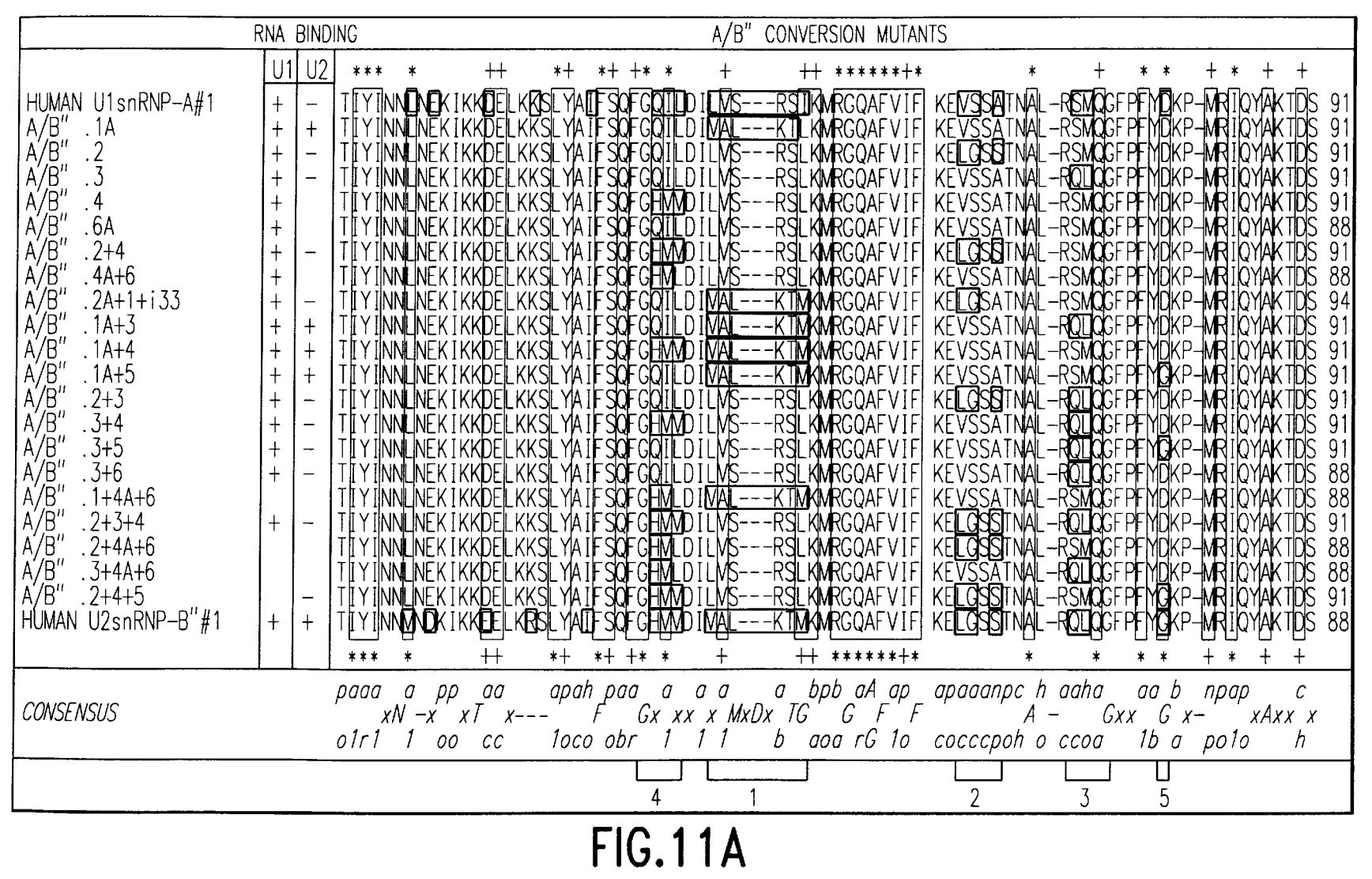

The inventors have discovered that the U1 snRNP-A protein can be altered to recognize U2 RNA by modification of a five amino acid segment to the corresponding sequence in a related protein, B" (FIG. 11A). This region includes the most divergent positions within the RRM family, both in amino acid composition and in length, which varies from 1 to 14 amino acids. This region is identified as variable region-1 (VR-1) in this text. It encompasses the sequence indicated in FIG. 11A as block 1. The presence of this poorly conserved element of sequence within the larger motif shows either that the element is extraneous and unnecessary or that the element is involved in functions unique to individual proteins. The poorly conserved VR-1 region is responsible for at least some of the differing RNA recognition properties of A and B" and may play a similar role in other RRM-containing proteins.

It is likely that in such a large and diverse family of proteins, multiple sequence elements have the potential to influence RNA binding specificity. Cross-species comparisons of VR-1 in the few proteins in which phylogenetically diverse sequences are available show conservation in some but not all family members. The La protein, for example, is almost identical in this region in the human (Chambers et al., *J. Biol. Chem.* (1988) 263:18043–18051), bovine (Chan et al. (1989) 17:2233–2244) and frog (Moreau et al., *Mol. Biol. Reports* (1990) 14:51) sequences whereas other regions in the La RRM are more divergent, suggesting that VR-1 may play an important role in RNA recognition by La.

In contrast, the U1 snRNP-70K protein VR-1 sequence is not phylogenetically conserved in either length or sequence between human (query et al. (1989), and references therein), frog (Etzerodt, *EMBO J.* (1988) 7:4311–4321) and fly (Mancebo et al. *Mol. Cell. Biol.* (1990) 10:2492–2502) even though the remainder of the RRM is almost identical. Thus, VR-1 may not be a critical determinant of RNA specificity in all RRM proteins.

Secondary structure predictions for the RRM family suggest that VR-1 might reside in a predicted loop between two beta strands, one of which contains the highly conserved RNP octamer (Ghetti et al., *F.E.B.S. Letters* (1989) 242:225–232). Specific aromatic amino acids within the RNP octamer are necessary for RNA binding (Lutz-Freyermuth et al. (1990)) and a conserved phenylalanine within the octamer can be crosslinked to oligodeoxythymidine (Merrill et al., *J. Biol. Chem.* (1988) 263:3307–3313), suggesting that the octamer might directly contact the bound RNA. VR-1 might function by positioning the RNP octamer or another RNA-contact region into the correct orientation.

In the crystallographic analysis of a tRNA-aminoacyl synthetase cocrystal, multiple protein-RNA contacts were observed (Rould et al., *Science* (1989)256:1135–1142). Thus, there are likely to be additional RRM-RNA contacts not controlled by VR-1. In the unique case studied here, both A and B" proteins and the U1 and U2 RNAs possess very similar sequences (FIG. 10B) and therefore probably share a common secondary structure in which elements of sequence substituted from one protein can still function properly in the other.

Accessory factors influencing formation and activity of an RNA binding domain

B" requires the action of an accessory protein, $A^{prime}$, to function as a U2 RNA-specific binding protein. Accessory factors that modulate the nucleic acid binding activity of proteins in other systems are known, including transcription factors that function as heterodimers (reviewed in Ptashne, (1988) "How eukaryotic transcriptional activators work." *Nature* (London) 335, 683–689; Pabo et al., *Ann. Rev.* (1984) 53:293–321). Protein-protein interactions have also been reported among RNA-binding proteins. For example, two proteins in the signal recognition particle, SRP9 and SRP14, form a heterodimer which binds specifically to 7SL RNA, and at least two 30S ribosomal proteins (S6 and S18) have a mutual requirement for binding to 16S rRNA. B" is unique in that it represents an RNA-binding protein with intrinsic affinity for its cognate RNA, but which nevertheless requires an accessory factor ($A^{prime}$) to optimize its affinity for that RNA.

The experiments reported here do not address the mechanism by which B" interacts with $A^{prime}$. However, $A^{prime}$ contains a repeating motif of leucine and asparagine residues common to several proteins known to be involved in protein-protein interactions. Furthermore, $A^{prime}$ has no detectable direct RNA binding activity using several assays (FIG. 8A, lanes 11 and 12. Therefore, we propose that $A^{prime}$ acts primarily through protein-protein interactions with B". The finding of an accessory factor for B" has implications for studies of RNA binding by other members of the RRM family. For example, it may be necessary to include accessory factors or cell extracts in binding reactions involving other RRM-containing proteins of unknown RNA specificity.

Role of the U2 snRNP-specific proteins

As isolated from cell extracts the U2 snRNP contains the Sm complex and the $A^{prime}$ and B" proteins. It is not known which proteins are present on the U2 snRNP in the assembled splicesome. However, anti-U2 RNP autoimmune sera (which recognize B" or $A^{prime}$) do not inhibit in vitro splicing. Furthermore, injection of U2 RNA lacking the RNA binding site for $A^{prime}$ and B" (stem-loop IV) into oocytes depleted of endogenous U2 snrnps restored RNA splicing in the same manner as full-length U2 RNA. Thus, $A^{prime}$- and B"- containing snRNPs may not be required for splicing. If the results of our in vitro reconstitutions reflect events in vivo, formation of U2 snrnps could be regulated by the level of $A^{prime}$ protein, or that the binding of $A^{prime}$ could prevent assembly of U2 snRNPs into the spliceosome. Thus, $A^{prime}$ and B" could play an important regulatory role in the formation or disassembly of the spliceosome rather than participating directly in RNA-splicing reactions. In light of the above, in another embodiment, the present invention provides two peptides or proteins comprising at least amino acids 26 to 38 of U1 snRNPA protein and corresponding to amino acids 26 to 38 of U2 snRNP-B and "protein". These peptides or protein possess at least 35% homology with respectively, amino acids 11 to 91 of U1 snRNP-A protein and amino acids 8 to 88 of U2 snRNP-B and "protein". These peptides or proteins further also contain at least amino acids 26 to 38, in both cases, and up to amino acids 11 to 91 of U1 snRNP-A protein and up to amino acids 8 to 88 of U2 snRNP-B "protein".

In another embodiment, the present invention provides an RNA sequence corresponding to stem loop I of human U1 RNA. The RNA sequence is:

5'GGGAGAUACCAUGAUCACGAAGGUGGUUUUCCC3'

In another embodiment, the present invention provides a ribonucleoprotein comprising one of the proteins provided by the present invention attached to a component X (e.g., a peptide X), the present protein being used in a binding reaction with its cognate RNA (i.e. stem loop I) that is, in turn attached to a component Y (e.g., a RNA Y) to allow the detection, contact, cellular targeting and/or functional interaction of the two adjoined components.

In another embodiment, the present invention provides a ribonucleoproteins in which a U1 snRNP 70K protein, a La protein, a 60K Ro protein or a U1 snRNP A protein is attached to a different peptide X with the protein being used in a binding reaction with its cognate RNA that is, in turn, attached to a different RNA Y to permit the detection, contact, cellular targeting and/or functional interaction of the adjoined component.

As discussed in greater detail below, this peptide X can be any kind of labelled material, a ribonuclease, a methylase, a ribozyme carrying enzyme, or a RNA protease, for example. As also discussed in greater detail below, this RNA Y can be a riboenzyme or a complementary sequence, in the latter case, the RNA Y being used as a probe. An example of a probe is RNA which is complementary to HIV RNA.

The term "the amino acids" in this text refers to all of the amino acids listed in Table 1 and FIG. 6.

Preparation of the materials of the invention:

The polydeoxyribonucleotide, proteins and other materials used in the present invention may be obtained using any method well known in the art to produce proteins or peptides.

Thus, the present proteins may be synthesized using any of the well known protein synthesis procedures, for example, by using solid-phase Merrifield synthesis techniques. They may also be obtained by fermentation of an appropriately genetically engineered microorganism capable of producing this peptide using well known technique. Or by the way be obtained by in vitro translation using messenger RNA or using in vitro transcribed RNA. A combination of genetic engineering and protein synthesis may be used. They can also be obtained by purification hydrolysis of proteins of natural origin. Thus in another embodiment, the present invention also provides polydeoxyribonucleotides which encode the proteins of the present invention.

Uses of the proteins:

In a first embodiment, the present proteins can be used in an assay in which the ability of the present proteins to specifically bind to region (I) of U1 RNA is exploited. In this embodiment, either the present protein or a portion of U1 RNA, the latter being capable of specifically binding with the present proteins (e.g., stem-loop (I)), is covalently attached (using known methods) to a probe molecule. Illustrative examples of probe molecules include DNA, RNA, antigens, or antibodies, i.e., compounds known to be useful in probes. In this assay, either the present protein or at least part of U1 RNA sufficient to specifically bind to the present protein is used as the marker component. Its presence in an assay sample is then detected using its binding partner.

Binding of the defined domain of the 70K protein can be used to detect the presence of the binding site of U1 RNA or the entire U1 RNA alone, even when either is attached to other molecules. For example, U1 RNA can be attached to another RNA probe that is specific for a given DNA or RNA one wishes to detect by base sequence complementarity. The 70K RNA binding domain can be labeled with any of several standard markers such as radioactive tags, ELISA enzymes or biotinylated compounds. When the complementary nucleic acid is detected, the protein domain can be used to detect the binding reaction.

As an example, the U1 RNA binding site consisting of 31 to 33 nucleotides, stem-loop (I) shown in FIG. 1, is attached to an RNA that is complementary to the RNA of the AIDS/HIV virus. This chimeric RNA can be expressed from any of the common RNA synthesis vectors such as those that use the Sp-6 o T7 promoters (Melton et al, 1986) *Nucleic Acids Res.* (1984) 12: 7035–7056). The template DNA for synthesis of the chimeric RNA is designed to contain sequences of the U1 RNA antisense and HIV RNA sense so that hybridization probes of the HIV antisense are synthesized. Thus, the chimeric RNA probe contains sense U1 RNA (e.g., any fragment of U1 RNA that encompasses the shaded portion in FIG. 1) that will bind specifically to the 70K RNA binding domain (e.g., any fragment of 70K that encompasses the blocked domain in FIG. 2, but eliminates amino acids 241 to 437).

Once the chimeric RNA probe is reacted with a HIV suspected sample, a tagged (e.g., radioactive, ELISA or strep-avidin) 70K RNA binding domain is used to recognize the presence of the chimeric hybrid in the body fluid sample. Natural U1 RNA is not present in these fluids.

In addition, the U1 RNA binding site can be linked to the hybridization probe in a repeated fashion over many cycles to dramatically increase the signal of detection. Likewise, this specific protein-RNA binding reaction can be used to tag, quantitate and amplify the signal of detection of other nucleic acid hybridizations. Several aspects of this method are published (cf. Query et al, *Cell* (1989) 57:89–101 and *Mol Cell. Biol.* (1989) 9(11):4872–4881). These can be achieved by attaching the 70K RNA binding domain to a protein tag, beta-galactosidase, that, in turn, is recognized and detected using a specific monoclonal antibody (FIG. 3). Similarly, another antibody tag of 12 amino acids termed S-10 can be linked to the 70K RNA binding domain without altering binding specificity. Likewise, it is possible to produce various modifications to the U1 RNA binding site by addition of foreign RNA sequences onto the 5' or 3' ends of the RNA (op.cit.).

This demonstrates the ability to modify the composition of a ribonucleoprotein complex using a variety of protein or nucleic acid sequences so as to design and create novel RNP structures. This is made possible by the inventors' discovery of the specific binding properties of the 70K RNA binding domain with the U1 RNA binding site.

Another use of the RNA-protein binding reaction is to employ two linked 70K RNA binding domains that can bridge together two different RNA molecules. This allows one to build chains of RNA-protein complexes to span larger distances or to increase the signal of a probe.

For example, recombinant DNA encoding the RNA binding domain of the 70K protein can be ligated in tandem using standard methods Maniatis, T., Fritsch, E. F. and Sanbrook, J. (1982) Molecular Cloning: A Laboratory Manual (Cold Spring Harbor Laboratory, Cold Spring Harbor, N.Y.) and expressed in bacteria. For example, the 70K RNA binding domain can be expressed in the Studier T7 expression system which is suitable for this tandem construction (Rosenberg et al, *Gene* (1987) 56: 125–135).

With two 70K RNA binding domains linked and expressed, a molecule is produced that can join two molecules of U1 RNA. Thus, a synthetic RNA bridge is created. By linkage of different RNAs to the U1 RNAs being bridged, one can connect various heterologous RNAs to one another using the 70K protein binding domain. As a specific example, one can link hybridization probes for the HIV RNA together in tandem or to other functional RNAs such as ribozymes or to RNA chains containing useful tags (e.g., biotinylated).

Another embodiment of this invention involves the use of the 70K RNA binding domain to detect or modify the functions of ribozymes. Ribozymes are RNA molecules that have enzymatic activity without the presence of protein (Cech, *J. Amer. Med. Assoc.* (1988) 260: 3030–3034). Methods are needed to detect, target and modify ribozymes at specific sites within the cells of the body. Because of its ability to specifically bind RNA, the 70K RNA binding domain and the U1 RNA binding site can be used to tag ribozymes and to target them to specific sites within cells.

The 70K RNA binding domain can thus be used to target and tag specific ribozymes either in vivo or in vitro. Thus, RNA-based enzymes with specific sites of function in the body or in the test tube can be designed to be recognized by the RNA binding domain. The functions for the ribozyme include site-specific RNA cleavage (Zaug et al, *Nature* (1986) 324: 429–433; Haseloff et al, *Nature* (1988) 334: 585–591) or RNA-catalyzed synthesis (Doudna, *Nature* (1989) 339: 519–522). Other ribozyme-mediated reactions are also possible that involve enzymatic modifications of proteins, carbohydrates or other cellular constituents by ribozymes.

The method of recognition utilizing the 70K RNA binding domain can be of two kinds.

(1) The ribozyme can be linked to the U1 RNA binding site that is recognized by the 70K protein RNA binding domain. Thus, a chimeric U1 RNA-ribozyme RNA is formed and recognized by the RNA binding domain via the U1 RNA component of the chimera.

(2) The 70K RNA binding domain can be modified by design to recognize portions of the ribozyme directly. Method 1 can be practiced at present and method 2 will be possible in the near future. By both methods, the 70K RNA binding domain is used as either a carrier molecule, as a detectable tag or for catalytic modulation of the ribozyme.

Approaches 1 and 2 provide the following uses. An injected ribozyme with a pharmaceutical repair function in the body can be scavenged up or detected directly by binding reactions involving the 70K RNA binding domain. In this embodiment, the 70K RNA binding domain contains a radioactive or other tag to quantitate the levels of ribozyme in the tissues or bloodstream at any given time. This assay involves a sample from the patient being placed on an immobilized surface and a binding assay performed using the tagged RNA binding domain. In a manner analogous to an antigen-antibody reaction, the level of immobilized RNA is quantitated.

As another example, 70K RNA binding domain attached to specific ribonucleases is administered to a patient in an amount sufficient and at an appropriate site so as to search out and to destroy a specific ribozyme. As an example, the RNA binding domain of 70K is linked at the DNA level using standard recombinant methods (Maniatis et al (1982), supra) to DNA encoding pancreatic ribonuclease A or to an active fragment thereof. The ribozyme of interest possessing any of several enzymatic activities can be linked to the U1 RNA binding site. After the ribozyme is injected at its appropriate site and allowed to act on its target, the chimeric 70K-ribonuclease A is injected to locate the U1-ribozyme and destroy it.

If this method is used to clear residual ribozyme from the bloodstream, for example, the protein inactivator would likely be more stable than the U1-ribozyme molecule. Thus, all residual ribozyme would be efficiently inactivated using very low doses of the chimeric protein.

Thus, injection of ribozyme levels to attain concentrations of 1 picomole of active U1 ribozyme per deciliter of blood could be inactivated by addition of equimolar to subequimolar amounts 0.01 to 1.0 picomoles per deciliter. If modified ribonucleoside phosphates are substituted into the ribozyme to enhance its stability (Lamond et al, Cell (1989)58: 383–390), the chimeric inactivator molecule may be designed to specifically recognize, sequester or destroy the modified RNA molecules, thus, allowing highly specific dosage, stability and destruction of a ribozyme.

The 70K RNA binding domain can also be attached to a specific targeting signal (e.g., a nuclear, nucleolar, chloroplast, or mitochondrial targeting sequence, or a receptor-specific ligand). Using this approach, a ribozyme in association with the domain can be targeted to a specific tissue, cell type, sub-cellular compartment, or other molecule at a defined site. Cellular targeting signals specific for compartments such as the nucleus have been defined (Kalderon et al, Nature (1984) 311: 33–37; Adam et al, Nature (1989) 337: 276–279 and can be linked to the 70K RNA binding domain for compartmental access.

In a similar manner, cell surface receptors can be used for targeting the 70K RNA binding domain and attached ribozymes to specific tissues. Receptor recognition is well established. See, e.g., Dixon et al, EMBO J. (1987) 6: 3269–3275; Minneman et al, Mol. Pharmacol. (1979) 16: 34–46), and receptors that are specific for cancer cells are known (Benbrook et al, Nature (1988) 333, 669–672). New methods for modeling receptors (Itai et al, Proc. Natl. Acad. Sci. (USA) (1988) 85: 3688–3692) can be used to design targeted ribonucleoproteins. Prior to this invention, methods of targeting ribozymes to specific sites were not known and the 70K RNA binding domain provides such specificity.

Ribozymes can be used as agents to target particular messenger or pre-messenger RNAs for destruction (Haseloff et al, Nature (1988) 334: 585–591). One way to target a particular RNA for ribozyme cleavage is to attach a 70K RNA binding domain that is designed to carry the ribozyme to a specific sequence in a particular RNA. This can be achieved by linking the U1 RNA binding domain of 70K to a ribonuclease protein or ribozyme so as to specifically destroy U1 RNA. But, in addition, changes in the specificity of recognition by the RNA binding domain may allow one to direct the ribozyme to a specific site in a particular mRNA and to none other. Thus, the expression of particular genes in a eukaryotic or prokaryotic cell can be specifically altered by use of this method.

Targeting of the ribozyme to the correct RNA sequence can be mediated by a bifunctional RNA binding protein (as described above) with one surface recognizing the ribozyme and another surface recognizing the second RNA. For example, the RNA binding domain for nucleolin (FIG. 6) can be linked to the 70K RNA binding domain using a standard recombinant plasmid system (Maniatis, 1982. Molecular cloning: a laboratory mammal—Cold Spring Harbor Laboratory, Cold Spring Harbor, N.Y.) and expressed as a chimeric protein with two RNA binding surfaces. The U1 RNA binding domain when linked to a ribozyme Tet 1.0 nuclease can serve as the handle to target the ribozyme to precursor ribosomal RNA (binding molecule for nucleolin) in the presence of the chimeric bifunctional RNA binding protein.

A distinct class of ribozyme activity was recently described (Wu et al, Proc. Natl. Acad. Sci. (USA) (1989) 86: 1831–1835) that is part of the RNA genome of the hepatitis delta RNA. This autocatalytic reaction is more efficient than any of those identified previously in other ribozymes. Such an autocatalytic cleavage reaction is required for the replication cycle of the virus. The 70K RNA binding domain can be used to target the hepatitis genome for specific destruction using the methods described above for targeted nucleases. In addition, the levels of the hepatitis delta RNA in the blood of patients with hepatitis could be quantitiated using the specific binding reactions described above. With the design and construction of appropriate RNA binding domains it will be possible to directly detect and inhibit the functions of the hepatitis delta ribozyme. Furthermore, the efficient hepatitis delta ribozyme could be used in a novel ribonucleoprotein designed as illustrated herein to target other cellular RNAs for modification or destruction.

In a similar manner, the RNA of the human immunodeficiency virus (HIV) can be modified or destroyed using the methods described for the hepatitis virus RNA. Thus, using the specific RNA binding reactions and constructing novel ribonucleoproteins, it will be possible to detect, target or modify the genome of the HIV virus.

In another embodiment of this method, chimeric molecules involving the 70K RNA binding domain can be used for site-specific modification of RNA. The RNA binding domain that specifically recognizes an RNA sequence is used to target the RNA for modifications that are different than those originally possessed by the protein containing the RNA binding domain.

For example, the 70K RNA binding domain is attached to an active segment of ribonuclease and the chimeric fusion protein used to specifically destroy U1 RNA either in vitro or in vivo. Likewise, other RNAs attached to or associated with the U1 RNA target are accessed by the nuclease.

Thus, the nucleases are directed at specific sites on the attached RNA, thus, functioning as RNA restriction endonucleases or used to destroy any RNA associated with the target U1RNA. Also, this approach is used to direct other RNA modifying activities to specific sites in RNAs including RNA ligases and kinases, RNA methylases, or RNA capping enzymes.

Likewise, other RNA sequences (e.g., RNA-X) can be linked to the U1 RNA target and the chimeric proteins used to modify RNA-X. For example, RNA-X can be complementary to two other RNA molecules that may base pair with it. When the chimeric RNA binding domain linked to RNA ligase is added, the two complementary RNAs can be linked. Thus, site-specific RNA ligases can be designed using this method.

In these uses, the following are provided by the present invention.

A complex of formula (V):

(component x)—(protein)—(cognate RNA)—(component Y)

wherein:

(i) said protein is a protein having at least 48 amino acid residues and an amino acid sequence comprised within formula (IV), wherein formula (IV) is:

$(aa)_1$-$(aa)_2$-$(aa)_3$-$(aa)_4$-$(aa)_5$-$(aa)_6$-$(aa)_7$-$(aa)_8$-
$(aa)_9$-$(aa)_{10}$-$(aa)_{11}$-$(aa)_{12}$-$(aa)_{13}$-$(aa)_{14}$-$(aa)_{15}$-
$(aa)_{16}$-$(aa)_{17}$-$(aa)_{18}$-$(aa)_{19}$-$(aa)_{20}$-$(aa)_{21}$-$(aa)_{22}$-
$(aa)_{23}$-$(aa)_{24}$-$(aa)_{25}$-$(aa)_{26}$-$(aa)_{27}$-$(aa)_{28}$-$(aa)_{29}$-
$(aa)_{30}$-$(aa)_{31}$-$(aa)_{32}$-$(aa)_{33}$-$(aa)_{34}$-$(aa)_{35}$-$(aa)_{36}$-
$(aa)_{37}$-$(aa)_{38}$-$(aa)_{39}$-$(aa)_{40}$-$(aa)_{41}$-$(aa)_{42}$-$(aa)_{43}$-
$(aa)_{44}$-$(aa)_{45}$-$(aa)_{46}$-$(aa)_{47}$-$(aa)_{48}$-$(aa)_{49}$-$(aa)_{50}$-
$(aa)_{51}$-$(aa)_{52}$-$(aa)_{53}$-$(aa)_{54}$-$(aa)_{55}$-$(aa)_{56}$-$(aa)_{57}$-
$(aa)_{58}$-$(aa)_{59}$-$(aa)_{60}$-$(aa)_{61}$-$(aa)_{62}$-$(aa)_{63}$-$(aa)_{64}$-
$(aa)_{65}$-$(aa)_{66}$-$(aa)_{67}$-$(aa)_{68}$-$(aa)_{69}$-$(aa)_{70}$-$(aa)_{71}$-
$(aa)_{72}$-$(aa)_{73}$-$(aa)_{74}$-$(aa)_{75}$-$(aa)_{76}$-$(aa)_{77}$-$(aa)_{78}$-
$(aa)_{79}$-$(aa)_{80}$-$(aa)_{81}$

Wherein:

- $(aa)_2$ is L, I, V, M, Q, E, or D;
- $(aa)_3$ is F, Y, G, or M;
- $(aa)_4$ is V, I, L, A, F, G, S, or D;
- $(aa)_7$ is V, I, L, M, F, N, D, T, or G;
- $(aa)_{14}$ is E, D, K, N, L, V, a deletion in said sequence, Q, or A;
- $(aa)_{15}$ is S, E, L, M, I, K, D, A, P, R, a deletion in said sequence, or Q;
- $(aa)_{17}$ is L, K, I, V, F, or R:
- $(aa)_{18}$ is R, Y, S, Q, E, F, K, D or W;
- $(aa)_{21}$ is F, L, T, E, D, Y, or S;
- $(aa)_{22}$ is E, S, N, K, G, A, Q, R, C, or D;
- $(aa)_{24}$ is Y, F, V, K, H, A, I, D, T, W, N, or a deletion in said sequence;
- $(aa)_{25}$ is G, P, S, A, L, E, I, a deletion in said sequence, T, M, or K;
- $(aa)_{27}$ is I, F, V, S, P, or L;
- $(aa)_{32}$ is M, I, L, V, A, a deletion in said sequence, F, D, or G;
- $(aa)_{39}$ is G, L, M, a deletion in said sequence, N, K, R, I, E, S, Q, or T;
- $(aa)_{40}$ is K, a deletion in said sequence, A, E, L, G, R, S, T, H, Y, or Q;
- $(aa)_{42}$ is R, K, H, D, L, a deletion in said sequence, or F;
- $(aa)_{43}$ is G, D, L, V, a deletion in said sequence, or K;
- $(aa)_{44}$ is Y, Q, I, F, S, a deletion in said sequence, V, or A;
- $(aa)_{45}$ is A, T, C, I, G, K, a deletion in said sequence, or C;
- $(aa)_{46}$ is F, Y or a deletion in said sequence;
- $(aa)_{47}$ is I, V, A, L, R, or a deletion in said sequence;
- $(aa)_{48}$ is E, I, Q, T, V, R, N, H, S, C, a deletion in said sequence, D, Y or K;
- $(aa)_{49}$ is Y, F, S, G, a deletion in said sequence, or M;
- $(aa)_{58}$ is A, S, M, a deletion in said sequence, V, P, I, or N;
- $(aa)_{63}$ is D, Q, W, E, Y, V, N, a deletion in said sequence, K, S, P, G, or T;
- $(aa)_{67}$ is I, F, L, a deletion in said sequence, Q, S, E, V, P, or M;
- $(aa)_{69}$ is G, S, D, Q, P, K, a deletion in said sequence, Y, I, T, or N;
- $(aa)_{73}$ is V, M, A, T, N, F, I, C, L, a deletion in said sequence, Q, or K;
- $(aa)_{75}$ is V, I, a deletion in said sequence, M, L, C, P, Y or E;
- $(aa)_{78}$ is E, A, N, a deletion in said sequence, L, G, S, F, H, R, K, T, P, Q, O, or M;
- $(aa)_{80}$ is R, D, G, a deletion in said sequence, P, Q, E, I, N, K, or T;
- $(aa)_1$, $(aa)_5$, $(aa)_6$, $(aa)_{8-13}$, $(aa)_{16}$, $(aa)_{23}$, $(aa)_{26}$, $(aa)_{28}$, $(aa)_{33}$, $(aa)_{38}$, $(aa)_{41}$, $(aa)_{50}$, $(aa)_{55-57}$, $(aa)_{59}$, $(aa)_{60-62}$, $(aa)_{64-66}$, $(aa)_{68}$, $(aa)_{70}$, $(aa)_{71}$, $(aa)_{73}$, $(aa)_{75}$, $(aa)_{761}$ $(aa)_{78}$, $(aa)_{79}$ and $(aa)_{81}$ are each, independently, one member selected from the group consisting of the amino acids and deletions in said sequence;
- $(aa)_{16}$ and $(aa)_{17}$ are linked to each other via (i) a covalent bond or (ii) up to three amino acids selected from the group consisting of the amino acids;
- $(aa)_{59}$ and $(aa)_{60}$ are linked to each other via (i) a covalent bond or (ii) one amino acid selected from the group consisting of the amino acids;
- $(aa)_{19}$ and $(aa)_{20}$ represent at least two and up to four members selected from the group consisting of the amino acids and deletions in said sequence;
- $(aa)_{29-31}$ represent at least three and up to five members selected from the group consisting of the amino acids and deletions in said sequence;
- $(aa)_{34-37}$ represent at least five and up to seven members selected from the groups consisting of the amino acids and deletions in said sequence; and
- $(aa)_{51-54}$ represent at least four and up to seven members selected from the group consisting of the amino acids and deletions in said sequence;

(ii) said component X is covalently bound to said protein, said component X being one member selected from the group consisting of labelled materials, ribonucleases, methylases, RNA capping enzymes and proteases;

(iii) said cognate RNA is completed to said protein and is a polyribonucleotide comprising at least the sequence:

5' GGAGAUACCAUGAUCACGAAGGUGGUUUUCCC 3' and up to the sequence of U1 RNA; and (iv) said component Y is covalently linked to said cognate RNA and is one member selected from the group consisting of DNA probes, RNA probes, antigens and antibodies.

Preferably, in the complex:

- $(aa)_2$ is L, I, or V;
- $(aa)_3$ is F, Y, L, I or V;
- $(aa)_4$ is V, I, or L;
- $(aa)_7$ is V, I, or L;
- $(aa)_{14}$ is E, D, K, or N;
- $(aa)_{15}$ is S, E, K, or D;
- $(aa)_{17}$ is L, I, or V;
- $(aa)_{18}$ is D, E, K, R, Q, N, or Y;
- $(aa)_{21}$ is F, Y, W, or H;
- $(aa)_{22}$ is D, E, K, R, Q, N or Y;
- $(aa)_{24}$ is Y, F, or W;
- $(aa)_{25}$ is G;
- $(aa)_{27}$ is L, I or V;
- $(aa)_{32}$ is L, I or V;
- $(aa)_{39}$ is G;
- $(aa)_{40}$ is R, H, or a deletion in said sequence;
- $(aa)_{42}$ is R, K, or H;
- $(aa)_{43}$ is G;
- $(aa)_{44}$ is Y, or F;
- $(aa)_{45}$ is A, or G;
- $(aa)_{46}$ is F, or Y;
- $(aa)_{47}$ is L, I, or V;

(aa)$_{48}$ is D, E, K, R, Q, N, or Y;
(aa)$_{49}$ is Y or F;
(aa)$_{58}$ is A;
(aa)$_{63}$ is D, Q, W, E, a deletion in said sequence, or K;
(aa)$_{67}$ is L, I, or V;
(aa)$_{69}$ is G;
(aa)$_{73}$ is V, M, A, F, I, C, or L;
(aa)$_{75}$ is L, I or V;
(aa)$_{78}$ is A; and
(aa)$_{80}$ is D, E, K, R, N, Q, or a deletion in said sequence.

Preferably, in the complex RNA Y is a RNA which is capable of binding with the RNA of the AIDS/HIV virus.

The present invention also provides a compound of formula (VI)

(component X)—(protein)

wherein:
(i) said component-X is covalently bound to said protein, said component X being one member selected from the group consisting of labelled materials; and
(ii) said protein is a protein having at least 48 amino acid residues and an amino acid sequence comprised within formula (IV), wherein formula (IV) is:

(aa)$_1$-(aa)$_2$-(aa)$_3$-(aa)$_4$-(aa)$_5$-(aa)$_6$-(aa)$_7$-(aa)$_8$-
(aa)$_9$-(aa)$_{10}$-(aa)$_{11}$-(aa)$_{12}$-(aa)$_{13}$-(aa)$_{14}$-(aa)$_{15}$-
(aa)$_{16}$-(aa)$_{17}$-(aa)$_{18}$-(aa)$_{19}$-(aa)$_{20}$-(aa)$_{21}$-(aa)$_{22}$-
(aa)$_{23}$-(aa)$_{24}$-(aa)$_{25}$-(aa)$_{26}$-(aa)$_{27}$-(aa)$_{28}$-(aa)$_{29}$-
(aa)$_{30}$-(aa)$_{31}$-(aa)$_{32}$-(aa)$_{33}$-(aa)$_{34}$-(aa)$_{35}$-(aa)$_{36}$-
(aa)$_{37}$-(aa)$_{38}$-(aa)$_{39}$-(aa)$_{40}$-(aa)$_{41}$-(aa)$_{42}$-(aa)$_{43}$-
(aa)$_{44}$-(aa)$_{45}$-(aa)$_{46}$-(aa)$_{47}$-(aa)$_{48}$-(aa)$_{49}$-(aa)$_{50}$-
(aa)$_{51}$-(aa)$_{52}$-(aa)$_{53}$-(aa)$_{54}$-(aa)$_{55}$-(aa)$_{56}$-(aa)$_{57}$-
(aa)$_{58}$-(aa)$_{59}$-(aa)$_{60}$-(aa)$_{61}$-(aa)$_{62}$-(aa)$_{63}$-(aa)$_{64}$-
(aa)$_{65}$-(aa)$_{66}$-(aa)$_{67}$-(aa)$_{68}$-(aa)$_{69}$-(aa)$_{70}$-(aa)$_{71}$-
(aa)$_{72}$-(aa)$_{73}$-(aa)$_{74}$-(aa)$_{75}$-(aa)$_{76}$-(aa)$_{77}$-(aa)$_{78}$-
(aa)$_{79}$-(aa)$_{80}$-(aa)$_{81}$

Wherein:
(aa)$_2$ is L, I, V, M, Q, E, or D;
(aa)$_3$ is F, Y, G, or M;
(aa)$_4$ is V, I, L, A, F, G, S, or D;
(aa)$_7$ is V, I, L, M, F, N, D, T, or G;
(aa)$_{14}$ is E, D, K, N, L, V, a deletion in said sequence, Q, or A;
(aa)$_{15}$ is S, E, L, M, I, K, D, A, P, R, a deletion in said sequence, or Q;
(aa)$_{17}$ is L, K, I, V, F, or R:
(aa)$_{18}$ is R, Y, S, Q, E, F, K, D or W;
(aa)$_{21}$ is F, L, T, E, D, Y, or S;
(aa)$_{22}$ is E, S, N, K, G, A, Q, R, C, or D;
(aa)$_{24}$ is Y, F, V, K, H, A, I, D, T, W, N, or a deletion in said sequence;
(aa)$_{25}$ is G, P, S, A, L, E, I, a deletion in said sequence, T, M, or K;
(aa)$_{27}$ is I, F, V, S, P, or L;
(aa)$_{32}$ is M, I, L, V, A, a deletion in said sequence, F, D, or G;
(aa)$_{39}$ is G, L, M, a deletion in said sequence, N, K, R, I, E, S, Q, or T;
(aa)$_{40}$ is K, a deletion in said sequence, A, E, L, G, R, S, T, H, Y, or Q;
(aa)$_{42}$ is R, K, H, D, L, a deletion in said sequence, or F;
(aa)$_{43}$ is G, D, L, V, a deletion in said sequence, or K;
(aa)$_{44}$ is Y, Q, I, F, S, a deletion in said sequence, V, or A;
(aa)$_{45}$ is A, T, C, I, G, K, a deletion in said sequence, or C;
(aa)$_{46}$ is F, Y or a deletion in said sequence;
(aa)$_{47}$ is I, V, A, L, R, or a deletion in said sequence;
(aa)$_{48}$ is E, I, Q, T, V, R, N, H, S, C, a deletion in said sequence, D, Y or K;
(aa)$_{49}$ is Y, F, S, G, a deletion in said sequence, or M;
(aa)$_{58}$ is A, S, M, a deletion in said sequence, V, P, I, or N;
(aa)$_{63}$ is D, Q, W, E, Y, V, N, a deletion in said sequence, K, S, P, G, or T;
(aa)$_{67}$ is I, F, L, a deletion in said sequence, Q, S, E, V, P, or M;
(aa)$_{69}$ is G, S, D, Q, P, K, a deletion in said sequence, Y, I, T, or N;
(aa)$_{73}$ is V, M, A, T, N, F, I, C, L, a deletion in said sequence, Q, or K;
(aa)$_{75}$ is V, I, a deletion in said sequence, M, L, C, P, Y or E;
(aa)$_{78}$ is E, A, N, a deletion in said sequence, L, G, S, F, H, R, K, T, P, Q, O, or M;
(aa)$_{80}$ is R, D, G, a deletion in said sequence, P, Q, E, I, N, K, or T;
(aa)$_1$, (aa)$_5$, (aa)$_6$, (aa)$_{8-13}$, (aa)$_{16}$, (aa)$_{23}$, (aa)$_{26}$, (aa)$_{28}$, (aa)$_{33}$, (aa)$_{38}$, (aa)$_{41}$, (aa)$_{50}$, (aa)$_{55-57}$, (aa)$_{59}$, (aa)$_{60-62}$, (aa)$_{64-66}$, (aa)$_{68}$, (aa)$_{70}$, (aa)$_{71}$, (aa)$_{73}$, (aa)$_{75}$, (aa)$_{76}$, (aa)$_{78}$, (aa)$_{79}$ and (aa)$_{81}$ are each, independently, one member selected from the group consisting of the amino acids and deletions in said sequence;

(aa)$_{16}$ and (aa)$_{17}$ are linked to each other via (i) a covalent bond or (ii) up to three amino acids selected from the group consisting of the amino acids (aa)$_{59}$ and (aa)$_{60}$ are linked to each other via (i) a covalent bond or (ii) one amino acid selected from the group consisting of the amino acids;

(aa)$_{19}$ and (aa)$_{20}$ represent at least two and up to four members selected from the group consisting of the amino acids and deletions in said sequence;

(aa)$_{29-31}$ represent at least three and up to five members selected from the group consisting of the amino acids and deletions in said sequence;

(aa)$_{34-37}$ represent at least five and up to seven members selected from the groups consisting of the amino acids and deletions in said sequence; and (aa)$_{51-54}$ represent at least four and up to seven members selected from the group consisting of the amino acids and deletions in said sequence.

Preferably, in the above compound:
(aa)$_2$ is L, I, or V;
(aa)$_3$ is F, Y, L, I or V;
(aa)$_4$ is V, I, or L;
(aa)$_7$ is V, I, or L;
(aa)$_{14}$ is E, D, K, or N;
(aa)$_{15}$ is S, E, K, or D;
(aa)$_{17}$ is L, I, or V;
(aa)$_{18}$ is D, E, K, R, Q, N, or Y;
(aa)$_{21}$ is F, Y, W, or H;
(aa)$_{22}$ is D, E, K, R, Q, N or Y;
(aa)$_{24}$ is Y, F, or W;
(aa)$_{25}$ is G;

(aa)₂₇ is L, I or V;
(aa)₃₂ is L, I or V;
(aa)₃₉ is G;
(aa)₄₀ is R, H, or a deletion in said sequence;
(aa)₄₂ is R, K, or H;
(aa)₄₃ is G;
(aa)₄₄ is Y, or F;
(aa)₄₅ is A, or G;
(aa)₄₆ is F, or Y;
(aa)₄₇ is L, I, or V;
(aa)₄₈ is D, E, K, R, Q, N, or Y;
(aa)₄₉ is Y or F;
(aa)₅₈ is A;
(aa)₆₃ is D, Q, W, E, a deletion in said sequence, or K;
(aa)₆₇ is L, I, or V;
(aa)₆₉ is G;
(aa)₇₃ is V, M, A, F, I, C, or L;
(aa)₇₅ is L, I or V;
(aa)₇₈ is A; and
(aa)₈₀ is D, E, K, R, N, Q, or a deletion in said sequence.

The present invention also provides:

(component Y)—(protein)

wherein:
(i) said component Y is covalently bound to said protein, said component Y being one member selected from the group consisting of DNA probes, RNA probes, antigens, and antibodies; and
(ii) said protein is a protein having at least 40 amino acid residues and an amino acid sequence comprised within formula (IV), wherein formula (IV) is:

$$(aa)_1\text{-}(aa)_2\text{-}(aa)_3\text{-}(aa)_4\text{-}(aa)_5\text{-}(aa)_6\text{-}(aa)_7\text{-}(aa)_8\text{-}(aa)_9\text{-}(aa)_{10}\text{-}(aa)_{11}\text{-}(aa)_{12}\text{-}(aa)_{13}\text{-}(aa)_{14}\text{-}(aa)_{15}\text{-}(aa)_{16}\text{-}(aa)_{17}\text{-}(aa)_{18}\text{-}(aa)_{19}\text{-}(aa)_{20}\text{-}(aa)_{21}\text{-}(aa)_{22}\text{-}(aa)_{23}\text{-}(aa)_{24}\text{-}(aa)_{25}\text{-}(aa)_{26}\text{-}(aa)_{27}\text{-}(aa)_{28}\text{-}(aa)_{29}\text{-}(aa)_{30}\text{-}(aa)_{31}\text{-}(aa)_{32}\text{-}(aa)_{33}\text{-}(aa)_{34}\text{-}(aa)_{35}\text{-}(aa)_{36}\text{-}(aa)_{37}\text{-}(aa)_{38}\text{-}(aa)_{39}\text{-}(aa)_{40}\text{-}(aa)_{41}\text{-}(aa)_{42}\text{-}(aa)_{43}\text{-}(aa)_{44}\text{-}(aa)_{45}\text{-}(aa)_{46}\text{-}(aa)_{47}\text{-}(aa)_{48}\text{-}(aa)_{49}\text{-}(aa)_{50}\text{-}(aa)_{51}\text{-}(aa)_{52}\text{-}(aa)_{53}\text{-}(aa)_{54}\text{-}(aa)_{55}\text{-}(aa)_{56}\text{-}(aa)_{57}\text{-}(aa)_{58}\text{-}(aa)_{59}\text{-}(aa)_{60}\text{-}(aa)_{61}\text{-}(aa)_{62}\text{-}(aa)_{63}\text{-}(aa)_{64}\text{-}(aa)_{65}\text{-}(aa)_{66}\text{-}(aa)_{67}\text{-}(aa)_{68}\text{-}(aa)_{69}\text{-}(aa)_{70}\text{-}(aa)_{71}\text{-}(aa)_{72}\text{-}(aa)_{73}\text{-}(aa)_{74}\text{-}(aa)_{75}\text{-}(aa)_{76}\text{-}(aa)_{77}\text{-}(aa)_{78}\text{-}(aa)_{79}\text{-}(aa)_{80}\text{-}(aa)_{81}$$

Wherein:
(aa)₂ is L, I, V, M, Q, E, or D;
(aa)₃ is F, Y, G, or M;
(aa)₄ is V, I, L, A, F, G, S, or D;
(aa)₇ is V, I, L, M, F, N, D, T, or G;
(aa)₁₄ is E, D, K, N, L, V, a deletion in said sequence, Q, or A;
(aa)₁₅ is S, E, L, M, I, K, D, A, P, R, a deletion in said sequence, or Q;
(aa)₁₇ is L, K, I, V, F, or R;
(aa)₁₈ is R, Y, S, Q, E, F, K, D or W;
(aa)₂₁ is F, L, T, E, D, Y, or S;
(aa)₂₂ is E, S, N, K, G, A, Q, R, C, or D;
(aa)₂₄ is Y, F, V, K, H, A, I, D, T, W, N, or a deletion in said sequence;
(aa)₂₅ is G, P, S, A, L, E, I, a deletion in said sequence, T, M, or K;

(aa)₂₇ is I, F, V, S, P, or L;
(aa)₃₂ is M, I, L, V, A, a deletion in said sequence, F, D, or G;
(aa)₃₉ is G, L, M, a deletion in said sequence, N, K, R, I, E, S, Q, or T;
(aa)₄₀ is K, a deletion in said sequence, A, E, L, G, R, S, T, H, Y, or Q;
(aa)₄₂ is R, K, H, D, L, a deletion in said sequence, or F;
(aa)₄₃ is G, D, L, V, a deletion in said sequence, or K;
(aa)₄₄ is Y, Q, I, F, S, a deletion in said sequence, V, or A;
(aa)₄₅ is A, T, C, I, G, K, a deletion in said sequence, or C;
(aa)₄₆ is F, Y or a deletion in said sequence;
(aa)₄₇ is I, V, A, L, R, or a deletion in said sequence;
(aa)₄₈ is E, I, Q, T, V, R, N, H, S, C, a deletion in said sequence, D, Y or K;
(aa)₄₉ is Y, F, S, G, a deletion in said sequence, or M;
(aa)₅₈ is A, S, M, a deletion in said sequence, V, P, I, or N;
(aa)₆₃ is D, Q, W, E, Y, V, N, a deletion in said sequence, K, S, P, G, or T;
(aa)₆₇ is I, F, L, a deletion in said sequence, Q, S, E, V, P, or M;
(aa)₆₉ is G, S, D, Q, P, K, a deletion in said sequence, Y, I, T, or N;
(aa)₇₃ is V, M, A, T, N, F, I, C, L, a deletion in said sequence, Q, or K;
(aa)₇₅ is V, I, a deletion in said sequence, M, L, C, P, Y or E;
(aa)₇₈ is E, A, N, a deletion in said sequence, L, G, S, F, H, R, K, T, P, Q, O, or M;
(aa)₈₀ is R, D, G, a deletion in said sequence, P, Q, E, I, N, K, or T;

(aa)₁, (aa)₅, (aa)₆, (aa)₈₋₁₃, (aa)₁₆, (aa)₂₃, (aa)₂₆, (aa)₂₈, (aa)₃₃, (aa)₃₈, (aa)₄₁, (aa)₅₀, (aa)₅₅₋₅₇, (aa)₅₉, (aa)₆₀₋₆₂, (aa)₆₄₋₆₆, (aa)₆₈, (aa)₇₀, (aa)₇₁, (aa)₇₃, (aa)₇₅, (aa)₇₆, (aa)₇₈, (aa)₇₉ and (aa)₈₁ are each, independently, one member selected from the group consisting of the amino acids and deletions in said sequence;

(aa)₁₆ and (aa)₁₇ are linked to each other via (i) a covalent bond or (ii) up to three amino acids selected from the group consisting of the amino acids (aa)₅₉ and (aa)₆₀ are linked to each other via (i) a covalent bond or (ii) one amino acid selected from the group consisting of the amino acids;

(aa)₁₉ and (aa)₂₀ represent at least two and up to four members selected from the group consisting of the amino acids and deletions in said sequence;

(aa)₂₉₋₃₁ represent at least three and up to five members selected from the group consisting of the amino acids and deletions in said sequence;

(aa)₃₄₋₃₇ represent at least five and up to seven members selected from the groups consisting of the amino acids and deletions in said sequence; and (aa)₅₁₋₅₄ represent at least four and up to seven members selected from the group consisting of the amino acids and deletions in said sequence.

Preferably, in the above compound:
(aa)₂ is L, I, or V;
(aa)₃ is F, Y, L, I or V;
(aa)₄ is V, I, or L;
(aa)₇ is V, I, or L;
(aa)₁₄ is E, D, K, or N;

(aa)₁₅ is S, E, K, or D;
(aa)₁₇ is L, I, or V;
(aa)₁₈ is D, E, K, R, Q, N, or Y;
(aa)₂₁ is F, Y, W, or H;
(aa)₂₂ is D, E, K, R, Q, N or Y;
(aa)₂₄ is Y, F, or W;
(aa)₂₅ is G;
(aa)₂₇ is L, I or V;
(aa)₃₂ is L, I or V;
(aa)₃₉ is G;
(aa)₄₀ is R, H, or a deletion in said sequence;
(aa)₄₂ is R, K, or H;
(aa)₄₃ is G;
(aa)₄₄ is Y, or F;
(aa)₄₅ is A, or G;
(aa)₄₆ is F, or Y;
(aa)₄₇ is L, I, or V;
(aa)₄₈ is D, E, K, R, Q, N, or Y;
(aa)₄₉ is Y or F;
(aa)₅₈ is A;
(aa)₆₃ is D, Q, W, E, a deletion in said sequence, or K;
(aa)₆₇ is L, I, or V;
(aa)₆₉ is G;
(aa)₇₃ is V, M, A, F, I, C, o r L;
(aa)₇₅ is L, I or V;
(aa)₇₈ is A; and
(aa)₈₀ i s D, E, K, R, N, Q, or a deletion in said sequence.

The present invention also provides a compound of formula (VIII):

(component X)—(cognate RNA)

wherein
(i) said component X is covalently bound to said cognate RNA, said component X being one member selected from the group consisting of labelled materials; and
(ii) said cognate RNA is a polyribonucleotide comprising at least the sequence:

5' GGGAGAUACCAUGAUCACGAAGGUGGUUUUCCC 3' and up to the sequence of U1 RNA.

The present invention also provides a compound of formula (IX):

(component Y)—(cognate RNA)

wherein:
(i) said component Y is covalently bound to said cognate RNA, said component Y being one member selected from the group consisting of DNA probes, RNA probes, antigens, and antibodies; and
(ii) said cognate RNA is a polynucleotide comprising at least the sequence:

5' GGGAGAUACCAUGAUCACGAAGGUGGUUUUCCC 3' and up to the sequence of U1 RNA.

This invention also provides modifications of the design of the 70K RNA binding domain to alter the affinity and specificity of its recognition of target RNA. Such modifications of the domain are produced by deletion mutagenesis (FIGS. 4 and 5) or site-directed alterations of specific amino acid residues within the domain (examples are summarized in FIG. 7).

For example, deletions of amino acids from the ends of the RNA binding domain decrease binding affinity (70K constructs ending at residues 209 or 202) or abolish binding completely (e.g., constructs starting at residues 100 or ending at 197).

Within the RNA-binding domain site-specific alterations at aromatic positions allow full binding to U1 RNA (e.g., the phenylalanine residue at position 106 can be replaced with tyrosine or with any branched-chain aliphatic residue—leucine, isoleucine, or valine; also, the tyrosine residues at positions 146 and 151 can be replaced with phenylalanine).

In contrast, substitution with other amino acid residues alters the binding activity (e.g., replacement of tyrosines 146 or 151 with aliphatic residues) and substitution of some sites with any amino acid alters the activity (replacement of phenylalanine 148 with any other amino acid residue). This approach shows that aromatic residues are important to the specificity and activity of the RNA binding domain and identified amino acid residues that can be altered in the design of novel RNA binding domains.

This illustrates the ability to alter the specific recognition properties of an RNA binding protein so as to modify the affinity and specificity of an RNA binding domain.

For example, one can use the ribozyme Tet 1.0 (Zaug et al, *Nature* (1986) 324:429–433) and a modified RNA binding domain selected on the basis of its characteristic properties of RNA specificity to design a binding reaction between the protein and the ribozyme. This involves stepwise alterations of RNA bases in the ribozyme that do not affect its enzymatic activity but which progressively come to match those required for recognition by the RNA binding protein.

Likewise, amino acid residues in the RNA binding domain can be altered step-wise and tested for binding to the ribozyme using the binding methods disclosed herein. When a point is reached where both ribozyme activity and RNA binding of the protein are at sufficient levels, a novel ribonucleoprotein with defined enzymatic activity is obtained.

This is to be practiced by attachment of the U1 RNA binding site onto the ribozyme allowing recognition by the 70K RNA binding domain. Progressive alterations in the U1 RNA and the 70K RNA binding domain are produced with the goal of maintaining the binding specificity while optimizing the efficiency of ribozyme function. A variety of alternative approaches are available in the event that designs based upon the specificity of 70K for stem-loop 1 of U1 RNA altered the function of the ribozyme.

For example, the La protein contains an amino acid sequence motif in the RNA binding domain that is similar to that of the 70K protein (FIG. 6 and Chambers et al, *J. Biol. Chem.* (1988) 263: 18043–18051). The La protein has specificity for recognition of 3' terminal uridylate residues on RNA and thus, fewer constraints on RNA sequence recognition than the 70K protein (i.e. less specific). Stefano, *Cell* (1984) 36: 145–154. A ribozyme can be modified at its 3' terminus as to bind the La protein binding domain without affecting the enzymatic activity of the ribozyme.

To modulate the strength of binding, the length of the uridylates can be adjusted or other RNA bases can be substituted in the sequence. Mutations could be introduced into the RNP octamer (for example aliphatic substitutions for aromatics as demonstrated for 70K RNA binding domain in FIG. 7) to modulate the affinity of the protein for the RNA sequence.

Thus, the design and creation of novel ribonucleoproteins with specific enzymatic or diagnostic functions are numerous and varied based upon the recognition of specific RNA sequences by some members of the family of homologous proteins defined in FIG. 6.

In another embodiment, the present proteins can be used to control eukaryotic cell growth, i.e. to either up regulate or down regulate the rate of expression of genetic information in a eukaryotic cell. In this embodiment, the rate of expression of genetic information in a eukaryotic cell is up regulated (i.e., increased) by increasing the concentration of whole human 70K U1 snRNP protein in a cell when it is rate-limiting. This can be achieved by administering to a patient an appropriately modified (vide infra) native 70K protein, whereupon it infects a target cell, increasing its rate of genetic expression.

The rate of expression of genetic information in the eukaryotic cell can be down regulated (i.e., decreased) when at least one protein of sequences (I), (II) or (III), or modifications thereof are introduced into the cell. In this embodiment, an appropriately modified protein of sequence (I), (II) or (III), or appropriate modification (vide infra) containing at least 35% homology to sequences (I), (II) or (III) is administered to a patient, whereupon it infects a target cell, decreasing or stopping (depending on dosage) its rate of genetic expression.

For example, the expression of the 70K RNA binding domain in vivo as part of a fusion protein or alone allows the up or down regulation of RNA splicing. This regulatory function can be used in a site-specific delivery system to inhibit tumor cell growth, alter the expression of tissue-specific growth controlling substances or to destroy defective cells involved in disease processes. By these methods and using the inventions outlined here one can create novel functional or disfunctional ribonucleoproteins in vivo. In a manner similar to that described here, the eukaryotic cell may use naturally occurring homologs of 70K protein to regulate tissue-specific or developmentally-specific genes (Amrein et al, *Cell* (1988) 55: 1025–1035; Goralski et al, *Cell* (1989) 56: 1101–1108; Query et al, *Cell* (1989) 57: 89–101). Thus, patterns of alternative splicing may be modulated by expression of modified forms of the 70K protein.

Inhibition of growth of cells producing pathogenic substances, viruses or uncontrolled growth:

The processing of messenger RNAs encoding growth factors or other secreted proteins depend upon the normal function of the 70K protein. Increased levels of the 70K protein allows more targeted gene expression and decreased levels of intracellular 70K would allow 80 to 100% lower production of factors required for normal growth.

In recent years various methods have been developed for delivery and specific targeting of genes into eukaryotic cells. For example, retroviral vectors for transfer of genetic information into tissues (Eglitis et al, *Biotechniques* (1988) 6: 608–614; Miller et al, *Biotechniques* (1989) 7: 980–990) allows the targeting of specific genes to specific cell types. Likewise, liposome mediated transfer of genes to targets allows the expression of defined proteins in specific tissues (Wang et al, *Proc. Natl. Acad. Sci. (USA)* (1987) 84: 7851–7855; Mannino et al, *Biotechniques* (1988) 6: 682–690). These approaches are used to express 70K sense or antisense molecules in eukaryotic cells as a method to regulate gene expression.

For example, the 70K RNA binding domain can be expressed in specific tumor cells or in cells producing viruses or pathogenic antibodies using a retroviral or liposome-mediated transfer. The targeting to these particular cells depends upon the specific receptors designed into the vehicle using standard methods (Miller et al, *Biotechniques* (1989) 7: 980–990). The 70K domain without the associated sequences at residues 241 to 437 is functionally debilitated and unable to act during spliceosome assembly. Thus, expression of the binding domain alone results in the endogenous U1 RNA being bound and sequestered from proper function. This type of dominant suppression of function disrupts the normal functioning of cell proteins in HIV infected cells (Malim et al, *Nature* (1989) 338:254–257; Green et al, *Nature* (1989) 338: 200–201; and Hanly et al, *Genes and Develop.* (1989) 2:1534–1544. The tissue that expresses the defective 70K protein binding domain inhibits a cell from normally splicing its pre-messenger RNAs and cease growing. In the case of the targeted tumor, the ability of the tumor to undergo rapid growth is retarded or stopped.

The other approach to inhibition of cell growth is to block the production of endogenous 70K protein through the expression of antisense to 70K mRNA (van der Krol et al, *Biotechniques* (1988) 6: 958–976). Using retroviral and liposome-mediated gene transfer to specific tissues such as tumor cells, B cells expressing pathogenic antibodies or virally infected cells, the 70K antisense RNA is produced to levels equal to or up to 10 fold in excess of the endogenous levels of 70K mRNA.

Subsequent inhibition of production of new 70K protein blocks the formation of the U1 snRNP which is important for splicing reactions at the 5' splice site. Failure to assemble the spliceosome or to correctly recognize the 5' splice site because of decreased levels of 70K results in catastrophic shutdown of the processing and transport of messenger RNA from the nucleus to the cytoplasm. Thus, cells targeted in this manner are limited in their ability to grow and express their genetic information.

An example of the application of the above approach in the area of immune regulation involves destruction of immune cells that produce damaging autoantibodies in rheumatoid arthritis and other autoimmune diseases. Expression of the RNA binding domain or the 70K antisense sequences can be used to block the process of antibody expression by delivery to specific immune cells.

For example, B or T cells expressing on their surface, autoantibodies for the human Ro protein that is associated with systemic lupus erythematosus, Sjogren's syndrome, congenital fetal heartblock and rheumatoid arthritis overlap, can be targeted using specific recombinant autoantigens reactive with the autoantibodies.

This invention, exemplified in terms of the 70K RNA binding domain above, with greater exemplary detail being given below, can be accordingly practiced to the RNA binding domains of any other member of the family shown in FIG. 6. Thus, without major modifications or new inventive steps, other than those described herein, this invention can be readily practiced with other members of this family of proteins based upon the facts disclosed. In fact, this invention has now been practiced in the inventor's laboratory in a manner analogous to that disclosed here using the La, 60K Ro and U1 snRNP-A proteins.

The cells which may be used in the practice of the methods outlines above, may be eukaryotic or prokaryotic cells.

Having generally described this invention, a further understanding can be obtained by reference to certain specific examples which are provided herein for purposes of illustration only and are not intended to be limiting unless otherwise specified.

The text provided below largely corresponds to the inventors' publication, Cell (1989) 57: 89–101. This document, the documents cited therein, and the documents cited in this text, are all hereby incorporated by reference herein.

The 70K U1 RNA-associated protein is a component of the U1 small nuclear ribonucleoprotein (snRNP) complex. Several snRNPs have been implicated in the removal of intervening sequences during precursor messenger RNA splicing. The U1 snRNP, in particular, has been shown to interact with the 5' splice site, at least in part by base pairing of this site with the 5' terminal 10 nucleotides (nt) of U1 RNA. The human U1 snRNP is composed of the 165 nt U1 RNA and two classes of proteins: U1-specific proteins, 70K, A and C; and the Sm complex, consisting of six U snRNP-common proteins.

Interactions between the 70K protein and U1 RNA have been studied previously by immunoprecipitation of nuclease-treated cell extracts and by injection of RNA into Xenopus oocytes. These studies have suggested that the 70K protein, as well as the A and, perhaps, C proteins contact the 5' half of U1 RNA. Although in vivo studies have the advantage of examining the snRNP in the presence of all protential structural proteins, the resulting complexity makes it difficult to elucidate the details of RNA-protein interaction within the snRNP. Recently, the boundaries of contact of the 70K protein on U1 RNA have been determined to involve 31 nucleotides in stem-loop I.

Recombinant clones of the human 70K protein have been isolated by screening cDNA expression libraries with antibodies from patients with autoimmune disorders Differences among these cDNA sequences have led to protein sizes predicted to be as large as 614 amino acids although Northern blot analysis in our laboratory has not been consistent with this assignment. More recently, it has been have suggested that the protein may be smaller than 614 amino acids.

We have reconstituted the complete 70K protein and U1 RNA in vivo and found that the specificity of this association was maintained through progressive deletion of the protein, identifying a binding domain of 111 amino acids of the 70K protein that were required. Further deletion resulted in no detectable reconstitution. This RNA binding domain encompasses an 80 amino acid motif that is common to many other RNA-associated proteins. Contained within this motif is a central sequence representing the RNP consensus octamer. We have now examined general features of this RNA recognition motif (RRM) in other RNA-associated proteins and of the highly charged carboxy-terminal domain of the 70K protein that may relate to its function in pre-mRNA splicing.

Results:

A 52 kd Primary Translation Product Represents the 70K Protein:

We previously reported the isolation of cDNA encoding a region of the human U1 snRNP 70K protein that is similar in amino acid sequence to a portion of p30$^{gag}$ protein of type C retroviruses. This cDNA was used to screen libraries of human placental, endothelial, and fibroblastic origin (Experimental Procedures). Several clones of 1.7 kb were isolated, which corresponded in size to the mRNA from HeLa cells by Northern analysis. These cDNAs contained an open reading frame (ORF) of 1.3 kb that could encode a protein with predicted molecular weight of 52 kd. Repeated screening of these libraries yielded no further 5' sequence, and consistently produced clones with similar 5' ends. In addition, sequence determination of cDNAs derived from the placental, endothelial, and fibroblastic tissues showed in-frame stop codons 5' to the ORF, suggesting that the 1.3 kb ORF represents the complete coding sequence. One placenta-derived clone, PL40, was chosen for further study. This cDNA was inserted into a pGEM-3Zf(+) vector with transcription directed by the T7 promoter. Transcripts were translated in vitro in a rabbit reticulocyte lysate, and the resulting protein was analyzed. The translation product of PL40 comigrated with the authentic 70K protein from HeLa cells at an apparent molecular weight of 70 kd and was reactive with anti-(U1)RNP antibodies.

Because of this large difference between the apparent and predicted molecular weights of the PL40 in vitro translation product, we determined whether sequences outside of the 1.3 kb ORF were utilized for translation. First, the 3' untranslated region of the PL40 cDNA was truncated by digestion with MluI, which cuts 27 nucleotides 3' to the TAG stop codon of the 1.3 kb ORF. In vitro transcription and translation of this truncated cDNA yielded a product that comigrated with the authentic protein indicating that the increase in apparent molecular weight was not due to read-through translation. Next, the majority of the predicted 5' untranslated region of P140 (nt −105 to −1) was deleted; in vitro transcription and translation of this mutant again produced a protein of 70 kd that comigrated with the authentic protein showing that there was no significant translation of the predicted 5' untranslated region of PL40. Finally, we altered the predicted translation initiation codon for the 1.3 kb ORF by oligonucleotide-directed mutagenesis. The sequence of this site, GGCAAGAUGA, is a relatively poor

TABLE 2

Apparent and Predicted Molecular Weights of Truncated and Deleted 70K Polypeptides

| Template | Endonuclease Used to Digest Template | Amino Acids Contained | Predicted Protein MW[a] | Observed Protein M$_r$[a] | Percent Aberrant Migration[b] |
|---|---|---|---|---|---|
| FLΔ5'UT | BamHl | 1–437 | 51.56 | 70.1 | 36.0 |
| FLΔ5'UT | MluI | 1–437 | 51.56 | 70.1 | 36.0 |
| FLΔ5'UT | SacI | 1–333 | 39.71 | 50.6 | 27.4 |
| FLΔ5'UT | ApaI | 1–299 | 35.91 | 44.4 | 23.7 |
| FLΔ5'UT | SmaI | 1–259 | 30.79 | 38.3 | 24.5 |
| FLΔ5'UT | KpnI | 1–197 | 23.30 | 26.4 | 13.5 |
| 92–437 | BamHl | 1–10, 92–437 | 41.77 | 56.2 | 34.5 |
| 134–437 | BamHl | 1–10, 134–437 | 36.86 | 50.8 | 37.8 |
| 145–437 | BamHl | 1–10, 147–437 | 35.51 | 50.3 | 41.8 |
| 280–437 | BamHl | 1–10, 280–437 | 19.18 | 31.3 | 63.3 |

TABLE 2-continued

Apparent and Predicted Molecular Weights of Truncated and Deleted 70K Polypeptides

| Template | Endonuclease Used to Digest Template | Amino Acids Contained | Predicted Protein MW[a] | Observed Protein $M_r$[a] | Percent Aberrant Migration[b] |
|---|---|---|---|---|---|
| 291–437 | BamHl | 1–10, 291–437 | 17.74 | 30.0 | 69.2 |
| 341–437 | BamHl | 1–10, 341–437 | 12.41 | 20.6 | 66.0 |

[a]Expressed in kilodaltons.
[b](Observed-predicted)/predicted.

translation initiation sequence compared with the consensus sequence of Kozak (1981, 1984). This site was changed to an optimal sequence, GGCGCCACCAUGG which resulted in increased efficiency of translation of the same size protein. Although initiation at a non-AUG codon has not been excluded, our results rule out the possibility of a significantly longer translation product,-because deletion of sequences immediately 5' and 3' to the ORF do not affect the size of the translation product. The next nearest AUG in any reading frame in 198 nucleotides in the 3' direction; therefore, these results strongly suggest that the AUG at nt 1 is the initiation site for a 52 kd protein product that migrates as a 70 kd protein in SDS-PAGE.

Aberrant Migration is Mainly Due to the Charged Carboxyl Terminus:

Anomalous electrophoretic migration of proteins is not uncommon and has been observed with other translation products To investigate specific regions responsible for this aberrant migration, we used restriction enzymes to cleave the template DNA at various positions within the coding sequence, and subjected the cleaved templates to transcription and translation. As the highly charged carboxyl terminus was removed (see FIG. 4), the degree of aberrant migration decreased significantly (Table 2), indicating that the carboxyl terminus is chiefly responsible for the aberrant migration. In addition, we investigated the mobility of internally deleted mutants (described below, FIG. 4). As amino-terminal regions were deleted and the carboxyl terminus constituted a larger proportion of the polypeptide, the degree of aberrant migration increased (Table 2). Thus, the carboxyl terminus of the 70K protein is responsible for much of the aberrant migration observed in SDS gels, although some of the anomaly may result from other regions of the protein, such as the amino terminus, which includes 50 amino acids with a strikingly high proline content (20%).

U1 RNA-Specific Binding by the 70K Protein:

As an approach to determining the structure and function of the 70K protein, we investigated whether the recombinant 70K protein could interact directly with U1 RNA. For RNA binding, we used either 70K-LacZ fusion protein or in vitro 70K translation products. The 70K-LacZ fusion protein, purified from E. coli and solubilized in 4M urea, was incubated with deproteinized HeLa whole cell RNA and immunoprecipitated with anti-s-galactosidase monoclonal antibody, and the co-precipitated RNA was analyzed. Similarly, the in vitro translation product of the complete 70K protein was incubated with deproteinized HeLa RNA and immunoprecipitated with anti-(U1)-RNP serum, and the co-precipitated RNA was analyzed. Both the fusion protein and the translation product selectively bound a single RNA species from the total HeLa cell RNA.

This RNA species comigrated with U1 RNA by elution and subsequent immunoprecipitation with an anti-U1 RNA-specific antibody (Wilusz and Keene, 1986; Deutscher and Keene, 1988) and by hybridization to U1 DNA Specific RNAs were not precipitated in the absence of antibody or in the absence of 70K-LacZ fusion protein. Fusion proteins containing other autoantigenic sequences as controls, unprogrammed in vitro translation (lacking exogenous mRNA), or antisera of other autoimmune specificities did not result in precipitation of U1 RNA. In addition, both the 70KLacZ fusion protein and the 70K in vitro translation product bound U1 RNA synthesized in vitro. We conclude that the recombinantly produced 70K-LacZ fusion protein and in vitro translated 70K protein interact directly and specifically with U1 RNA.

The U1 RNA Binding Domain of the 70K Protein:

To investigate the regions of the 70K protein that interact with U1 RNA, we used restriction enzymes to truncate the 70K cDNA from the 3' end and exonuclease III to create 5' deletions within the 70K cDNA (described in Experimental Procedures below). One series of proteins deleted progressively from the carboxyl terminus, and another series deleted from the amino terminus, were translated in vitro (FIG. 4). The ability of each translation product to react with similar efficiency with an excess of anti(U1)RNP serum was verified by immunoprecipitation, thus demonstrating that multiple autoimmune epitopes are present along the 70K protein.

Each in vitro translated protein was incubated with total HeLa cell RNA and immunoprecipitated with anti-(U1)-RNP serum, and the co-precipitated RNA was analyzed. For the carboxy-terminal deletions, polypeptides containing amino acids 1–437, 1–333, 1–299, 1–259, 1–251, 1–236, and 1–216 all selectively coprecipitated U1 RNA, whereas those containing amino acids 1–197 and 1–52 did not. Polypeptides 1–109 and 1–202 coprecipitated U1 RNA at very low efficiency, compared with controls (this was consistent with several repetitions of the experiment). As amino-terminal regions were deleted, polypeptides 92–437 coprecipitated U1 RNA, but polypeptides 134–437 or polypeptides representing larger amino-terminal deletions did not. Thus, we could remove amino acids 1–91 or amino acids 217–437 while retaining specific U1 RNA binding activity (see FIG. 4).

We next examined polypeptides deleted from both the amino- and carboxy-termini. Polypeptides 92–259, 92–236, and 92–216 specifically co-precipitated U1 RNA. Smaller polypeptides (134–259, 161–259, 92–197) did not detectably precipitate U1 RNA, and polypeptides 92–209 and 92–202 co-precipitated small amounts of U1 RNA. Although the binding of a small protein fragment to U1 RNA might interfere with its simultaneous recognition by an anti-(U1)RNP antibody and obscure our detection of binding (see below), we can conclude that residues 92–216 contain a U1 RNA-specific binding domain.

To exclude the involvement of proteins other than 70K in the in vitro translation binding reactions, we also tested the ability of a β-galactosidase fusion protein containing a sequence overlapping the region identified above at residues 92–216 of the 70K protein to bind U1 RNA. Amino acids 35–216 were fused to LacZ and expressed in E. coli. Fusion protein was purified incubated with total HeLa cell RNA, and immunoprecipitated with anti-β-galactosidase antibody. The ability to co-precipitate U1 RNA demonstrated that this portion of 70K as a purified fusion protein also selectively bound U1 RNA in vitro. As shown in FIG. 3, the 70K sequences of the smallest LacZ fusion protein that bound U1 RNA (amino acids 35–216) overlapping the smallest translation product that bound efficiently (92–216) suggests that the U1 RNA binding domain is encompassed by amino acids 92–216.

Mobility Shift Analysis of the Reconstituted Complex:

As described above, high efficiency of coprecipitation of U1 RNA was possible using fragments 92–236 and 92–216, but co-precipitation was inefficient using translation fragments 92–209 or 92–202 (summarized in the right hand column of FIG. 4). Resolution of the U1 RNA binding domain of the 70K protein below the region 92–216 using the antibody precipitation assay could potentially be compromised by competition between U1 RNA and the antibody or by progressive loss of epitopes on the protein fragments. As an alternative assay that does not involve recognition of a protein-RNA complex by antibody, we analyzed reconstituted 70K protein-U1 RNA complexes by native gel electrophoresis. $^{35}$S-labeled 70K polypeptides were translated in vitro, incubated with various RNAs in a binding buffer (Experimental Procedures), and immediately electrophoresed on a native polyacrylamide gel. p FIG. 5 panel B shows the results obtained when peptide residues 92–236 were incubated with tRNA (lane 1), U1 RNA (lane 2), U1δL1 (U1 RNA deleted of the loop 1, which is required for interaction with the 70K protein (lane 3)), and β-globin RNA (lane 4). The faster migrating species (lane 1, lower arrow) represents the translated 70K peptide. (The unmarked band at the bottom of each lane represents $^{35}$S-methionyl tRNA that was formed in all the in vitro translation reactions.)

The presence of U1 RNA created a complex of slower mobility (lane 2, upper arrow) not observed with other RNAs and a concomitant loss of the faster migrating species seen in lanes 1, 3, and 4 (lower arrow). It is possible that the faster migrating species represents a complex of 70K protein with competitor RNAs that were specifically displaced upon addition of U1 RNA. No similar species or shifts in mobility were observed from products of unprogrammed translations (panel A) or from other control translation products. Thus, binding activity can be deleted as an altered migration of $^{35}$S-labeled translation product in the presence of specific RNA, as similarly described for DNA binding proteins (Hope and Struhl, 1985).

We next assayed smaller 70K fragments for their abilities to form the slower migrating complex in the presence of U1 RNA using native gels. Polypeptides containing amino acids 92–216, 92–209, and 92–202 (FIG. 5, panels C, D and E) each formed complexes of slower migration in the presence of U1 RNA but not in the presence of other RNAs, although a reduced proportion of the 92–202 species formed stable complexes compared with the larger peptides. Amino acids 92–197(panel F) or smaller peptides failed to form the specific complex with U1 RNA. Other 70K polypeptides that encompassed the 92–202 region (1–236, 1–216, 1–909, 1–202; FIG. 4) all formed the specific complex with U1 RNA; polypeptides that did not contain the 92–202 region (1–197, 1–194, 1–189, 1–179, 101–216 161–259; FIG. 4) did not form a complex of altered mobility in the presence of U1 RNA or other RNAs.

These findings confirm the assignment of the RNA binding component of the 70K protein to within amino acid residues 92–216, but also demonstrate further reduction to 92–202. Although the efficiency of binding of amino acids 92–202 was diminished relative to larger fragments, it retained the specificity of the interaction; deletion of the carboxy terminus past residue 202 resulted in no detectable binding. Thus, we conclude that the minimal binding domain of the 70K protein to U1 RNA residues in the 111 amino acids between positions 92 and 202, inclusive (FIG. 2).

Through progressive deletion analysis of the protein component, we have shown that U1 RNA is specifically recognized and stably bound by a region of 70K that encompasses the RNP octamer sequence as well as a larger consensus sequence motif. Based upon the functional test of specific RNA binding activity, we define this 111 amino acid region as a distinct domain of the 70K protein. This sequence shows similarity in a core of 80 amino acids to many other RNA-associated proteins and, therefore, defines a common motif for sequence-specific recognition of RNA (FIG. 6).

FIG. 6 sets out conserved features within an RNA recognition motif. Regions of sequence similarity among several RNA-associated proteins and the U1 RNA binding domain of the 70K protein are arranged to create the best alignment of conserved residues within subdomains of the 80 amino acid region. Highly conserved positions are shaded, * being more conserved than +, and less conserved positions are not shaded. Amino acids are grouped acording to Taylor (1987) .#1, #2, etc., represent different domains within the same protein; ac, acidic residue (D, E); ba basic residue (K, R, H); ch, charged residue (D, E, K, R, H); ho, hydrophobic residue; al, branched-chain aliphatic residue (L, I, V); ar, aromatic residue (F, Y, W, H); np, nonpolar residue; po, polar residue; aa, amides or acids (E,Q,D,N); ab, amides, acids or bases (E,Q,D,N,K,R); capital letters are the standard amino acid abbreviations; x, unassigned.

RNP consensus octamer (Adam et al., 1986; Swanson et al., 1987); human U1snRNP-70K (Theissen et al., 1986; Spritz et al., 1987 Query et al., 1989a); Xenopus U1snRNP 70K (Elzevodt et al., 1988); U1snRNP-A (Sillekens et al., 1987); U2snRNP-B" (Habets et al., 1987); Ro RNP-60K (Deutscher et al., 1988); UP2 (Lahiri and Thomas, 1988; Merrill et al., 1986); hnRNP C1/C2 (Swanson et al., 1987); human La (Chambers and Keene, 1985; Chambers et al., 1988); bovine La (Chan et al., 1989); E. coli rho protein (Pinkham and Platt, 1983); T4 gp32, bacteriophage T4 gene 32 protein (Krisch and Allet, 1982); yeast PABP, poly(A) binding protein (Adam et al., 1986; Sachs et al., 1986); human PABP (Grange et al., 1987) SSB1, yeast single-stranded nucleic acid binding protein (Jong et al., 1987); fly p9, Drosophila protein p9 containing pen repeat elements (Haynes et al., 1987); fly ELAV, Drosophila neuron-specific embryonic-lethal abnormal-visual system protein (Robinow et al., 1988); Fly bicoid (Rebagliati, 1989); hnRNP-A1 (Riva et al., 1986); HDP, rat helix-destabilizing protein (Cobianchi et al, 1986); UP1, calf thymus helix-destabilizing protein (Williams et al., 1985); hamster nucleolin, (Lapeyre et al., 1987; Bugler et al); mouse nucleolin (Bourbon et al., 1988); rat nucleohn (Chang et al., 1988); Xenopus nucleolin (Caizergues-Ferrer et al., 1989).

The 70K cDNA:

We determined that the open reading frame of the 70K cDNA encodes a 437 amino acid protein that has a calculated molecular weight of 52 kd. Aberrant migration at $M_r$ 70 kd in SDS gels is due to the highly charged carboxyl half of the protein. Thus, we conclude that sequences upstream of amino acid 178 reported by Theissen et al. (1986) are not required to encode the full-length 70K protein. Although it remains possible that the additional sequence reported by Theissen et al. represents an alternatively spliced 70K-related protein, we believe this to be unlikely, as our cDNAs obtained from multiple tissues contain an in-frame stop codon 5' to the 437 amino acid ORF. This stop codon also is present in the sequence of Theissen et al., but in a different reading frame.

The RNA Recognition Motif (RRM):

We delineated three regions of interest in the 70K protein. These include the sequences between amino acids 50 and 70 that are similar to and cross-reactive with retrovirus p30$^{gag}$ protein (Query and Keene, 1987), the U1 RNA binding domain between residues 92 and 202, and the highly charged carboxyterminal half of the molecule that is responsible for much of the aberrant electrophoretic migration of the 70K protein. The U1 RNA binding domain contains several potential subdomains with striking similarity to other RNA-associated proteins, especially when conservative substitutions are taken into consideration (FIG. 6).

Strong conservation is evident in the previously described RNP octamer, in which three of the eight conserved amino acids are aromatic (subdomain III). upstream of the octamer sequence in these proteins are two additional potential subdomains, each surrounding a highly conserved aromatic residue. In subdomain I, this aromatic residue (position 3) is flanked by aliphatic amino acids and followed by a pair of acidic residues (14, 15), while in subdomain II, a larger area of conservation includes aliphatic (17, 27, 32), polar (18, 22), and aromatic residues (21), as well as a highly conserved glycine (25). The conservation of the aromatic residues and the amino acids flanking them in many presumed RNA binding proteins from yeast to human suggests an important common functional role for this motif. Experimental evidence for proximity to RNA involving a similar region has recently been provided for the hnRNP-A1 protein, in which phenylalanines were UV-cross-linked to oligodeoxythymidine (Merrill et al., 1988). In addition, a fragment of the preribosomal RNA-associated protein, nucleolin, which contained an RNP consensus octamer, was shown to interact with ribosomal RNA when bound to nitrocellulose (Bugler et al., 1987).

Subdomain IV also has several conserved residues (aliphatics [67, 74] and glycine [69], but appears to lack the relatively discrete blocks of conservation apparent in sub-domains I-III. Additional positions across the U1 RNA binding domain show less conservation (total of 31 positions unshaded within the motif in FIG. 6), suggesting that structural or functional roles specific to individual proteins may reside in these positions. Although there are not guidelines for RNA-protein interactions that predict determinants of RNA binding specificity, we suspect that the specificity of RNA recognition by different RNA binding proteins that contain this recognition motif is determined by spacings between the conserved amino acids and by differences among the less conserved residues.

Implications for RNA Binding Domains:

The domain demonstrated here for the 70K protein includes additional amino acids that reside outside the motif and are required for the interaction with U1 RNA. Thus, the RRM alone is not sufficient for U1 RNA binding in the 70K protein (compare shaded regions in FIG. 2). Proteins containing more than one RRM, such as poly(A) binding protein, nucleolin, and the U1 RNA-associated A protein (FIG. 6), may not have multiple functional RNA binding domains. These regions could be vestiges of a gene duplication event from an ancestral protein that have retained structural similarities but have diverged in function. For example, the A protein could be suggested to be divalent for RNA binding because it contains two RRMs; but, until binding is demonstrated for each region, these separate motifs cannot be assumed to be complete and independent binding domains. Similarly, the presence of a single RRM may not always confer all of the properties necessary for a specific interaction with RNA.

Implications for Autoimmunity:

As depicted in FIG. 6, the amino acid sequence motif is conserved among several RNA-associated proteins; and, as demonstrated in our recent studies of direct RNA binding (Chambers et al., 1988; Deutscher et al., 1988; Lutz-Freyermuth and Keene, Mol. Cell Biol (1989) 9: 2975–2982, several of these are specific RNA binding proteins. Interestingly, five of these proteins (70K, A, B", La, and Ro) are autoantigenic for patients with lupus erythematosus and related diseases; three of these proteins, 70K, La, and Ro, are among the most prevalent autoantigens (Bernstein et al., 1984). It is possible that this RRM represents or encompasses an autoimmune cross-reactive determinant. There is little evidence, however, for immunological cross-reactivity in this region. The A and B" proteins have been demonstrated to cross-react (Habets et al., 1985; Reuter and Luhrmann, 1986), and this may occur in the region of the motif (Sillekens et al., 1987). Widespread presence of autoimmune cross-reactive determinants in the RRM seems unlikely because not all of the human proteins shown in FIG. 6 have been reported to be autoantigenic, and because other proteins associated with U RNAs are autoantigenic but do not contain the RRM (U1 snRNP-C, Sillekens et al., 1988; Sm-D, Rokeach et al., 1988; Sm-E, Wieben et al., 1985; and U2 snRNP-A', Fresco and Keene, submitted). However, it is conceivable that some cross-reactive responses exist early in the evolution of autoimmunity but are not predominant at later stages in the course of the disease (Query and Keene, 1987). Further study will be required to address this interesting, and perhaps only, primary sequence similarity among some common autoantigens.

The Carboxy-Terminal Charged Regions:

The carboxy-terminal half of the 70K protein consists of two charged regions (amino acids 241–303 and 348–389, underscored in FIG. 2) that are separated by a proline/glycine-rich (18%/25%) stretch of 45 residues. The charged regions are 51% and 48% arginine, respectively, with repetitions of arg-glu, arg-asp, and arg-ser. The carboxy-terminal 48 amino acids are also glycine-rich (25%) and may be structurally flexible. Although the 70K protein has not been shown to be involved directly in mRNA splicing, it does interact with U1 RNA near the 5' end that base pairs with pre-mRNA. In a related study (Query et al., Mol. Cell. Biol. (1989) 9: 4872–4881) we demonstrated that the 5' end of U1 RNA is not required for 70K binding. We have demonstrated in this paper that the arginine-rich regions of the 70K protein are not necessary for binding to U1 RNA. Thus, the 5' end of the U1 RNA and the C-terminus of 70K protein are both available for interaction with other structures. The charged carboxy-terminal regions probably extend away from the U1 RNA binding domain, and may exist as two charged domains flanked by glycine-rich hinges. It is possible that this region of the 70K protein contacts other RNAs but with less specificity than that demonstrated for the U1 RNA-70K interaction.

These two charged regions are similar to the Drosophila proteins "suppressor of white apricot" su(w$^a$), Chou et al., 1987; Zachar et al., 1987) "transformer" (tra, Boggs et al., 1987), and "transformer-2" (Amrein et al., 1988; Goralski et al., 1989) and to a recently identified mouse MHC gene product of unknown function, WL623 (Levi-Strauss et al., 1988). Because of the internal repetitions of arg-glu, arg-asp, and arg-ser, these proteins are similar in several frames of alignment. In the best alignment frame, amino acids 241–303 of 70K are 52% identical to tra (69–124) and 40% identical to su(w$^a$) (900–962). Amino acids 348–389 are 50% identical to the same regions. It has been demonstrated that the pre-mRNAs of both these Drosophila proteins undergo alternative splicing, and each may be autoregulated on the basis of splice site selection. It is tempting to speculate that proteins like su(w$^a$), tra, and transformer-2 might compete with the charged domains of 70K to influence the choice of splice sites on pre-mRNA.

Experimental Procedures:

Enzymes, Antisera, Host Strains, and Vectors Enzymes were purchased from Bethesda Research Laboratories, United States Biochemical Corporation (USB), and New England Biolabs.

Autoimmune antisera were obtained from the Duke University Medical Center Fluorescent Antinuclear Antibody Laboratory. Anti-β-galactosidase monoclonal antibody were purchased from Promega.

E. coli strains Y1089, Y1090, and JM83 were obtained from the American Type Culture Collection. Strain NM522 and the pGEM-3Zf(+) single-stranded system were purchased from Promega.

Screening of cDNA Libraries:

λgt11 recombinant phage cDNA libraries were obtained from R. Lazarini (NIH), E. Sadler (Washington University), and Clontech (Palo Alto, Calif.). Libraries were screended using the 70K.1 insert (Query and Keene, 1987) as described (Benton and Davis, 1977).

DNA Sequencing:

Inserts from the λgt11 were subcloned into pSP65 and pGEM-3Zf(+), and sequenced by dideoxynucleotide chain termination (Sanger et al., 1977) using a modified T7 DNA polymerase (Tabor and Richardson, 1987) from the Sequenase system (USB). Oligonucleotides complementary to the SP6 and T7 promoters and specific for 70K sequences were synthesized on an Applied Biosystems 380A DNA synthesizer and purified by HPLC. 70K cDNA sequences were analyzed and compared using an IBM PC and the Beckman Microgenie Sequence Software (Queen and Korn, 1984).

In Vitro Transcription and Translation:

70K sequences were transcribed with T7 (USB) RNA polymerase as described by Melton et al. (1984), and the resulting RNA was translated in vitro (Krieg and Melton, 1984) in rabbit reticulocyte lysates as described by the supplier (Promega). In vitro translation products were subsequently analyzed by electrophoresis on 10% SDS-polyacrylamide gels (Laemnli, 1970) and fluorography. U1 and β-globin RNAs were transcribed with SP6 (Promega) or T7 (USB) RNA polymerase. A genomic clone of human U1 DNA was a gift from Nouria Hernandez (Cold Spring Harbor Laboratory), and was reconstructed to produce U1 RNA authentic in sequence, except for the trimethylated 5' cap and other modified bases (Query et al, 1989b). β-globin (Hβδ6) template was a gift from Robin Reed and Tom Maniatis (Harvard University).

Oligonucleotide-Directed Mutagenesis:

Mutagenesis was performed using pGEM-3Zf(+) vectors prepared according to the supplier (Amersham).

70K Deletion Mutant Constructs:

The sequence surrounding the site of translation initiation was altered by oligonucleotide-directed mutagenesis using the oligonucleotide CTACGGACTTGCGCCACCATGGAGATGACCCAG, which created an optimal translation sequence (Kozak, 1987) while maintaining the full sequence of the 70K protein. Translation products contained two additional amino acids, MetGlu-, at the amino terminus. Mutated cDNA was sequenced in its entirety to verify that no additional mutations had occurred. To construct amino-terminal deletions of the 70K protein, plasmid pGEM3Zf(+)PL40(δ5'UT) was cut at BstXI and XhoI sites 3' to the initiation codon. 70K coding sequence was deleted using Exonuclease III and S1 nuclease (Promega). Modified plasmids were sequenced and categorized as described in Table 2 (δ series).

Carboxy-terminal deletions that ended at amino acid 333, 299, 259, 197, or 52 were produced by digestion of the pGEM-3Zf(+)PL40(δ5'UT) template or amino-terminal-deleted derivatives with various restriction enzymes, as listed in Table 2. Carboxy-terminal deletions ending at amino acid 251, 236, 209, 202, or 189 were produced by Exonuclease III, and S1 nuclease digestion was produced from the 3' end of the template DNA. Constructs ending at residue 216 were produced from templates altered by oligonucleotide-directed mutagenesis to contain a stop at codon 217.

Purification of Recombinant Fusion Protein:

The PL40(δ5'UT) mutation created an NcoI restriction site adjacent to the initiation AUG. An NcoI-EcoRI fragment containing the entire coding region was isolated, blunted, ligated to EcoRI linkers, inserted between λgt11 arms, and packaged in vitro (Promega). Bacteriophage containing the insert in the desired orientation were selected by isopropyl thiogalactopyranoside (IPTG, USB) induction and immunoreactivity with anti-(U1)RNP serum (Young and Davis, 1983). E. coli strain Y1089 was lysogenized with this recombinant phase. The 35–216-LacZ fusion protein was described previously (Query and Keene, 1987). The fusion protein isolation procedure was modified from Adam et al. (1987) and described previously (Query and Keene, 1987).

RNA Binding:

70K-LacZ and control fusion proteins were incubated with RNA in NET-2 (100 mM NaCl, 50 mM Tris [pH 7.4], 0.05% NP-40, 4M urea, 250 U/ml of RNasin (Promega), and 0.3% vanadium ribonucleoside complex (VRC) at 4+ C. for 10 min. In vitro translation products were incubated with RNA in KNET buffer (20 mM KC1, 80 mM NaCl, 2 mM EGTA, 50 mM Tris [pH 7.4], 0.05% NP-40), 1 mM MgCl$_2$, 2.5% polyvinyl alcohol, 100 U/ml of RNasin, 5 μg/ml of poly(A) RNA (Sigma), and 0.2% VRC at 37° C. for 25 min. Total HeLa RNA was precleared with normal human serum and Pansorbin prior to binding.

Immunoprecipitations:

Immunoprecipitations were performed essentially as previously described (Lerner and Steitz, 1979; Kurilla and Keene, 1983). Deproteinized RNA was immunoprecipitated as described by Wilusz and Keene (1986). 70K-LacZ fusion proteins were immunoprecipitated with anti-β-galactosidase monoclonal antibody in NET-2, 4M urea, 0.2% VRC, and Pansorbin (Calbiochem). RNA bound by in vitro translated 70K polypeptides was immunoprecipated using Anti-(U1) RNP serum in KNET buffer, 0.2% VRC, and Pansorbin. The ability of each 70K-derived polypeptide to react with the anti-(U1)RNP serum was verified by immunoprecipitation and andusis of the precipitated protein. The anti-(U1) RNP serum contained no detectable anti-Sm or anti-U1 RNA reactivity. In each case, prior to addition, the Pansorbin was washed twice with NET-1, twice with the buffer used for immunoprecipitation, and incubated with 200 μg/ml of tRNA for 10 min at 4° C. Immunoprecipitated total HeLa RNA was additionally washed with 1M urea, 0.2% VRC. Immunoprecipitated RNA was analyzed by 5% polyacrylamide-8.3M urea gel electrophoresis followed by autoradiography.

Mobility Shift Assays:

70K in vitro translation products, without further purification from the in vitro translation reaction, were incubated with RNA as described above at 37° C. for 20 min to achieve equilibration. In vitro-transcribed U1 RNA, U1δL1, or β-globin RNA were included at a final concentration of 40 μg/ml. The products were added to ¼ volume loading buffer (KNET buffer containing 20% glycerol, 1 mg/ml of xylene cyanol FF, and 1 mg/ml of bromophenol blue) for immediate electrophoresis on a native 5% polyacrylamide gel as described by Hope and Struhl (1985).

Enzymes, Host Strains and Vectors:

Enzymes were obtained from United States Biochemical Corporation and from New England Biolabs. $E.$ $coli$ strain NM522 and the pGEM3zf(+) plasmid vector were purchased from Promega. $E.$ $coli$ strain TG-1 was purchased from Amersham. $E.$ $coli$ strains BL21 and BL21(DE3) pLysS, and the expression vectors pET-3c and pET-8c were gifts from William Studier (Brookhaven National Laboratory). The vector pGEX-2T was obtained from Amrad Corporation Limited.

Cloning Procedures and cDNAs:

cDNA clones of the U1 snRNP-A, U2 snRNP-A$^{prime}$, U1 snRNP-70K, and La proteins were obtained by screening of expression libraries with antisera from patients with autoimmune diseases and are described elsewhere (Lutz-Frevermuth and Keene, (1989); Ouery et al, (1989); Chambers et al, (1988). cDNAs for the U2 snRNP-B" protein were obtained from human fibroblast and endothelial cell λft11 libraries (Clontech, Palo Alto, Calif.) by screening with oligonucleotides corresponding to the previously published cDNA sequence (Habets et al, $Proc.$ $Nat.$ $Aca.$ $Sci.$ ($USA$) 1987) 84: 2421–2425) according to standard techniques (Sambrook et al, 1989). The nucleotide sequence in the open reading frame of the B" cDNAs was identical to the previously published sequence.

In Vitro Transcription and Translation:

DNA constructions were placed next to the promoter for T7 or SP6 RNA polymerase, transcribed in vitro and translated in rabbit reticulocyte lysates as described by the supplier (Promega). Translation products were analyzed by electrophoresis on 15% SDS-polyacrylamide gels followed by fluorography or by trichloroacetic acid precipitation. Clones of human genomic U1, U2, U5 and mouse U6 RNAs were gifts from Nouria Hernandez (Cold Spring Harbor Laboratories), Alan Weiner (Yale University), Jeff Patton (University of South Carolina), and Ram Reddy (Baylor College of Medicine), respectively. Inserts or portions of inserts from each of these clones were subcloned into pGEM-3Zf(+). In vitro transcripts containing full-length RNAs were synthesized from templates linearized with Rsa I (U1), Hpa II (U2), Acc I (U5), or Dde I (U6). A U2 RNA lacking an intact stem-loop IV (U2δSL4, nt 1–152) was transcribed from Taq I truncated template. Both the full-length and truncated U2 transcripts contained 29 additional 51 genomic nucleotides and the full-length transcript contained 5 additional 3' nucleotides. Human B-globin template was truncated at the Bam HI site to produce a 493 nucleotide RNA.

Oligonucleotide-Directed Mutagenesis:

Mutagenesis was performed using pGEM-3zf(+) vectors according to the supplier (Amersham). All mutants were completely sequenced on at least one strand throughout their coding regions. Specific mutations created are indicated in the text. U2 stem-loop IV (U2 SL4) template was synthesized by polymerase chain reaction and represents nucleotides 147–188 of human U2. After cloning into the Eco RI site of pGEM 3Zf(+) the in vitro transcript contained 9 and 5 additional nucleotides at the 5' and 3' ends, respectively. U1 RNA mutations have been described previously Lutz-Frevermuth and Keene, (1989)). U1SL2 transcript contained U1 nucleotides 48–92 plus 9 additional 5' nucleotides.

HeLa Cell RNA Bindings and Immunoprecipitations:

Immunoprecipitations were performed as previously described (query et al, (1989)) except that the RNA binding buffer was NT-2 (50 mM Tris, pH 7.40, 150 mM NaCl, 0.05% NP-40), 1 mM DTT, 10 mM MgCl$_2$, 2% polyvinyl alcohol, 0.1 mg/ml bovine serum albumin, 0.5 mg/ml $E.$ $coli$ tRNA, 0.125 mg/ml poly(A) RNA, and 50 U/ml RNasin (Promega). Precipitations were washed in NT-2. For some of the experiments shown, protein was immunoprecipitated from $E.$ $coli$ extracts on protein A-Sepharose (Sigma) prior to RNA binding. $^{32}$P-labeled HeLa cell RNA was produced as previously described (Kurilla and Keene, 1983). RNA was bound to protein for 5 to 20 minutes at 37° C. and then immunoprecipitated on ice with 1 microliter of antiserum and 4 milligrams of protein A-Sepharose (Sigma) for each 50 microliter binding reaction. For the competition experiments, the indicated in vitro transcribed unlabelled RNAs were added at a concentration of 2.25 μM. HeLa cell S-100 was prepared by standard techniques; heat inactivation was at 90° C. for 5 minutes.

Overexpression of Protein in $E.$ $coli$:

Proteins were produced in $E.$ $coli$ using an inducible T7 RNA polymerase expression system or the Glutagene system (Amrad Corp). An Nco I site was introduced of the U2 snRNP-B" and U2 snRNP-A$^{prime}$ proteins. Nco I-Eco RI inserts were isolated from these constructs as well as from the U1 snRNP-A protein and subcloned in frame into the BamHl site of either pET-3c or pGEX-2T. The constructs were then transfected into BL21(DE3)pLysS (for pET-3c) or BL21 (for pGEX-2T). Following induction, bacteria were lysed by freeze-thaw and sonication and the insoluble material removed by centrifugation at 10,000×g for 15 minutes. The crude extracts were used directly for immunoprecipitation and RNA bindings. Protein induction was evaluated after SDS-polyacrylamide gel electrophoresis by Western blot analysis and by Coomassie Blue staining.

Mobility Shift Assays:

$^{35}$S-labeled translation products were incubated with in vitro transcribed RNA in the binding buffer described above, with the addition of 0.1M EGTA, followed by electrophoresis in a nondenaturing 5% polyacrylamide, 90 mM trisborate (pH 8.3) gel. Quantitative titrations using the mobility shift assay were performed as previously described (Lutz-Frevermuth, 1990). The highest RNA concentration of 7.5 μM was used with serial two-fold dilutions. The Kd was estimated as the RNA concentration at which 50% of the protein was present in the slower migrating complex.

The B" protein can bind directly to both U1 and U2 RNAs in vitro B" cDNAs were obtained by screening libraries with oligonucleotides from the known cDNA sequence (Habets et al, 1987), and the recombinant B" protein was produced in reticulocyte lysates by in vitro transcription and translation or in $E.$ $coli$ using the pET T7 expression system. The pET construct produced proteins fused to the first 12 amino acids of the phage T7 gene 10 protein (g10). Production of a rabbit antiserum against a synthetic g10 peptide allowed us to utilize the fused g10 peptide as an epitope tag for immunoprecipitations. This method of RNA binding avoided the use of human autoimmune sera against the B" protein which often cross-react with A protein and may have other snRNP autoantibodies. When total HeLa cell $^{32}$p-labeled RNA was incubated with the full-length recombinant g10-B" fusion protein (g10-FLB") synthesized in E. coli and immunoprecipitated with g10-peptide antiserum, weak binding to both U1 and U2 RNAs was detected (FIG. 8A, lane 4; see also FIG. 8A, lanes 8 and 10, and FIG. 9, lane 4). In contrast the g10 antiserum alone or extracts from E. coli containing only the pET vector (FIG. 8A, lanes 2 and 3) showed no detectable binding. The binding of B" to U1 as well as U2 RNAs was unexpected because B" has been reported to be part of the U2 snRNP complex and is not known to associate with U1 snRNPs. On the other hand, given the sequence similarities between the RRMs of the U1 snRNP-A and the U2 snRNP-B" proteins, it was anticipated that some degree of cross-recognition of U1 and U2 RNAs might be possible (depicted in FIG. 10B).

U2 snRNP-A$^{prime}$ protein provides an accessory binding function for B"

Figure 8A:
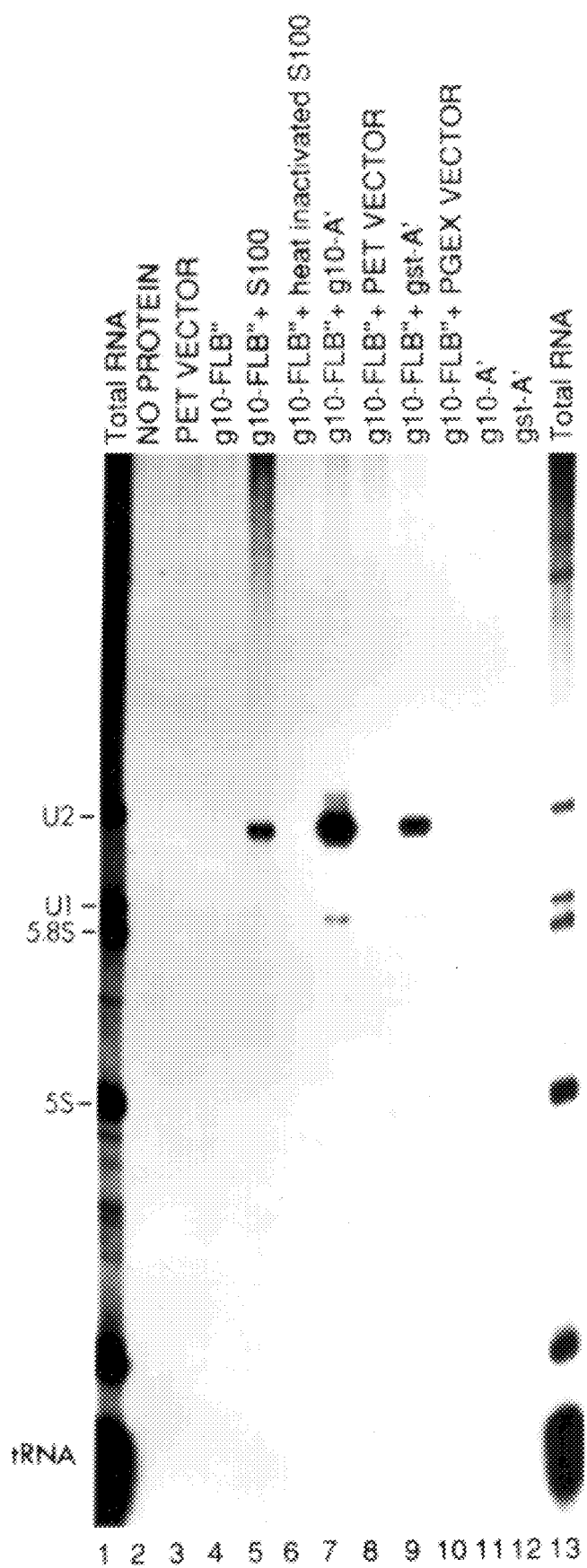
FIGS. 8a and 8b show the binding of recombinant U2 snRNP-B" protein to HeLa cell U1 and U2 RNAs and the enhancement of U2 binding by the U2 snRNP-A$^{prime}$ protein. (A) Full length U2 snRNP-B" and U2 snRNP-A$^{prime}$ proteins produced in *E. coli* as T7 gene 10-peptide (g10) fusion proteins or as glutathione-S-transferase (gast) fusion proteins were incubated with total $^3$P-labeled HeLa cell RNA. After binding as described in the text, the proteins were immunoprecipitated with the g10 antiserum, and the co-precipitated RNAs were examined by 5% polyacrylamide-8.3M urea gel electrophoresis. Lanes 1 and 13, total HeLa cell RNA; lane 2, no extract added (antiserum and protein-A sepharose only); lanes 3–12, bindings using *E. coli* extracts expressing the following: lane 3, pET vector alone; lane 4, full-length g10-B" alone; lanes 5–10, full-length g10-B" plus HeLa cell S100 extract (lane 5), heat inactivated S-100 extract (lane 9), or pGEX vector (lane 10); lane 11, g10-A$^{prime}$ alone; lane 12, gst-A$^{prime}$ alone. (B) In vitro translated g10-A$^{prime}$ was incubated with $^{32}$P-labeled HeLa cell RNA and the in vitro translated B" polypeptides indicated above each lane, followed by immunoprecipitation as in panel A. Lane 1, total HeLa cell RNA; lanes 2–6, g10-A$^{prime}$ plus: an unprogrammed translation (lane 2), B" amino acids 1–109 (lane 3), full-length B" (lane 4), g10-B" amino acids 1–109 (lane 5), or g10-full length B" (lane 6).
Figure 8B:
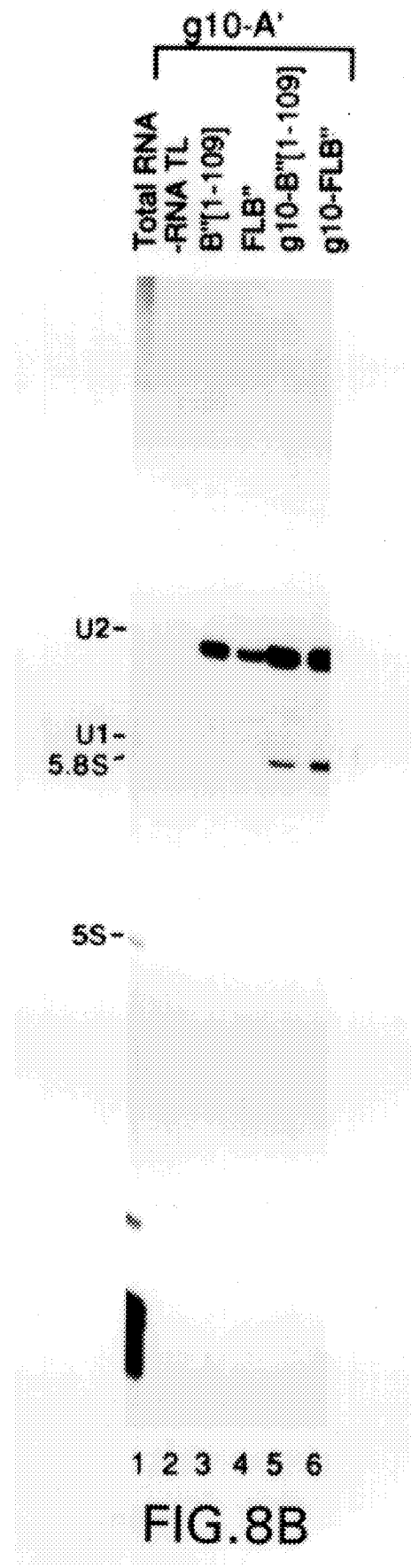
Figure 9:
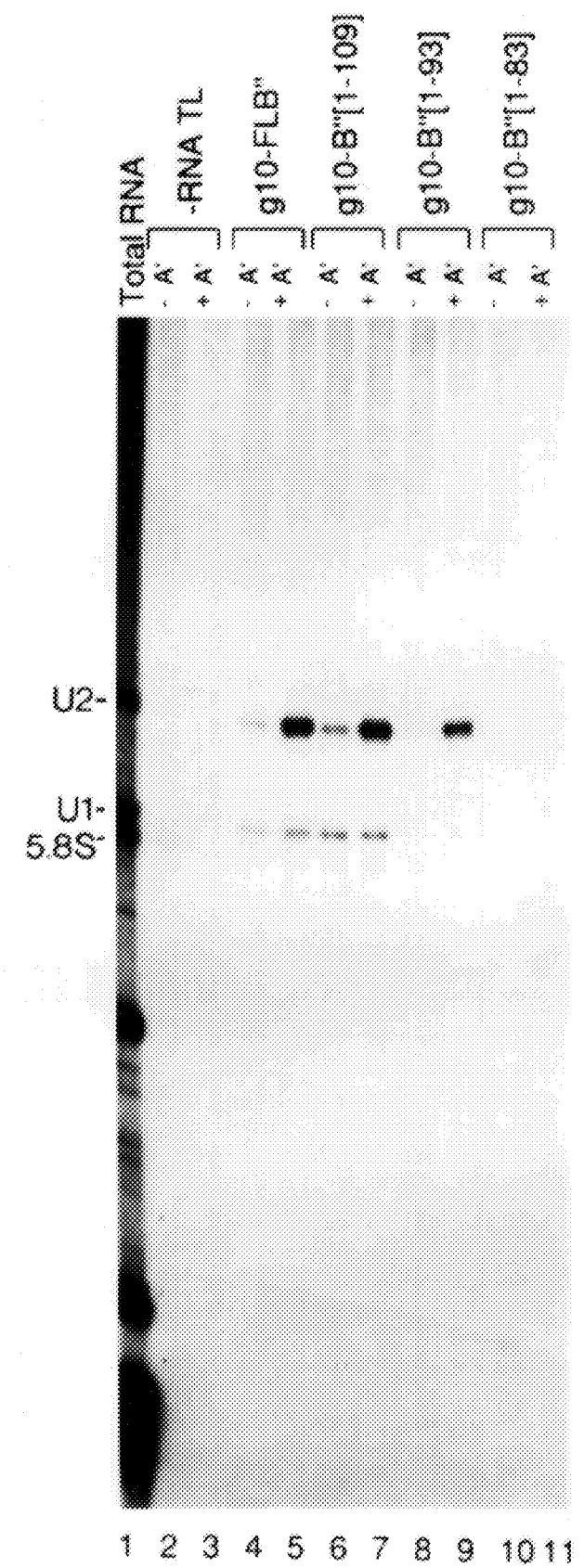
FIG. 9 shows the definition of the RNA-binding domain of U2 snRNP-B" protein. HeLa cell RNA bindings were performed as in FIG. 1, in either the absence (−) or presence (+) of *E. coli* extract containing gst-A$^{prime}$. The in vitro translated g10-B" polypeptides were added in equimolar amounts. Lane 1, HeLa cell total RNA; lanes 2 and 3, unprogrammed translation; lanes 4 and 5, g10-full length B"; lanes 6 and 7, g10-B" amino acids 1–109; lanes 8 and 9, g10-B" amino acids 1–93; lanes 10 and 11, g10-B" amino acids 1–83.

It is possible that binding of B" protein to either U1 or U2 RNAs could be affected by the presence of other cellular proteins. Addition of a HeLa cell S-100 extract to the B"-binding reaction resulted in a dramatic enhancement of binding to U2 RNA (FIG. 8A, lane 5). This effect was dosage-dependent and heat sensitive (lane 6), suggesting the involvement of a protein factor. The other U2 snRNP-specific protein A$^{prime}$ is an obvious candidate for such a factor. The addition of recombinant g10-A$^{prime}$ produced in E. coli (lane 7) caused an increase in the apparent affinity of B" for U2 RNA similar to that produced by addition of S-100 cell extracts. We estimate that A$^{prime}$ caused an approximately 100-fold stimulation of B" binding to U2 RNA. Control experiments utilizing recombinant g10-La or G10-A fusion proteins resulted in no apparent enhancement of binding of B" to U2 RNA. Similar binding results were obtained when any or all of the proteins were translated in vitro in reticulocyte lysates (FIG. 8B, FIG. 9).

To rule out any role for the g10 tag in the apparent enhancement of binding, an alternate A$^{prime}$ fusion protein that lacked this epitope was tested. FIG. 8A, lane 9, shows that the enhancement effect of A$^{prime}$ on binding of B" to U2 RNA occurred also with an A$^{prime}$ protein expressed as a glutathione S-transferase (gst) fusion protein from a PGEX vector in E. coli. A control for the PGEX vector (lane 10) shows that addition of extracts from bacteria containing the vector alone produced the same low level binding of U1 and U2 RNAs to B" as seen in the absence of A$^{prime}$ (lane 4). We also showed that in vitro translated non-fusion protein A$^{prime}$ caused a similar increase in the binding of B" to U2 RNA.

To exclude a direct RNA binding activity of the A$^{prime}$ fusion proteins, the E. coli expressed A$^{prime}$ fusion proteins were assayed directly for their ability to bind $^{32}$P-labeled HeLa cell total RNA. Neither g10-A$^{prime}$ fusion protein nor gst-A$^{prime}$ fusion protein (FIG. 8A, lanes 11 and 12) detectably bound any RNA. Thus, we conclude that A$^{prime}$ acts as an accessory factor to enhance or stabilize the binding of B" protein to U2 RNA, but that A$^{prime}$ itself does not bind detectably to U1 or U2 RNAs.

The A$^{prime}$ accessory factor associates only with U2 snRNPs

In the experiments described above, a small amount of U1 RNA continued to be co-precipitated with B" even in the presence of A$^{prime}$ (FIG. 8A, lanes 7 and 9). A g10-A$^{prime}$ fusion protein was used to determine whether A$^{prime}$ was associated with U2 and U1 RNA in the presence of B". In vitro translated g30-A$^{prime}$ and B" or g10-B" polypeptides were used in combination to bind to HeLa cell total RNA (FIG. 8B). When the g10 epitope tag was present on A$^{prime}$ only and not on B" (lanes 3 and 4) only U2 RNA was co-precipitated by g10 antiserum. On the other hand, when the epitope tag was on both A$^{prime}$ and B", binding to both U1 and U2 RNAs was evident (lanes 5 and 6). Both full-length B" (amino acids 1 to 225, lane 6) and a fragment lacking the carboxy-terminal RRM (amino acids 1 to 109, lane 5) were sufficient to bind U1 and U2 RNAs, and both could interact with A$^{prime}$ to allow specific co-precipitation of U2 RNA (lanes 3 and 4). B" is similar therefore to A, in that the carboxy-terminal RRM is not needed as part of the U RNA binding domain. These results show that A$^{prime}$ can associate specifically with U2 snRNA, but only in the presence of B", while B" itself is capable under these conditions of binding directly to U1 or U2. snRNAs through its amino-terminal RNA binding domain.

Both U2 RNA binding and accessory response to A$^{prime}$ map to the amino-terminal RRM of B"

To investigate the minimal size of the RNA binding domain of the B" protein and to determine whether regions flanking the amino-terminal RRM are critical to the A$^{prime}$ enhancement effect, further deletions were prepared from the carboxy-terminus of B" and translated in vitro as g10-fusion proteins. As shown in FIG. 9, amino acids 1 to 93 of B" were capable of binding both U1 and U2 RNA (lane 8) although at slightly lower efficiency than amino acids 1–109 or full-length constructs (compare lanes 4, 6 and 8). In addition, U2 RNA binding by B" amino acids 1–93 was enhanced by the A$^{prime}$ protein (lane 9). In contrast, amino acids 1 to 83 were not sufficient for either property (lanes 10 and 11). Separate immunoprecipitation experiments showed that the g10 antiserum precipitated all of the deletion constructs with comparable efficiency, excluding inaccessibility of the epitope tag as a cause for the loss of apparent RNA binding (data not shown). Thus, the minimal RNA binding domain of the B" protein is very similar to that reported previously for the U1 snRNP-A protein and the site(s) required for A$^{prime}$ enhancement is within the 93 amino acid RNA binding domain of B". We also have repeated these experiments using E. coli-produced G10-B" polypeptides to rule out the possibility of interactions with other snRNP proteins which might be present in the reticulocyte lysates. The results were identical using E. coli produced polypeptides, confirming that the 93 amino acid domain of B" binds U1 and U2 RNAs directly and not through another snRNP protein.

B" protein recognizes stem-loop IV of U2 RNA

Figure 10A:
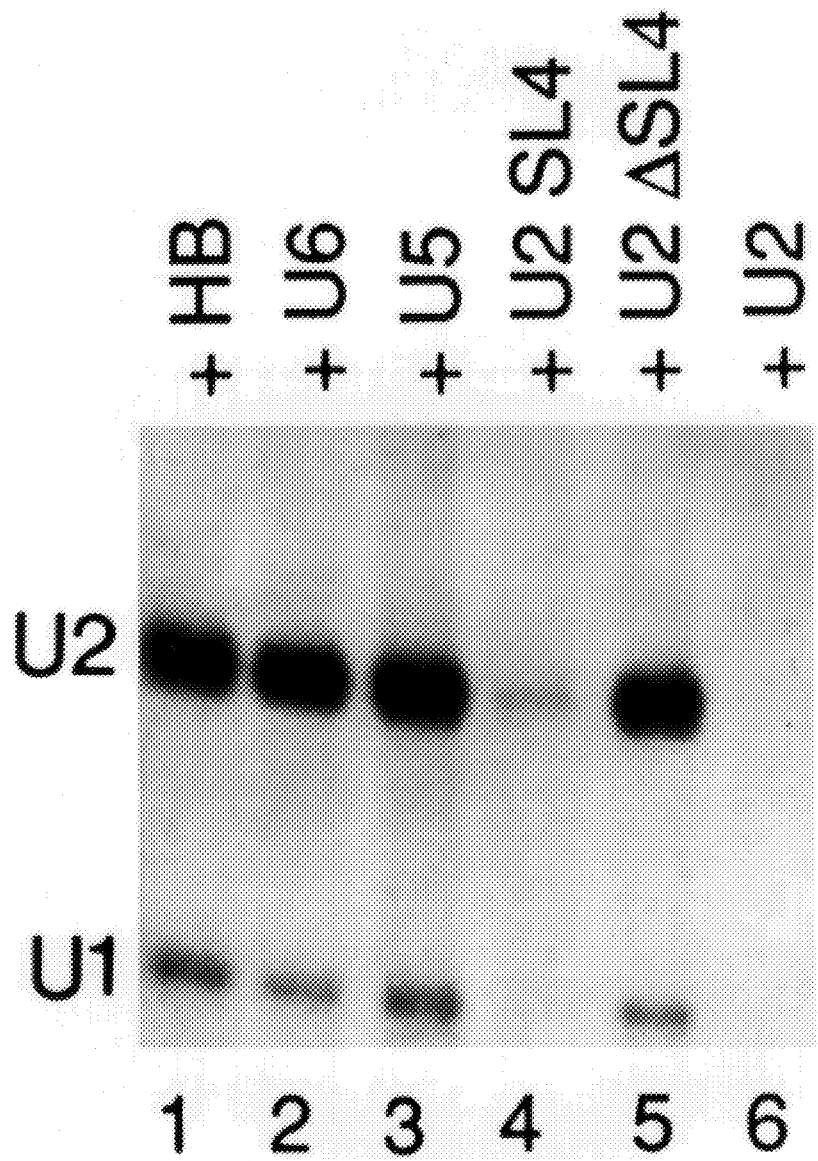
FIGS. 10A and 10B show that the U2 snRNP-B" protein interacts primarily with stem-loop IV of U2 RNA. (A) In vitro transcribed RNAs were tested for their ability to compete against in vivo labeled U1 and U2 RNAs. *E. coli* extracts containing overexpressed g10-B" amino acids 1–109 were bound to $^{32}$P-labeled HeLa cell total RNA and analyzed as in FIG. 1, except that each binding reaction contained in addition 2.25 μM unlabeled in vitro transcribed competitor RNA as follows: lane 1, β-globin RNA; lane 2, U6 RNA; lane 3, U5 RNA; lane 4, stem-loop IV of U2 RNA(U2 SL4); lane 5, U2 RNA lacking stem-loop IV (U2ΔSL4); lane 6, full-length U2 RNA. (B) Schematic diagram showing the similarity between the RRMs of A and B" and between stem-loop II of human U1 RNA and stemloop IV of human U2 RNA. Black shaded boxes in the proteins represent the RRMs and the grey boxes show the location of the RNP octamer sequence. Nucleotides that are identical in the two loops of U1 and U2 RNA are shown in boldface. In U1 RNA, the loop sequence AUUGCACU is phylogenetically conserved in a number of species ranging from yeast to mammals. In U2 RNA, the sequences UUG-CANU is conserved (Guthrie et al, *Ann. Rev.* (1988) 22:387–419).

RNA binding domains for the A and the 70K proteins have been shown to directly contact independent stem-loop structures. The structural similarity between the A and B" proteins suggests that the sites which they recognize on their respective RNAs might also be similar. Using the HeLa cell total RNA binding assay described above, regions of U2 RNA involved in the efficient binding to B" in the presence of A$^{prime}$ were examined in a series of competition-binding assays (FIG. 10A). Heterologous unlabeled RNAs added in excess were not able to compete with U1 or U2 RNAs (B-globin, U6, and U5 RNAS, lanes 1–3) and a mutant in U2 RNA lacking stem-loop IV also did not compete (U2ASL4, lane 5). In contrast, full-length U2 RNA or stem-loop IV of U2 RNA competed effectively for binding with the in vivo-labeled U2 RNA (lanes 4 and 6). The efficiency of competition by stem-loop IV was less than complete, which may indicate that other regions of U2 RNA also participate in binding. From these and other binding data we conclude that stem-loop IV of U2 RNA forms the major binding site of B" protein in the presence of A$^{prime}$.

Figure 10B:
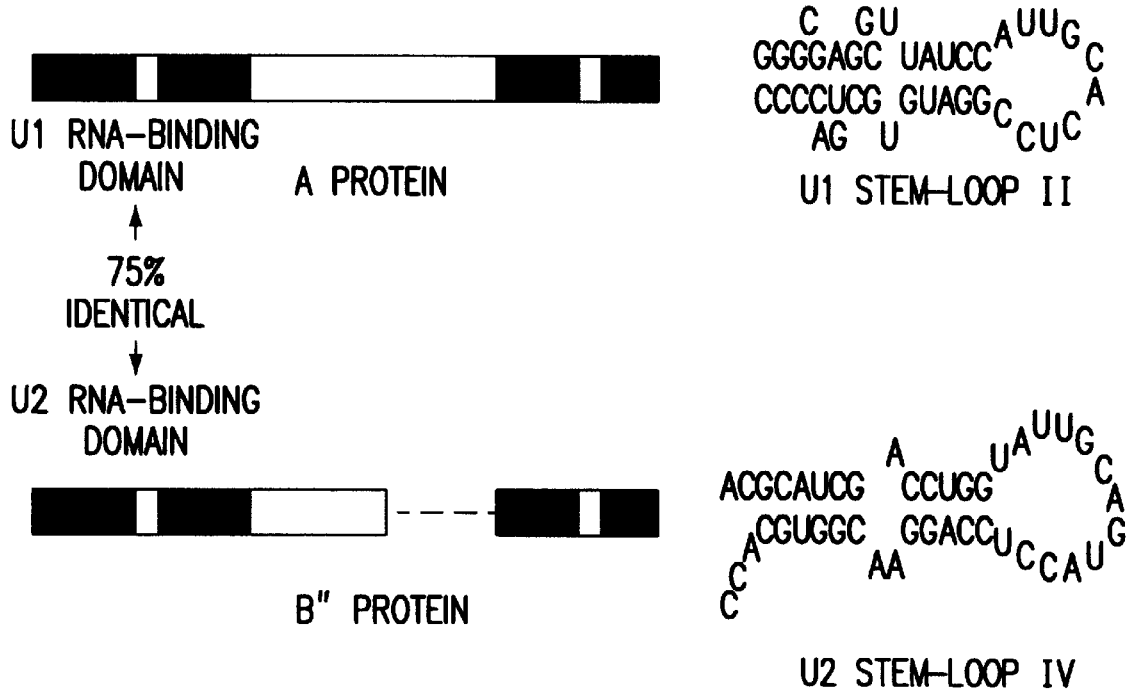
Figure 12A:
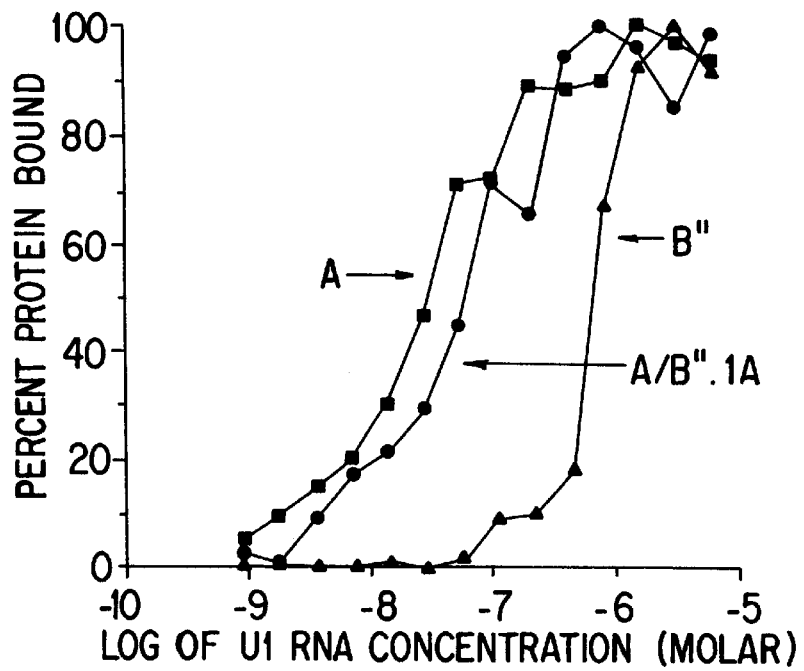
FIGS. 12A and 12B provide a quantitative demonstration that the pentamer mutant A/B".1A retains the affinity of the U1 snRNP-A protein for U1 RNA but acquires an affinity for U2 RNA similar to that of the U2 snRNP-B" protein. Relative binding affinities were measured using the mobility shift method as described (Lutz-Frevermuth et al., (1990)). In brief, a constant amount of in vitro translated protein was incubated with serial two-fold dilutions of an in vitro transcribed RNA representing stem-loop II of U1 (A) or fulllength U2 (B). The graphs show the percent protein present in the specific RNP complex at each concentration of RNA used. The B" polypeptide used represented amino acids 1–109; the A and A/B".1A polypeptides represented amino acids 1–142.

The sequence present in the loop of U2 stem-loop IV is similar to that in the loop of U1 stem-loop II, which is the binding site for the A protein (FIG. 10B, identical nucleotides in boldface). This suggests that these two very similar proteins may recognize the similar loop sequences in each RNA, along with some additional sequence or structural feature unique to its correct partner. In the case of B", this specific recognition requires the presence of $A^{prime}$ as an accessory factor. This model predicts that B" recognizes U1 RNA through cross-reactivity with stem-loop II of U1 RNA. We show below (FIG. 12) that this stem-loop bound B" with approximately the same affinity as U2 RNA. Further evidence of the similarity between stem-loop II of U1 RNA and stem-loop IV of U2 RNA is the observation that stem-loop IV of U2 RNA competed for binding of U1 RNA to B" (FIG. 10A, lane 4) while other RNAs did not (FIG. 10A, lanes 1–3 and 5)

A different sequence similarity was previously noted between U1 stem-loop II and U2 stem-loop III. However, these similarities are between bases that are in a loop in U1 but in a stem in U2. Furthermore, the U2 stem-loop IV sequence is more highly conserved among species than the stem-loop III sequence.

Figure 11B:
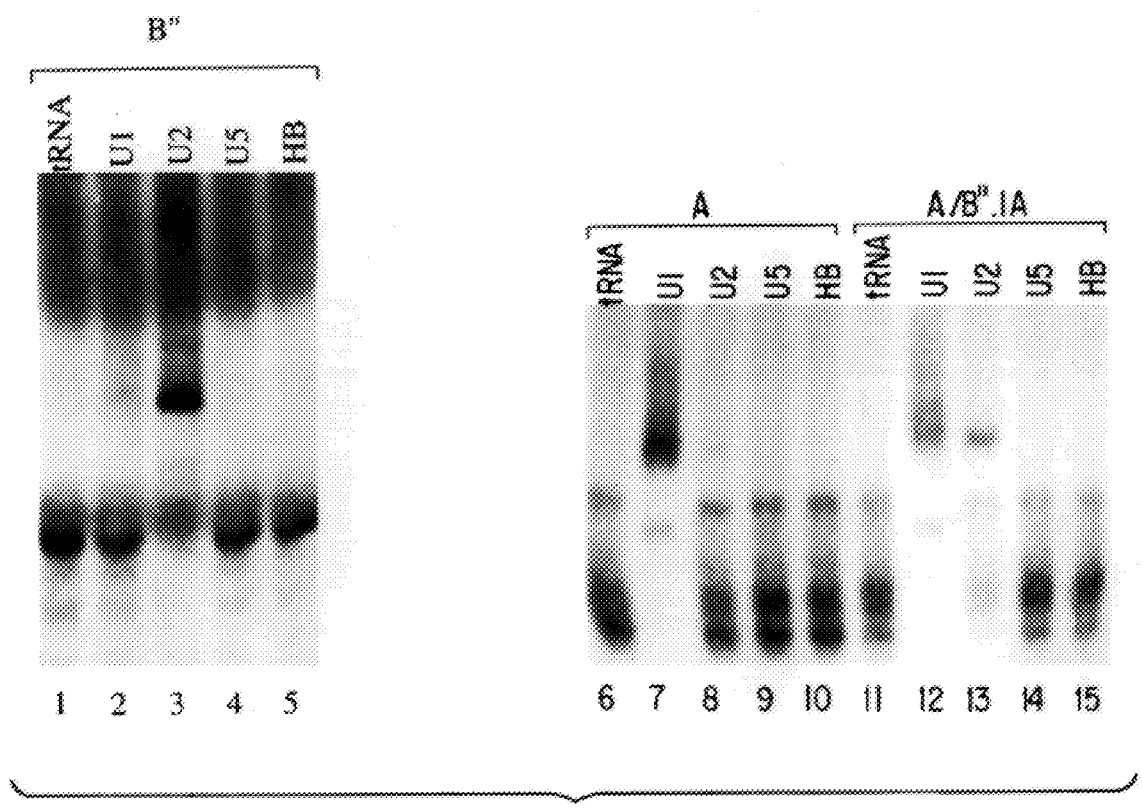

A 5 amino acid sequence from the B" protein confers recognition of U2 RNA when placed in the A protein The close primary sequence relationship between the A and the B" proteins (FIG. 10B) led us to test whether the element(s) controlling the specificity of RNA recognition might be interchangeable. As shown in FIG. 11A, site-directed mutants were constructed that progressively converted elements of the A aminoterminal RRM into the corresponding elements of the B" aminoterminal RRM. The RNA recognition properties of these mutants were analyzed using a mobility shift assay in which $^{35}$S-labeled in vitro translated proteins were bound to RNA in the absence of $A^{prime}$ and subjected to native gel electrophoresis. As shown in FIG. 11B, B" forms a complex of slower mobility in the presence of either U1 or U2 RNAs (lanes 2 and 3) when compared to transfer RNA, β-globin RNA or U5 RNA (lanes 1, 4 and 5). This finding confirmed that B" binds only to U1 and U2 RNAs and not to other RNAs in the absence of $A^{prime}$. In contrast, A forms a complex with only U1 RNA (lane 7) under the same conditions.

Figure 11C:
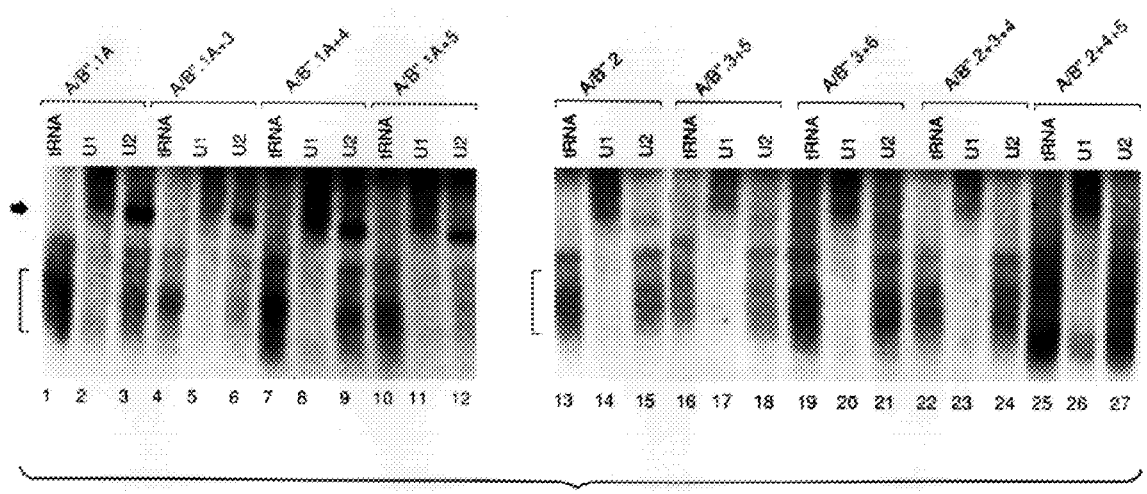

This mobility shift assay was used to screen the A/B" conversion mutants for the ability to bind to U2 and U1 RNAS. The results of these assays are summarized in the columns on the left side of FIG. 11A and representative examples are shown in FIG. 4C. Lanes 1 to 12 show the four conversion mutants which gained the ability to bind to U2 RNA in comparison with the parental wild type A protein. For each of these mutants a new complex of slower mobility was seen with either U1 RNA (lanes 2, 5, 8 and 11) or U2 RNA (lanes 3, 6, 9 and 12) when compared to the tRNA-only lanes (lanes 1, 4, 7 and 10). Representative examples of mutants which showed no U2 RNA binding are shown in FIG. 11C, lanes 13–27. In contrast, these mutants failed to form a new complex in the presence of U2 RNA (lanes 15, 18, 21, 24 and 27), although all remained capable of binding to U1 RNA (lanes 14, 17, 20, 23 and 26).

Figure 13A:
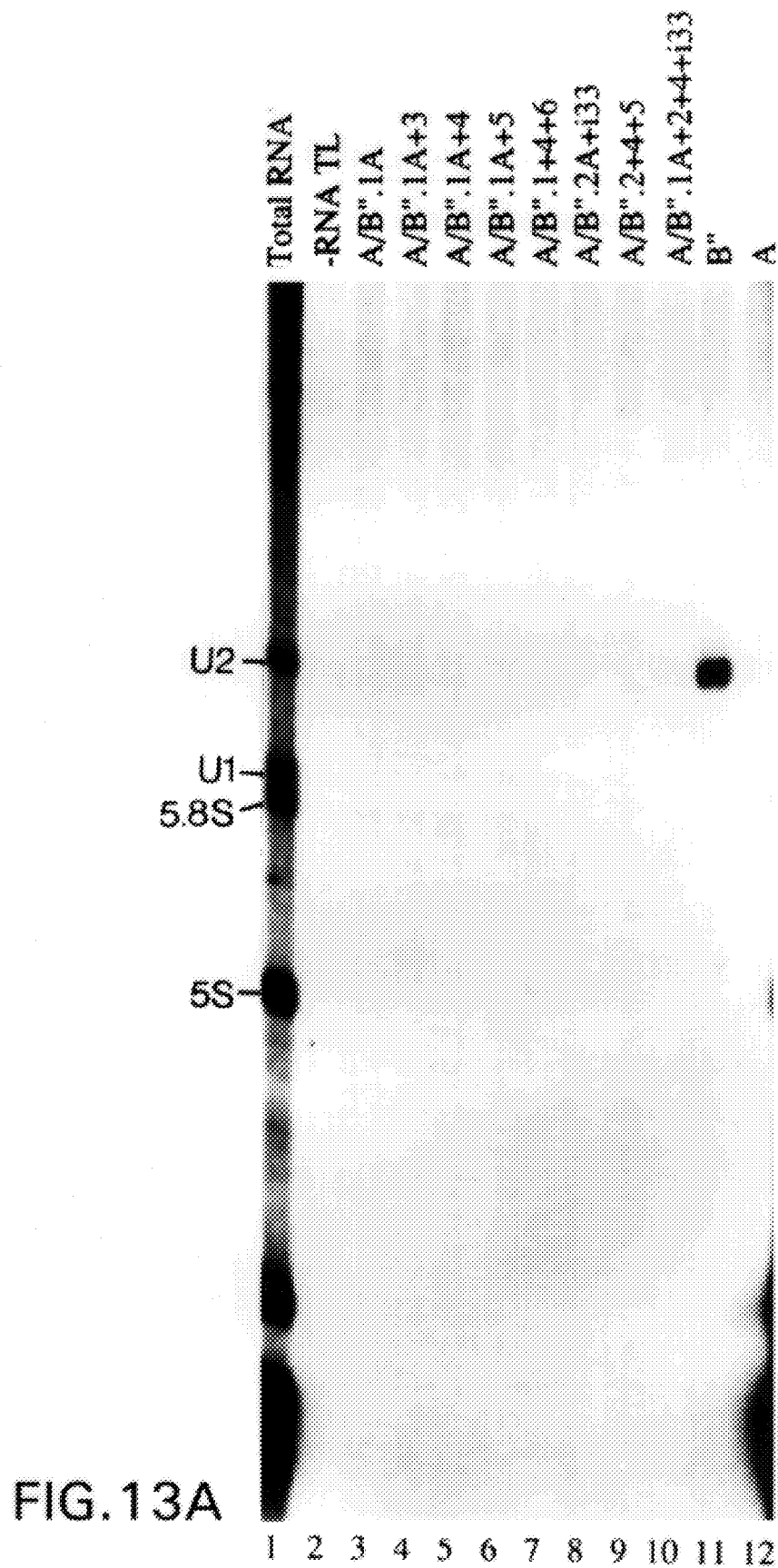
FIGS. 13A and 13B show regions of U2 snRNP-B" outside the pentamer sequence responsible for U2 RNA recognition are necessary for interaction with $A^{prime}$ and enhancement of U2 RNA binding. (A) E. coli extract containing g10-$A^{prime}$ was bound to $^{32}$P-labeled HeLa cell total RNA in the presence of the following in vitro translated polypeptides and analyzed as in FIG. 1B: lane 1, HeLa cel total RNA; lane 2; unprogrammed translation; lane 3, A/B"1A; lane 4, A/B".1A+3, lane 5, A/B".1A+4; lane 6, A/B".1A+5; lane 7, A/B".1+4A+6; lane 8, A/B"1.2A+33; lane 9, A/B".2+4+5; lane 10, A/B".1A+2+4+i33; lane 11, B" amino acids 1–109; lane 11, wild-type A. Except as noted, all the translated polypeptides represented full-length proteins. (B) Bindings of HeLa cell total RNA to wild-type A and to the pentamer mutant A/B".1A. E. coli extracts containing overexpressed g10-A or G10-A/B".1A were used to bind $^{32}$P-labeled Hela cell total RNA, and the co-precipitated RNAs were analyzed as in FIG. 1. Lanes 1 and 2, E. coli-expressed g10-A plus HeLa cell S-100 extract (lane 1) or alone (lane 2); lane 3, HeLa cell total RNA; lane 4, E. coli-expressed g10-A/B".1A; lanes 5–6, g10-A/B".1A plus E. coli-expressed g10-$A^{prime}$ (lane 5) or gst-$A^{prime}$ (lane 6); lane 7, HeLa cell total RNA. The small amount of 5S RNA seen in all the lanes is due to non-specific binding by the protein A-Sepharose and represents a minor experimental artifact.
Figure 13B:
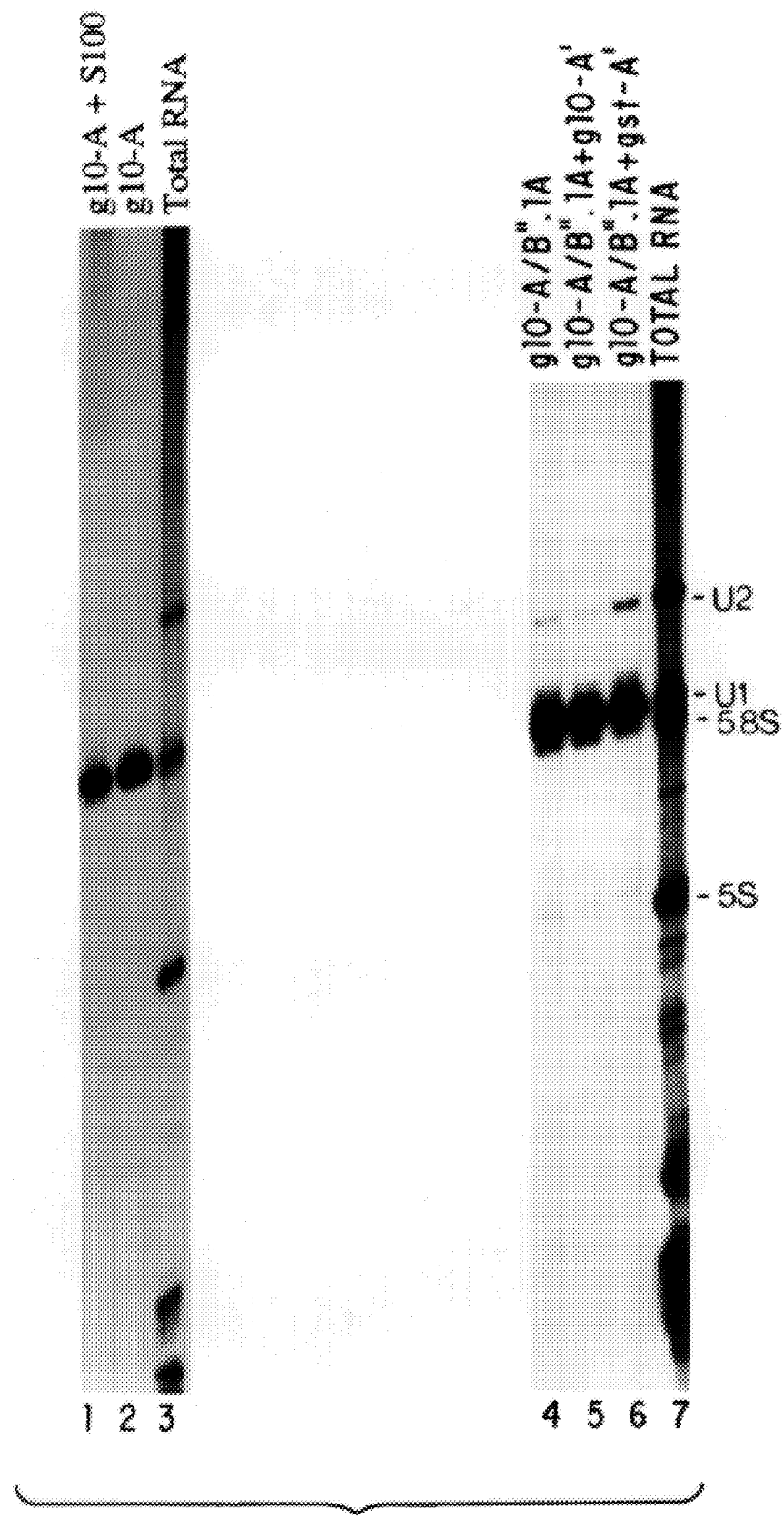

The four mutants which bound to U2 RNA in the mobility shift assay had in common the conversion of amino acids 44 to 48 of A (LVSRS; see FIG. 11A, block 1) to the corresponding sequence of B" (amino acids 41 to 45; VALKT). In the case of one mutant (A/B".IA) this was the only mutation introduced into A, thus directly demonstrating that this simple 5 amino acid change alters the RNA recognition specificity of the A protein. This pentamer sequence (which is part of the six amino acids indicated as block I at the bottom of FIG. 11A, and is boxed in the sequence of A/B".1A) is part of a highly variable region in the RRM which we have called variable region-I (VR-I; see Discussion). FIG. 11B, lanes 11–15, show a mobility shift analysis of the pentamer mutant performed in parallel to wild-type B" and A (lanes 1–10). Binding of the mutant to U1 RNA (lane 12) or to U2 RNA (lane 13) was not due to nonspecific binding, as unrelated β-globin or U5 RNAs failed to form complexes (lanes 14 and 15). In addition, when the pentamer mutant was expressed as a g10 fusion protein in E. coli and used to bind HeLa cell total RNA, U1 and U2 RNAs were the only species specifically precipitated (FIG. 13B, lane 4). We conclude that conversion of the 5 amino acid sequence in A to that of B" results in a gain of specific recognition of U2 RNA rather than a general relaxation of the specificity of RNA recognition.

Relative affinities of A, B", and the pentamer mutant for U1 and U2 RNAs

Figure 12B:
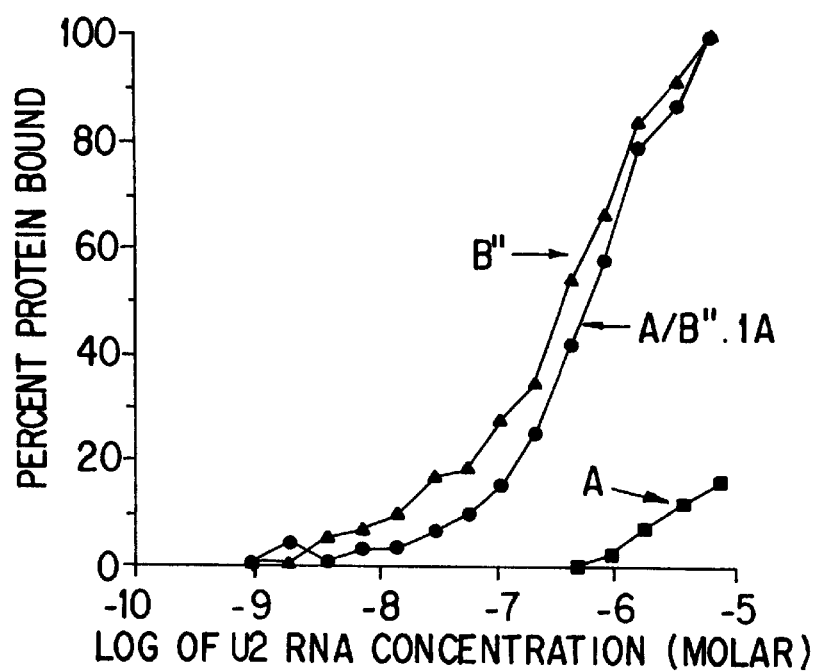

To quantitate the relative apparent affinities of wild type A, wild type B" and the pentamer mutant A/B".1A for U1 and U2 RNAs, serial dilutions of U1 RNA stem-loop II (FIG. 12A) or of U2 stemloop IV (FIG. 12B) were incubated with a constant amount of $^{35}$S-labeled in vitro translated protein. The amount of the labeled protein bound was then assayed by mobility shift analysis, and the results quantitated by densitometry to obtain an estimate of the relative affinities for each RNA. The pentamer mutant (A/B".1A) retained the high affinity for U1 RNA ($K_d \approx 70$ nM) characteristic of its parent A protein ($K_d \approx 30$ nM) when compared to the much lower affinity of B" for U1 ($K_d \approx 800$ nm) (FIG. 12A) Conversely, the pentamer mutant showed an affinity for U2 RNA ($K_d \approx 900$ nM) similar to wild-type B" ($K_d 400$ nM), while A showed-only very low affinity binding of U2 RNA ($K_d > 10,000$ nM) (FIG. 12B). These estimates are in accord with an earlier estimate of 80 nM for the $K_d$ of A and U1 stem-loop II. In summary, the pentamer conversion mutant retained a U1 RNA binding affinity similar to its parental protein while acquiring the ability to bind U2 RNA with nearly the same relative affinity as wild-type B". Therefore, other sequence differences between A and B" are either functionally equivalent in the two proteins or are at positions unimportant for U2 RNA binding by B".

The site of interaction of $A^{prime}$ within the RRM of B" is distinct from the pentamer sequence involved in U2 RNA recognition To determine whether the pentamer sequence in the conversion mutants is also sufficient for the enhancement of U2 RNA binding by $A^{prime}$, the A/B" conversion mutants were assayed for their abilities to interact with $A^{prime}$. In vitro translated A, B", or A/B" conversion mutant polypeptides were added to E. coli produced g10-$A^{prime}$ fusion protein, incubated with labeled HeLa cell total RNA, and immunoprecipitated with the g10 antiserum (FIG. 13A). It is evident that the wild-type B" protein enabled the g10 peptidetagged $A^{prime}$ protein to complex with and co-precipitate U2 RNA (lane 11), while none of the conversion mutants were able to do so (lanes 3–10). As expected, the A protein could not enter into an RNP complex with the $A^{prime}$ protein (lane 12). These data demonstrate that the site on B" that allows it to interact properly with A prime is distinct from the pentamer sequence that controls U2 RNA recognition.

As a confirmatory assay for the ability to interact with $A^{prime}$, the pentamer mutant was expressed in E. coli fused to the g10 epitope tag and tested for binding of $^{32}$P-labeled HeLa cell total RNA (FIG. 13B). In the absence of $A^{prime}$ protein, the pentamer mutant bound to U2 at a relatively low level (lane 4), and the addition of either g10-A$^{prime}$ or gst-A$^{prime}$ had no effect on the efficiency of U2 RNA binding (lanes 5 and 6). As expected from the quantitative estimates of binding affinities (FIG. 12A), U1 RNA continued to be bound at high affinity by the mutant (lane 4); this binding was not affected by the addition of A$^{prime}$ (lanes 5 and 6). For comparison, the wild-type A protein bound only U1 RNA at relatively high efficiency as described previously and was not affected by the addition of an S-100 extract (lanes 1 and 2). These data demonstrate that the pentamer sequence itself is insufficient to confer any detectable A$^{prime}$-dependent enhancement of U2 RNA binding, and that sequences outside this segment are required.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A compound of formula (IX):

(component Y)—(cognate RNA)

wherein:
(i) said component Y is covalently bound to said cognate RNA, said component Y being one member selected from the group consisting of DNA probes, RNA probes, antigens, and antibodies; and
(ii) said cognate RNA is a polynucleotide comprising at least the sequence:

5' GGGAGAUACCAUGAUCACGAAGGUGGUUUUCCC 3' and up to the sequence of U1 RNA.

2. A complex of formula (V):

(component x)—(protein)—(cognate RNA)—(component Y)

wherein:
(I) said protein is a protein which consists of an RNA recognition motif which specifically binds to the U1 RNA sequence set forth as stem-loop (I) in FIG. 1, wherein said protein exhibits at least 35% similarity with Sequences I, II or m and exhibits at least 35% similarity with the amino acid sequence of U1-70K from amino acid positions 104–183;
and wherein said protein further consists of from 0–20 additional amino acids attached to the N'-terminal end of said protein and from 0–20 additional amino acids attached to the C-terminal end of said protein, wherein said 0–20 amino acids attached to the N-terminal and said 0–20 additional amino acids attached to the C-terminal do not interfere with said U1 RNA specific binding property of said RNA recognition motif;
(ii) said component X is covalently bound to said protein, said component X being one member selected from the group consisting of DNA probes, RNA probes, antigens, antibodies, ribonucleases, methylases, RNA comprising enzymes and proteases;
(iii) said cognate RNA is complexed to said protein and is a polynucleotide comprising at least the sequence:

5'GGAGAUACCAUGAUCACGAAGGUGGUUUUCCC3' and up to the sequence of U1 RNA; and
(iv) said component Y is covalently linked to said cognate RNA and is a member selected from the group consisting of DNA probes, antigens, and antibodies.

3. The complex of claim 2, wherein said protein (i) is a protein having amino acid sequence (I) or a protein having at least 35% sequence similarity with said sequence (I).

4. The complex of claim 2, wherein said protein (i) is a protein having amino acid sequence (II) or a protein having at least 35% sequence similarity with said sequence (II).

5. The complex of claim 2, wherein said protein (i) is a protein having the amino acid sequence of residues 92 to 211 of Sequence III and which may include additional residues up to 1 to 240 of sequence (III), or of a protein having at least 35% sequence similarity with said sequence (III).

6. The complex of claim 2, wherein said protein (i) is a protein consisting of an amino acid sequence which is one member selected from the group consisting of the sequences in FIG. 6 to which up to 10 amino acids are attached at each end of said sequences, wherein said 10 amino acids are the 10 amino acids occurring in the corresponding native protein sequences shown in FIG. 6.

7. The complex of claim 2, wherein said protein (i) is a protein consisting of an amino acid sequence which is one member selected from the group consisting of the sequences in FIG. 6 to which up to 20 amino acids are attached at each end of said sequences, wherein said 20 amino acids are the 20 amino acids occurring in the corresponding native protein sequences shown in FIG. 6.

8. The complex of claim 2, wherein said RNA Y is a RNA which binds with the RNA of the AIDS/HIV virus.

9. A compound of formula (VII):

(component Y)—(protein)

Wherein:
(I) said component Y is covalently bound to said protein, said component Y being one member selected from the group consisting of DNA probes, RNA probe, antigens, and antibodies; and
(ii) said protein is a protein which consists of an RNA recognition motif which specifically binds to the U1 RNA sequence set forth as stem-loop (I) in FIG. 1, wherein said protein exhibits at least 35% similarity with Sequences I, II or III and exhibits at least 35% similarity with the amino acid sequence of U1-70K from amino acid positions 104–183;
and wherein said protein further consists of from 0–20 additional amino acids attached to the N'-terminal end of said protein and from 0–20 additional amino acids attached to the C-terminal end of said protein, wherein said 0–20 amino acids attached to the N-terminal and said 0–20 additional amino acids attached to the C-terminal do not interfere with said U1 RNA specific binding property of said RNA recognition motif.

10. The complex of claim 9, wherein said protein (i) is a protein having amino acid sequence (I) or a protein having at least 35% sequence similarity with said sequence (I).

11. The complex of claim 9, wherein said protein (i) is a protein having amino acid sequence (II) or a protein having at least 35% sequence similarity with said sequence (II).

12. The complex of claim 9, wherein said protein (i) is a protein having the amino acid sequence of residues 92 to 211 of Sequence III and which may include additional residues up to 1 to 240 of sequence (III), or of a protein having at least 35% sequence similarity with said sequence (III).

13. The complex of claim 9, wherein said protein (i) is a protein consisting of an amino acid sequence which is one member selected from the group consisting of the sequences in FIG. 6 to which up to 10 amino acids are attached at each end of said sequences, wherein said 10 amino acids are the 10 amino acids occurring in the corresponding native protein sequences shown in FIG. 6.

14. The complex of claim 9, wherein said protein (i) is a protein consisting of an amino acid sequence which is one member selected from the group consisting of the sequences in FIG. 6 to which up to 20 amino acids are attached at each end of said sequences, wherein said 20 amino acids are the 20 amino acids occurring in the corresponding native protein sequences shown in FIG. 6.

* * * * *